(12) United States Patent
Kandori

(10) Patent No.: US 10,234,431 B2
(45) Date of Patent: Mar. 19, 2019

(54) TRANSDUCER UNIT, ACOUSTIC PROBE INCLUDING THE TRANSDUCER UNIT, AND PHOTOACOUSTIC APPARATUS INCLUDING THE ACOUSTIC PROBE

(71) Applicant: CANON KABUSHIKI KAISHA, Tokyo (JP)

(72) Inventor: Atsushi Kandori, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 215 days.

(21) Appl. No.: 15/253,419

(22) Filed: Aug. 31, 2016

(65) Prior Publication Data

US 2017/0067856 A1  Mar. 9, 2017

(30) Foreign Application Priority Data

Sep. 4, 2015 (JP) .................. 2015-175014

(51) Int. Cl.
*G01N 29/24* (2006.01)
*A61B 8/08* (2006.01)
(Continued)

(52) U.S. Cl.
CPC ....... *G01N 29/2406* (2013.01); *A61B 5/0095* (2013.01); *A61B 8/0825* (2013.01); *A61B 8/4209* (2013.01); *A61B 8/4488* (2013.01); *G01H 11/00* (2013.01); *G01N 29/0654* (2013.01); *G01N 29/2418* (2013.01); *H01L 23/481* (2013.01); *A61B 5/4312* (2013.01); (Continued)

(58) Field of Classification Search
CPC ........... G01N 29/2406; G01N 29/0654; G01N 29/2418; G01N 2291/101; A61B 8/4209; A61B 5/0095; A61B 8/4488; A61B 8/0825; A61B 2562/0204; A61B 5/708; A61B 5/4312; A61B 2562/04; H01L 23/481; H01L 2224/73265; H01L 2224/48091; G01H 11/00
See application file for complete search history.

(56) References Cited

U.S. PATENT DOCUMENTS

2007/0244392 A1  10/2007  Tezuka
2009/0062656 A1  3/2009  Hyuga
(Continued)

FOREIGN PATENT DOCUMENTS

CN  102639258 A  8/2012
CN  103348539 A  10/2013
(Continued)

*Primary Examiner* — Daniel Pihulic
(74) *Attorney, Agent, or Firm* — Canon U.S.A., Inc. IP Division

(57) ABSTRACT

A transducer unit includes a substrate, a capacitive transducer provided on the substrate and configured to receive an acoustic wave generated when a subject is irradiated with light from a light source and output an electric signal, a circuit substrate including a current/voltage conversion circuit configured to convert a current output from the capacitive transducer into a voltage, and a flexible printed wiring that electrically connects the capacitive transducer to the current/voltage conversion circuit, in which the circuit substrate is provided on a surface side opposite to a surface where the capacitive transducer is provided among surfaces of the substrate.

34 Claims, 38 Drawing Sheets

(51) Int. Cl.
*A61B 8/00* (2006.01)
*A61B 5/00* (2006.01)
*G01H 11/00* (2006.01)
*H01L 23/48* (2006.01)
*G01N 29/06* (2006.01)

(52) U.S. Cl.
CPC ....... *A61B 5/708* (2013.01); *A61B 2562/0204* (2013.01); *A61B 2562/04* (2013.01); *G01N 2291/101* (2013.01); *H01L 2224/48091* (2013.01); *H01L 2224/73265* (2013.01)

(56) References Cited

U.S. PATENT DOCUMENTS

| | | |
|---|---|---|
| 2011/0169510 A1 | 7/2011 | Kandori et al. |
| 2011/0206865 A1 | 8/2011 | Wall et al. |
| 2011/0306865 A1 | 12/2011 | Thornton et al. |
| 2013/0267853 A1 | 10/2013 | Dausch |
| 2014/0211592 A1 | 7/2014 | Miyazawa |
| 2014/0290371 A1 | 10/2014 | Nakamura |
| 2015/0016222 A1 | 1/2015 | Kandori |
| 2015/0112181 A1* | 4/2015 | Yoon .................... A61B 5/0095 600/407 |
| 2016/0153940 A1* | 6/2016 | Kandori ............. G01N 29/2406 73/632 |
| 2017/0067856 A1* | 3/2017 | Kandori ............. G01N 29/0654 |
| 2018/0080813 A1* | 3/2018 | Abe ....................... G01H 11/06 |

FOREIGN PATENT DOCUMENTS

| | | | |
|---|---|---|---|
| CN | 103354731 A | 10/2013 | |
| CN | 104068888 A | 10/2014 | |
| CN | 104068892 A | 10/2014 | |
| CN | 104284283 A | 1/2015 | |
| EP | 3147637 A3 * | 5/2017 | ......... G01N 29/2406 |
| JP | 2006061696 A | 3/2006 | |
| JP | 2014197846 A | 10/2014 | |
| JP | 2015019225 A | 1/2015 | |
| WO | 2008146600 A1 | 12/2008 | |

* cited by examiner

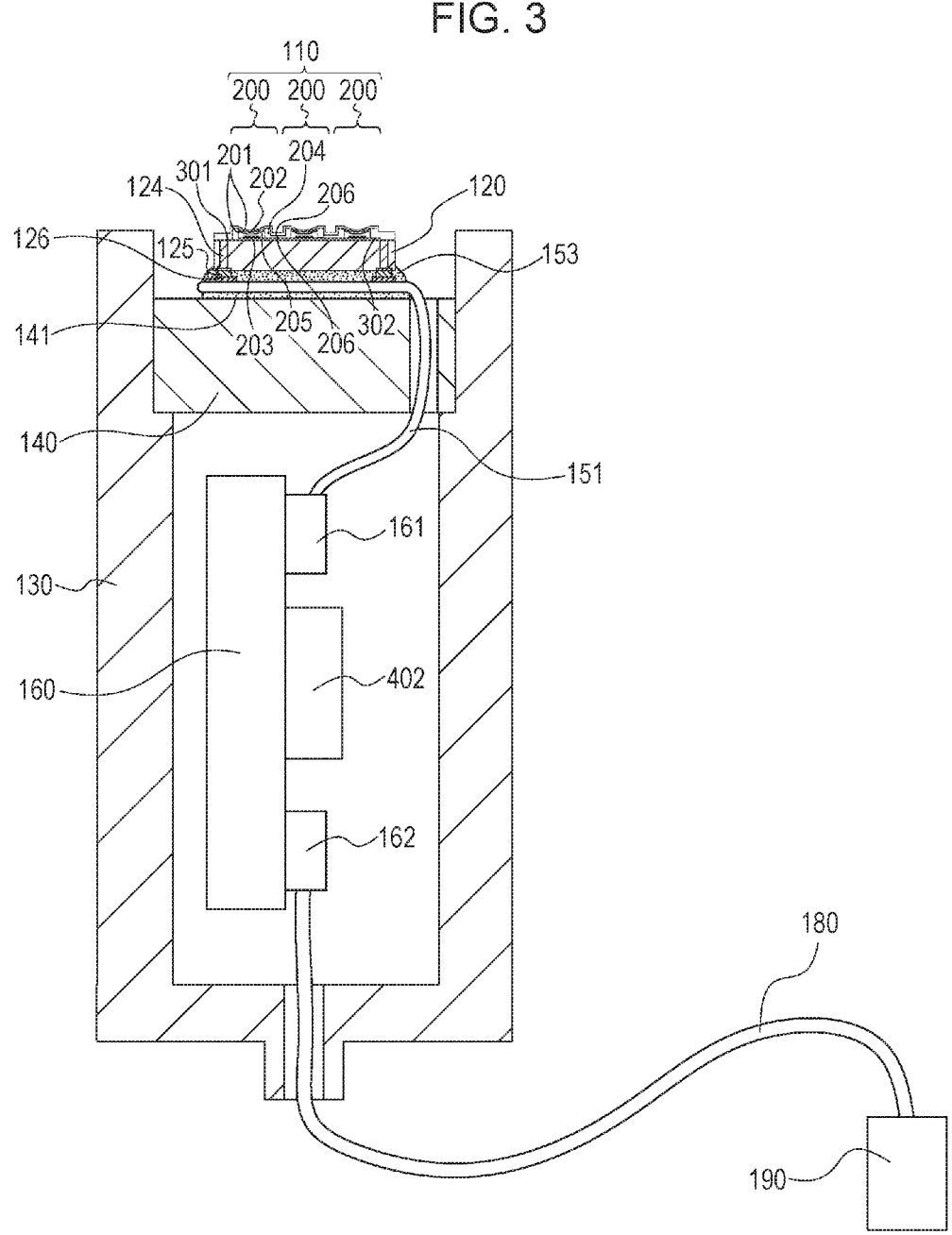

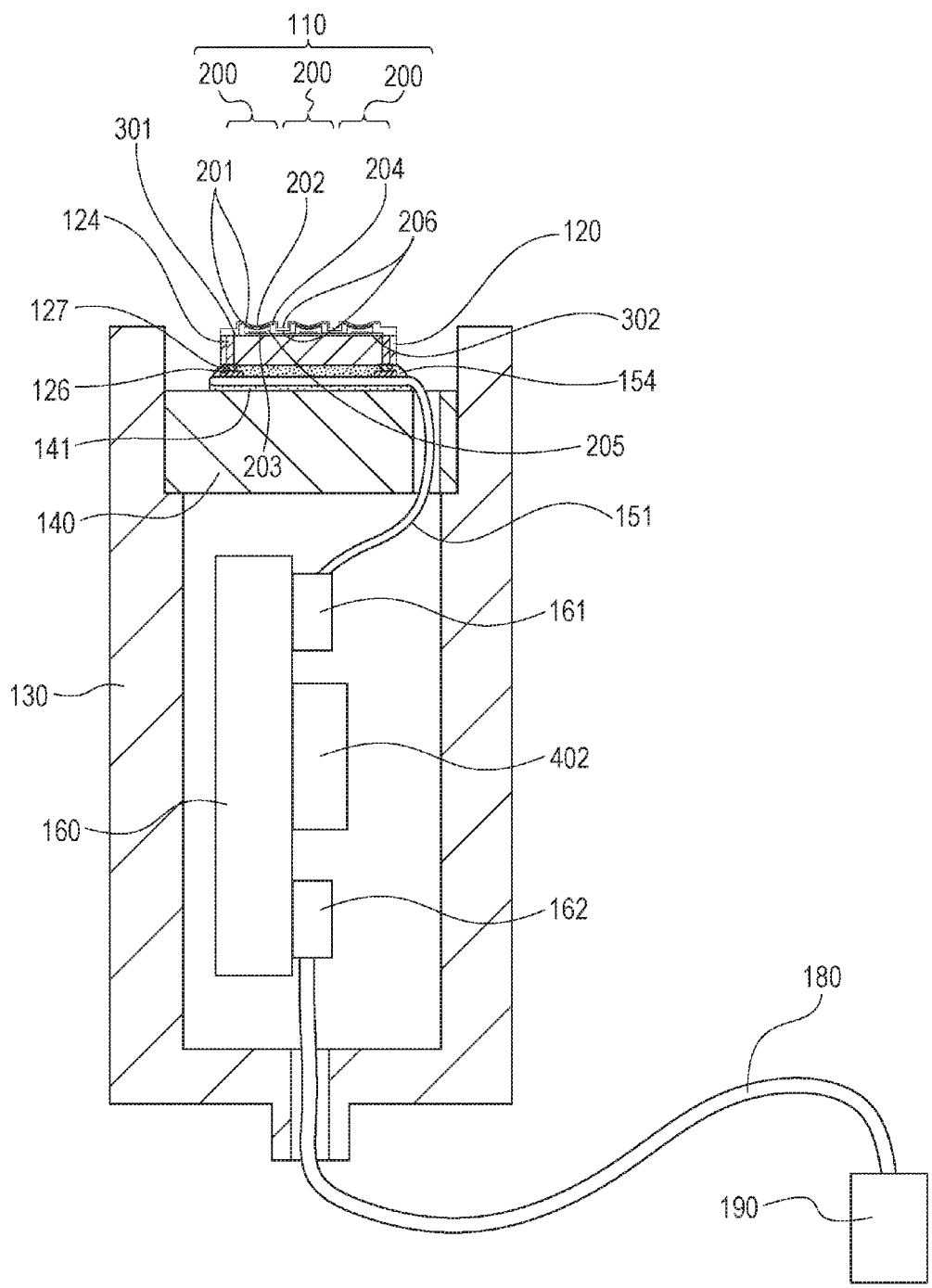

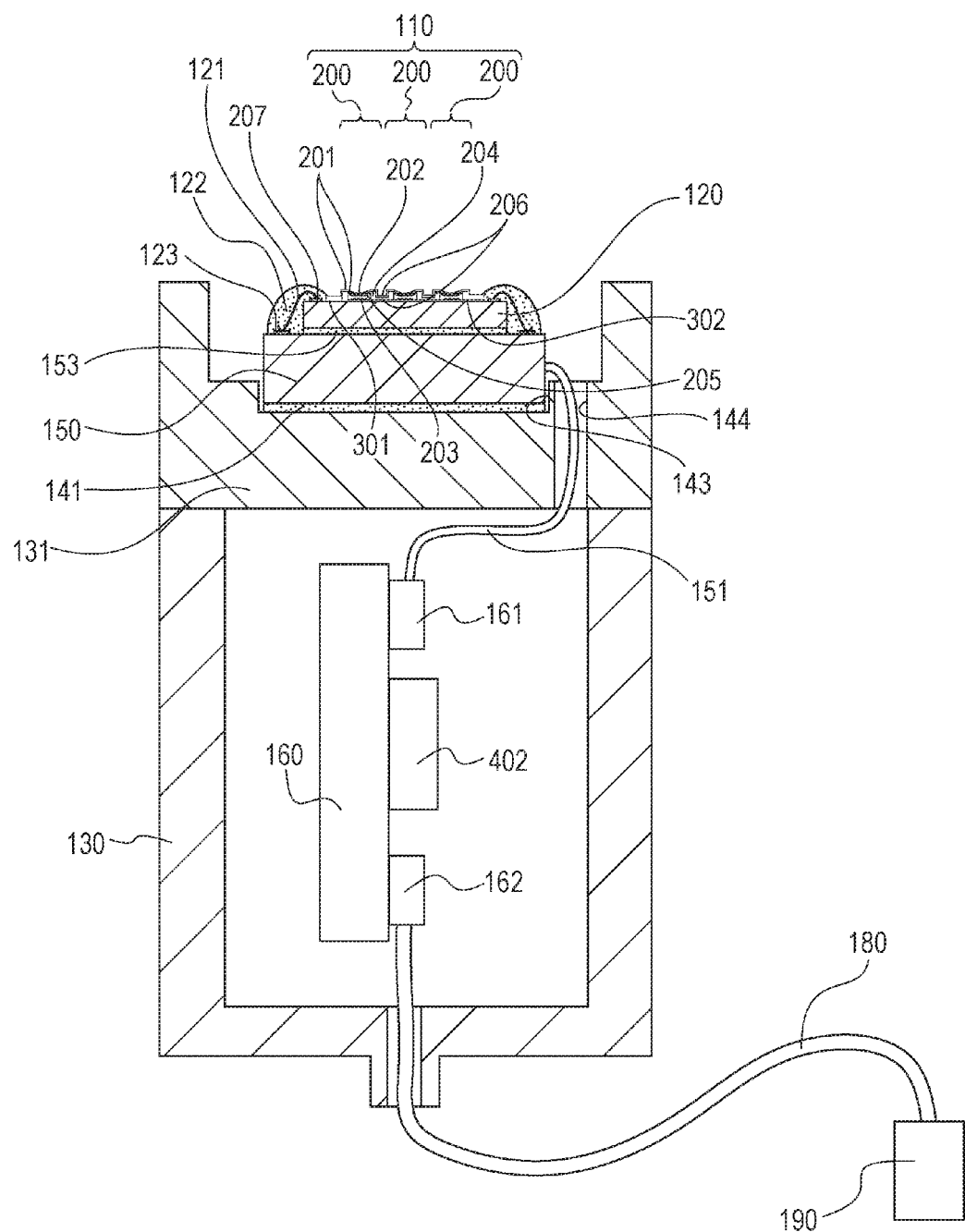

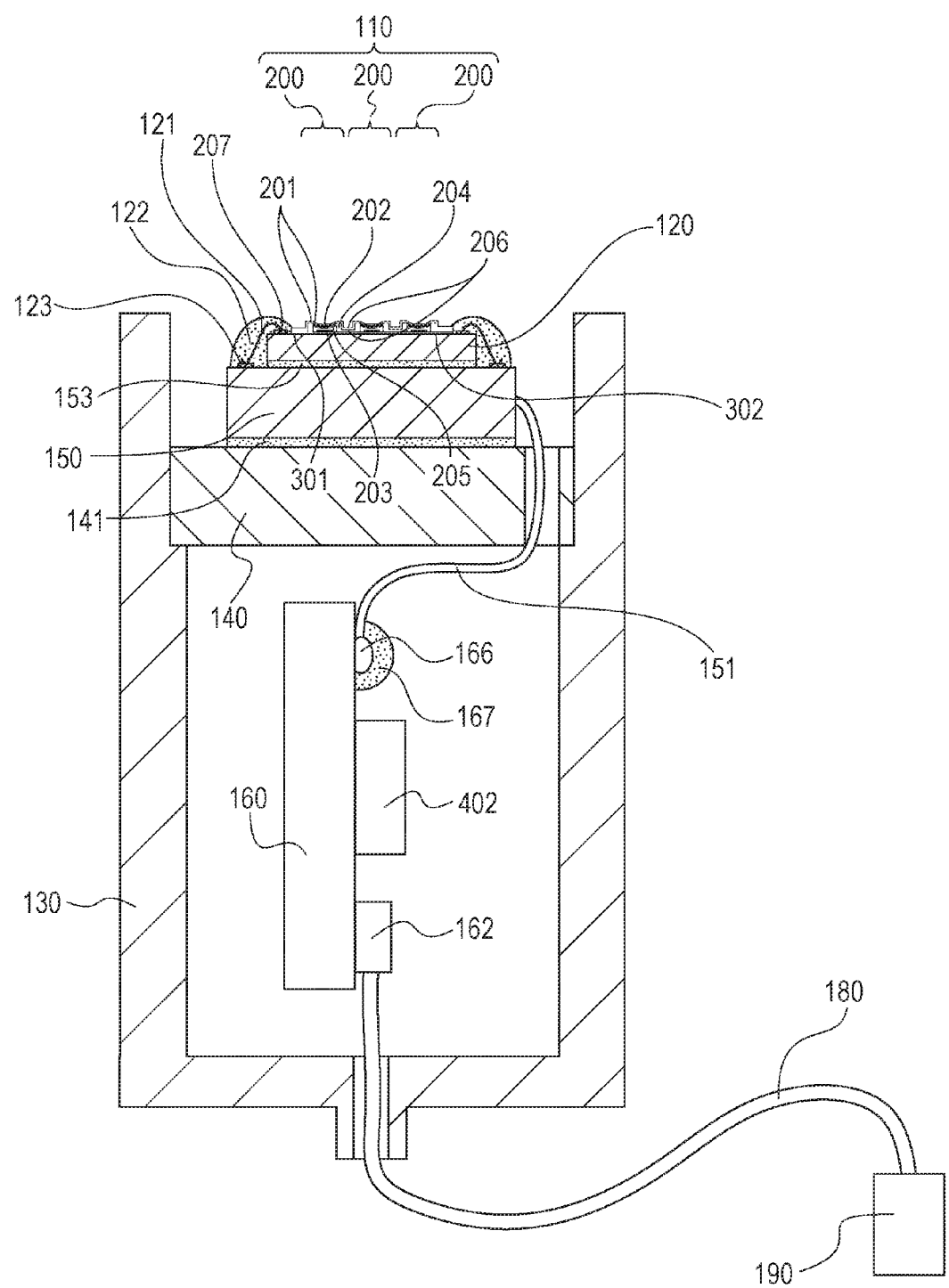

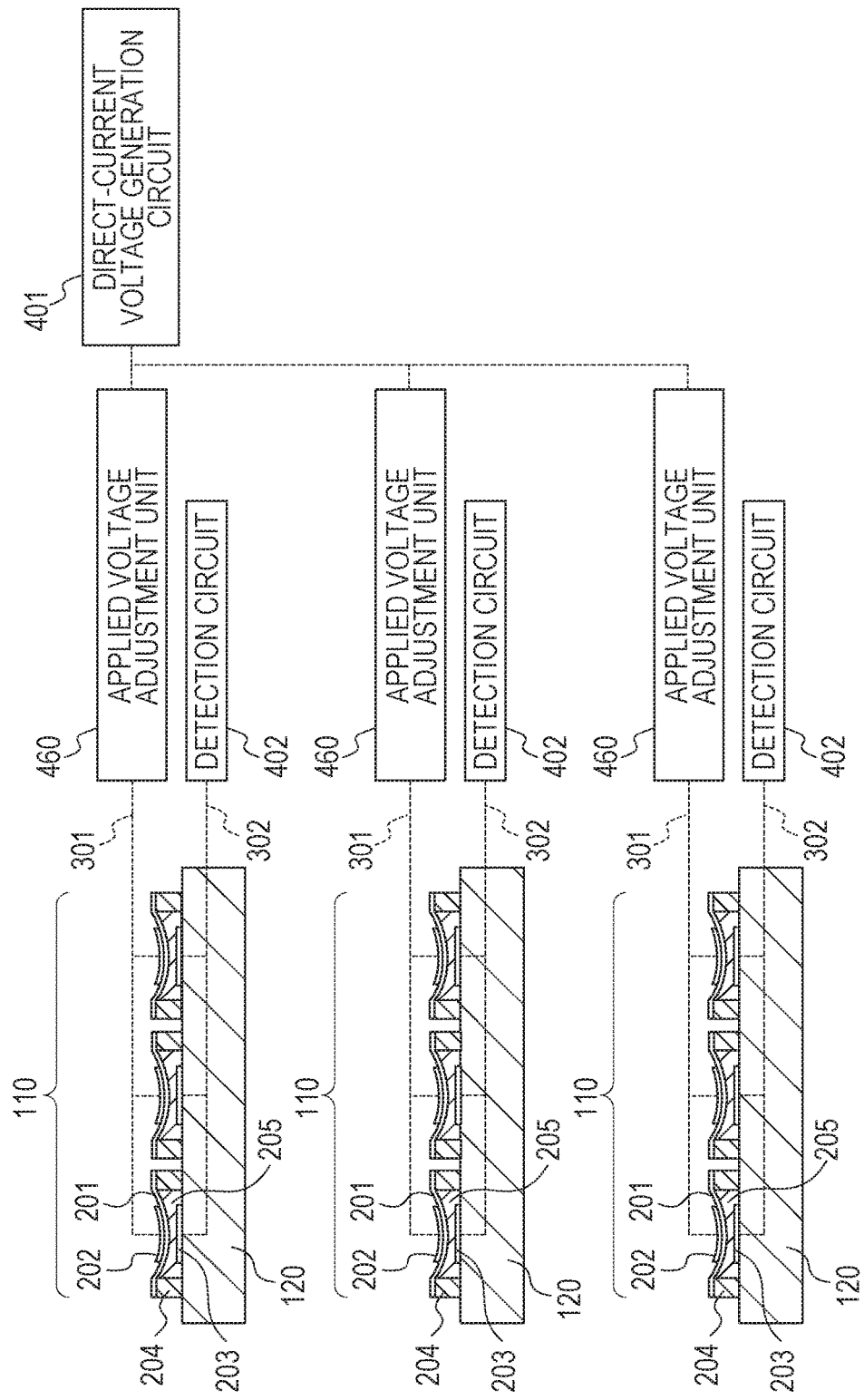

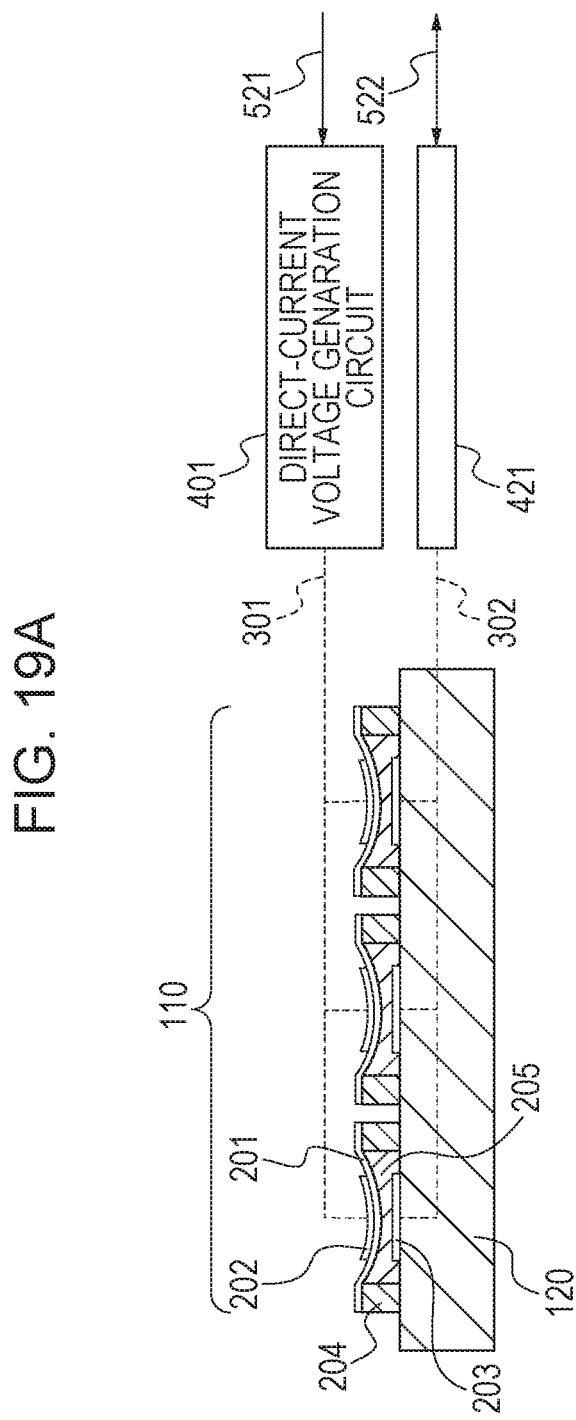

TRANSDUCER UNIT, ACOUSTIC PROBE INCLUDING THE TRANSDUCER UNIT, AND PHOTOACOUSTIC APPARATUS INCLUDING THE ACOUSTIC PROBE

BACKGROUND OF THE INVENTION

Field of the Invention

The present invention relates to a transducer unit, an acoustic probe including the transducer unit, and a photoacoustic apparatus including the acoustic probe.

Description of the Related Art

A measurement system has been proposed in which a subject is irradiated with light, an acoustic wave (typically, an ultrasonic wave, but referred to as a photoacoustic wave in the present specification) is generated from a measurement object in the subject on the basis of a photoacoustic effect, and the generated acoustic wave is received by using a hemispheric ultrasonic probe (U.S. Patent Application Publication No. 2011/0306865, hereinafter referred to as Patent Document 1). The hemispheric ultrasonic probe is constituted by a plurality of ultrasonic transducer elements arranged on a hemispheric surface.

Descriptions will be given with reference to FIG. 23. FIG. 23 illustrates a subject 10, a light source 11, an ultrasonic probe 12, an ultrasonic transducer 13, light beam 21, a photoacoustic wave 22, and a medium 30 (acoustic matching material). The ultrasonic probe 12 has a shape of hemisphere and is provided with a plurality of ultrasonic transducers 13 and the light source 11. The subject 10 is arranged so as to be partially surrounded by the hemisphere of the ultrasonic probe 12, and the medium 30 is filled between the subject 10 and the ultrasonic probe 12. The light source 11 emits the light beam 21 to the subject 10, and the photoacoustic wave 22 generated in the subject is received by the plurality of ultrasonic transducers 13 included in the ultrasonic probe 12 to perform imaging of the subject.

At this time, when the number of ultrasonic transducers arranged on the hemispheric surface of the supporting member is increased, it is possible to improve an image quality of an image of the subject. To increase the number of ultrasonic transducers, the plurality of ultrasonic transducers need to be arranged so as to be in proximity to one another on the hemispheric surface. However, an optimal configuration for arranging the ultrasonic transducers in proximity to one another has not been proposed up to now.

SUMMARY OF THE INVENTION

In view of the above, the present invention aims at providing a photoacoustic probe including a small-sized transducer unit that can be arranged in proximity to a supporting member and a plurality of transducer units arranged in proximity to one another. The transducer unit according to an aspect of the present invention includes: a chip; a capacitive transducer provided on the chip and configured to receive an acoustic wave generated when a subject is irradiated with light from a light source and output an electric signal; a circuit substrate including a current/voltage conversion circuit configured to convert a current output from the capacitive transducer into a voltage; and a flexible printed wiring that electrically connects the capacitive transducer to the current/voltage conversion circuit, in which the circuit substrate is provided on a surface side opposite to a surface where the capacitive transducer is provided among surfaces of the chip.

Further features of the present invention will become apparent from the following description of exemplary embodiments with reference to the attached drawings.

BRIEF DESCRIPTION OF THE DRAWINGS

FIG. 3 is a schematic diagram of the photoacoustic probe according to a second exemplary embodiment of the present invention.

FIGS. 4A and 4B are schematic diagrams of the photoacoustic probe according to a third exemplary embodiment of the present invention.

FIGS. 6A and 6B are schematic diagrams of the photoacoustic probe according to a fifth exemplary embodiment of the present invention.

FIGS. 9A to 9C are schematic diagrams of the photoacoustic probe according to an eighth exemplary embodiment of the present invention.

FIGS. 17A and 17B are schematic diagrams of the photoacoustic probe according to a sixteenth exemplary embodiment of the present invention.

FIGS. 19A and 19B are schematic diagrams of the photoacoustic probe according to an eighteenth exemplary embodiment of the present invention.

DESCRIPTION OF THE EMBODIMENTS

Hereinafter, exemplary embodiments of the present invention will be described with reference to the drawings. A transducer unit according to the present exemplary embodiment includes a chip and a capacitive transducer provided on the chip and configured to receive an acoustic wave generated when a subject is irradiated with light from a light source and output an electric signal. The transducer unit also includes a circuit substrate including a current/voltage conversion circuit configured to convert a current output from the capacitive transducer into a voltage and a flexible printed wiring that electrically connects the capacitive transducer to the current/voltage conversion circuit. It is characterized in that the circuit substrate is provided on a surface (rear side) opposite to a surface on which the capacitive transducer is provided among surfaces of the chip. Hereinafter, detailed descriptions will be given.

First Exemplary Embodiment

Figure 1A:
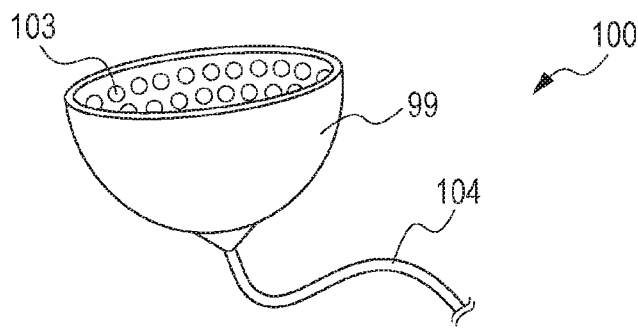
FIGS. 1A to 1E are schematic diagrams of a photoacoustic probe according to a first exemplary embodiment of the present invention.
Figure 1B:
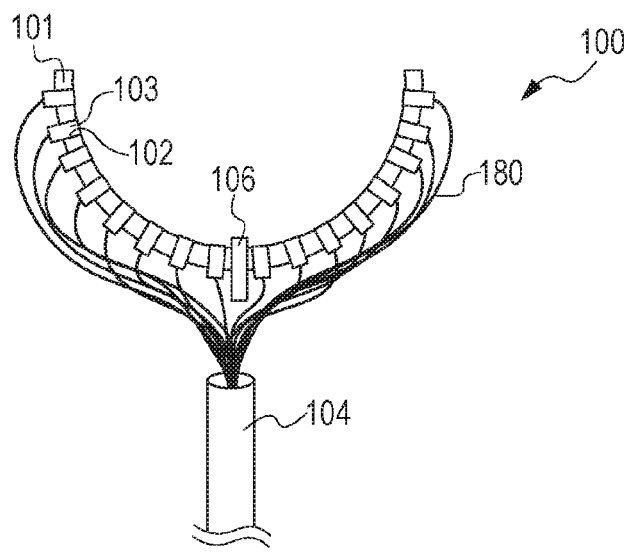

First, with reference to FIGS. 1A to 1E, a photoacoustic probe 100 according to the present exemplary embodiment will be described. FIGS. 1A to 1E illustrate a probe casing 99, a hemispheric supporting member 101, a through hole 102, an ultrasonic transducer unit 103 (hereinafter, which may be simply abbreviated as a transducer unit in some cases), a cable 104, a connector 190, and a light source 106. FIGS. 1A to 1E also illustrate a capacitive transducer 110 (capacitive micromachined ultrasonic transducer, hereinafter referred to as CMUT). FIG. 1A is a schematic diagram of an external appearance of the photoacoustic probe 100 according to the present exemplary embodiment, and FIG. 1B is a schematic diagram for describing a cross section of the photoacoustic probe 100.

The hemispheric supporting member 101 includes a plurality of through holes 102 corresponding to positions where the CMUTs 110 are arranged. The transducer unit 103 has an outer shape corresponding to a shape of the through hole 102 and is inserted and fixed to each of the through holes 102. The transducer unit 103 is provided with the CMUT 110 and arranged such that the CMUT 110 faces a vicinity of the center of the hemisphere. According to the present exemplary embodiment, descriptions will be given of a configuration in which the shape of the through hole 102 is a completely round shape, and the CMUT 110 is arranged in the center of the transducer unit 103.

The light source 106 is arranged in the center of the hemispheric supporting member. A device that can emit light such as a solid-state laser, a semiconductor laser, or an LED can be used as the light source 106. A configuration in which light is guided from a light emitting unit arranged outside by using an optical fiber can also be used. According to the present specification, the descriptions will be given while the configuration in which the light source 106 is arranged in the center of the hemisphere is adopted, but the present invention is not limited to this configuration. One or a plurality of the light sources 106 can be arranged in an arbitrary position in the area where the transducer unit 103 is not arranged in the hemispheric supporting member 101.

According to the present exemplary embodiment, a configuration in which the separate transducer unit 103 is attached to the through hole 102 of the supporting member 101 is adopted. For this reason, the configuration of the supporting member 101 can be set to have an extremely simple shape in which holes are simply opened in the hemispheric member. In addition, the supporting member 101 and the transducer unit 103 are constituted by the separate members, and the transducer unit 103 where the operation has been checked can be selected and used, so that it is also possible to easily improve a yield of the ultrasonic probe 100. Furthermore, when the transducer unit 103 breaks down, it is possible to easily carry out replacement. In addition, by changing the arrangement of the through hole 102 in the supporting member 101, it is possible to easily provide the ultrasonic probe 100 having a different sensor interval. Similarly, a probe having a different radius of the hemisphere can be constituted by the same transducer unit 103 by simply preparing the supporting member 101 having a different radius.

It is characterized in that the CMUT 110 is used as the ultrasonic transducer 110 according to the present exemplary embodiment.

Figure 1C:
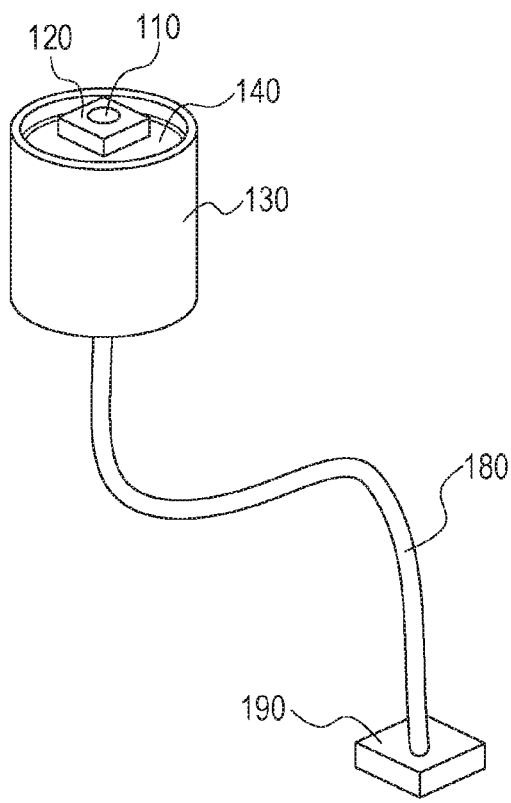

Next, the transducer unit 103 provided with the CMUT 110 used in the present exemplary embodiment will be described with reference to FIG. 1C. FIG. 1C illustrates a chip 120, a casing 130, a supporting member 140, a cable 180, and a connector 190.

The transducer unit 103 includes the cylindrical casing 130 and is provided with the chip 120 supported via the supporting member 140. The CMUT 110 is formed on the chip 120. The chip 120 is arranged such that the CMUT 110 faces the central side of the hemisphere when the transducer unit 103 is attached to the hemispheric supporting member 101 having the through hole. In addition, the plurality of transducer units 103 can be arranged in a spiral manner in the hemisphere. Accordingly, since the transducers are arranged such that an interval of the transducers is uniform as viewed from various angles with respect to the subject, an artifact (virtual image), which is generated because the interval of the transducers is not uniform when subject information is imaged, is hardly generated. For this reason, it is possible to obtain the more detailed subject information. A configuration is adopted in which a front surface of the CMUT 110 is not covered with the casing 130, and the acoustic wave from the outside of the transducer unit 103 reaches the front surface of the CMUT 110. On the other hand, the cable 180 for a connection with the outside is drawn out from a bottom surface.

The cables 180 from the respective transducer units 103 may mutually have different lengths in accordance with lengths to connection destinations (such as the substrate) of the respective cables 180. Accordingly, the lengths of the cables are optimized to have lengths necessary for the arrangement, and the signals can be transmitted to the outside while generation of unnecessary cables (overlong cables) is suppressed as much as possible. For this reason, miniaturization and weight lightening of the probe as a whole can be realized. In addition, while colors of the respective cables are changed, it is possible to improve operability at the time of attachment to the hemispheric supporting member and reduce the number of connection errors due to erroneous recognitions. In particular, while cables having different lengths are set to have mutually different colors, it is possible to reduce the number of erroneous recognitions with regard to the lengths of the cables. In addition, the lengths of the respective transducer units may be varied depending on a position of the supporting member 101. Accordingly, an interference with the surrounding member can be avoided. In addition, while the lengths are alternately varied, the shorter transducer unit is attached at the time of assembly, and thereafter, the longer transducer unit is attached, so that the attachment can be performed without significantly degrading the operability even in an area of a high arrangement density. Furthermore, colors of connectors to be connected to the cables 180 having mutually different lengths may also be mutually varied. Accordingly, it is possible to improve the operability at the time of the attachment to the hemispheric supporting member and reduce the number of connection errors due to the erroneous recognitions.

In addition, respective cables branched from a single cable may be connected to the plurality of transducer units 103, and a single bundled cable thereof may be connected to an external apparatus. With this configuration, it is possible to reduce a thickness of the cable connected to the external apparatus or decrease the number of cables. The respective transducer units 103 may also be connected in series to a single cable. Accordingly, a power supply of a detection circuit commonly applied to the transducer units or a line of a direct-current (DC) voltage can be commonly used, and it is possible to reduce the thickness of the cable connected to the external apparatus or decrease the number of cables. Furthermore, the number of pins or types may be mutually varied, and diameters and shapes of holes of the respective through holes may be mutually varied. While the change is made in accordance with the arrangement position, it is possible to improve the operability at the time of the attachment to the hemispheric supporting member and reduce the number of connection errors due to the erroneous recognitions.

A configuration can also be adopted in which a printed circuit board (PCB; rigid flexible printed circuit board) is provided along the hemispheric shape of the supporting member 101, and the cables from the respective transducer units 103 are bundled in the PCB, and the cables connected to the outside are drawn out. With the above-described configuration, it is possible to decrease the number of cables drawn out to the outside. Furthermore, since it is sufficient when the cable is drawn round to the area in proximity to the supporting member 101, the length of the cable itself can be significantly shortened, so that it is possible to realize the miniaturization and the weight lightening of the probe. It should be noted that a bundle structure for bundling the cables may be provided.

The transducer unit 103 inserted to the supporting member 101 can also be bent to have an L-shaped configuration. While the above-described configuration is adopted, a radial spread of the transducer units 103 from the supporting member 101 can be set to be small when viewed from the subject side, and the area occupied by the acoustic probes can be reduced. It should be noted that the L-shaped configuration mentioned herein is not limited to be perpendicular.

In addition, a detection signal of the CMUT is converted into a digital signal in the transducer unit to be wirelessly transmitted to an external signal processing apparatus without using the respective cables, and the signal may be processed in the signal processing apparatus to obtain an image of the subject. Accordingly, it becomes unnecessary to prepare a wiring used for the signal to be transmitted to the external apparatus, and it is possible to realize the miniaturization and the weight lightening of the probe.

In a case where the supporting member 101 is provided with a camera (not illustrated) configured to monitor the subject, a light emitting diode (LED) can be provided such that the subject is irradiated with light. The number of LED may be one or more, and a configuration may be adopted in which the LED is provided to each of the transducer units 103. Accordingly, the entire subject can be uniformly irradiated with light, and a state of the subject can be monitored by the camera more accurately.

FIGS. 1A to 1E illustrate the example in which the transducer units 103 are provided so as to be spaced away from each other, but the plurality of transducer units 103 may be bundled and provided so as to have a shape having a concave part. In the above-described case, such an advantage is realized that the transducer units 103 can be arranged at a high density.

Figure 1D:
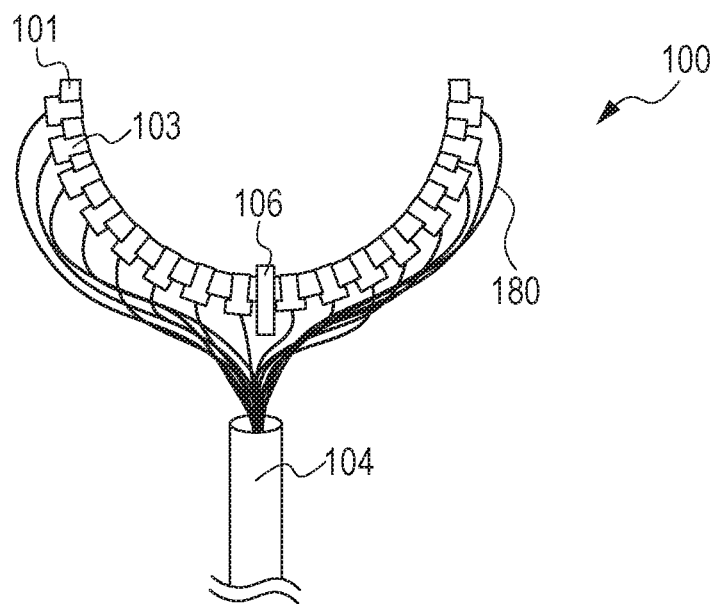
Figure 1E:
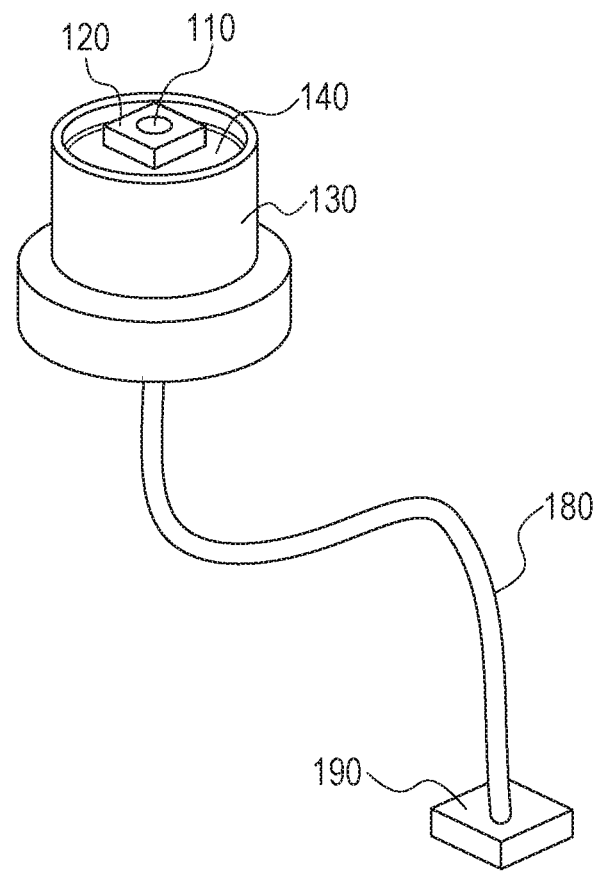

In FIGS. 1B and 1C, the descriptions have been given that the transducer unit 103 has the tubular shape, but the present exemplary embodiment is not limited to this. As illustrated in FIGS. 1D and 1E, the transducer unit having a shape in which the thickness on the cable attachment side is larger than the diameter of the through hole 102 can be used. Accordingly, the position of the transducer unit 103 with respect to the supporting member 101 can be accurately determined with the simple configuration. For this reason, the plurality of ultrasonic transducers 110 can be arranged in a hemispherical manner at a satisfactory accuracy with the simple configuration, and the information from the subject can be accurately obtained.

The CMUT is fabricated on the chip made of silicon by using a micro electro mechanical systems (MEMS) process to which a semiconductor process is applied. Descriptions will be given with reference to FIGS. 2A to 2D.

Figure 2A:
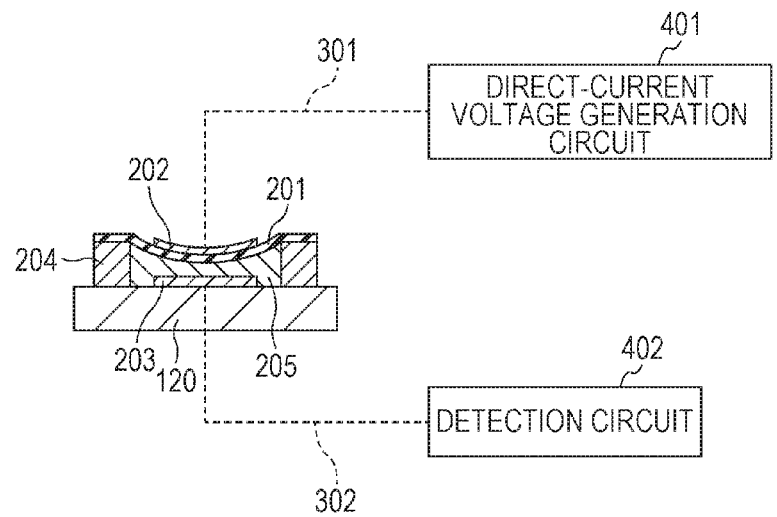
FIGS. 2A to 2D are schematic diagrams of the photoacoustic probe according to the first exemplary embodiment of the present invention.

First, the transducer unit 103 will be described. FIG. 2A is a schematic diagram of the transducer unit 103. FIGS. 2A to 2D illustrate the chip 120 (substrate), a vibrating membrane 201, a first electrode 202, a second electrode 203, a supporting part 204, a gap 205, a first wiring 301, a second wiring 302, a direct-current (DC) voltage generation unit 401, and a detection circuit 402.

The vibrating membrane 201 has a configuration of being supported on the chip 120 by the supporting part 204 and receiving the ultrasonic wave to vibrate. A first electrode 202 is arranged on the vibrating membrane 201, and a second electrode 203 is arranged at the position facing the first electrode 202 on the chip 120. The first electrode 202 and the second electrode 203 that face each other while sandwiching the vibrating membrane 201 and the gap 205 are set as a pair and referred to as a cell 200.

The first electrode 202 is drawn out to the outside of the chip 120 via the first wiring 301 to be connected to the DC voltage generation unit 401, and the second electrode 203 is drawn out to the outside of the chip 120 via the second wiring 302 to the detection circuit 402. While the DC voltage generation unit 401 is used, a potential difference at a several tens of volts to a several hundreds of volts is generated between the first electrode 202 and the second electrode 203. A configuration is adopted in which a value of the applied potential difference can be adjusted by the DC voltage generation unit 401. While the vibrating membrane 201 and the first electrode 202 vibrate, a distance between the first electrode 202 and the second electrode 203 is changed, and an electrostatic capacitance between the electrodes is changed. Since the potential difference exists between the electrodes, a minute current is generated in accordance with the capacitance change. The minute current is converted from the current to a voltage by the detection circuit 402 corrected to the second electrode 203 and is output.

The CMUT 110 used in the present exemplary embodiment has a feature that response at the time of the reception of the ultrasonic wave is satisfactory and a frequency band is wide as compared with a currently widely used piezoelectric ultrasonic transducer.

Transducer Unit

According to the present exemplary embodiment, a significant feature is that a circuit substrate 160 provided with the detection circuit 402 is arranged so as to be perpendicular to the chip 120 provided with the CMUT 110. Descriptions will be given of a specific configuration with reference to FIGS. 2B and 2C.

Figure 2B:
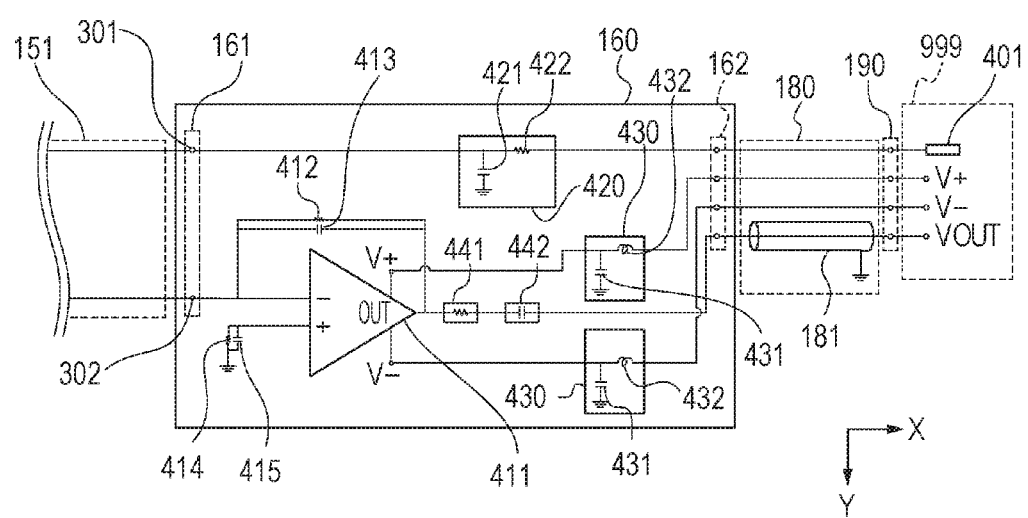
Figure 2C:
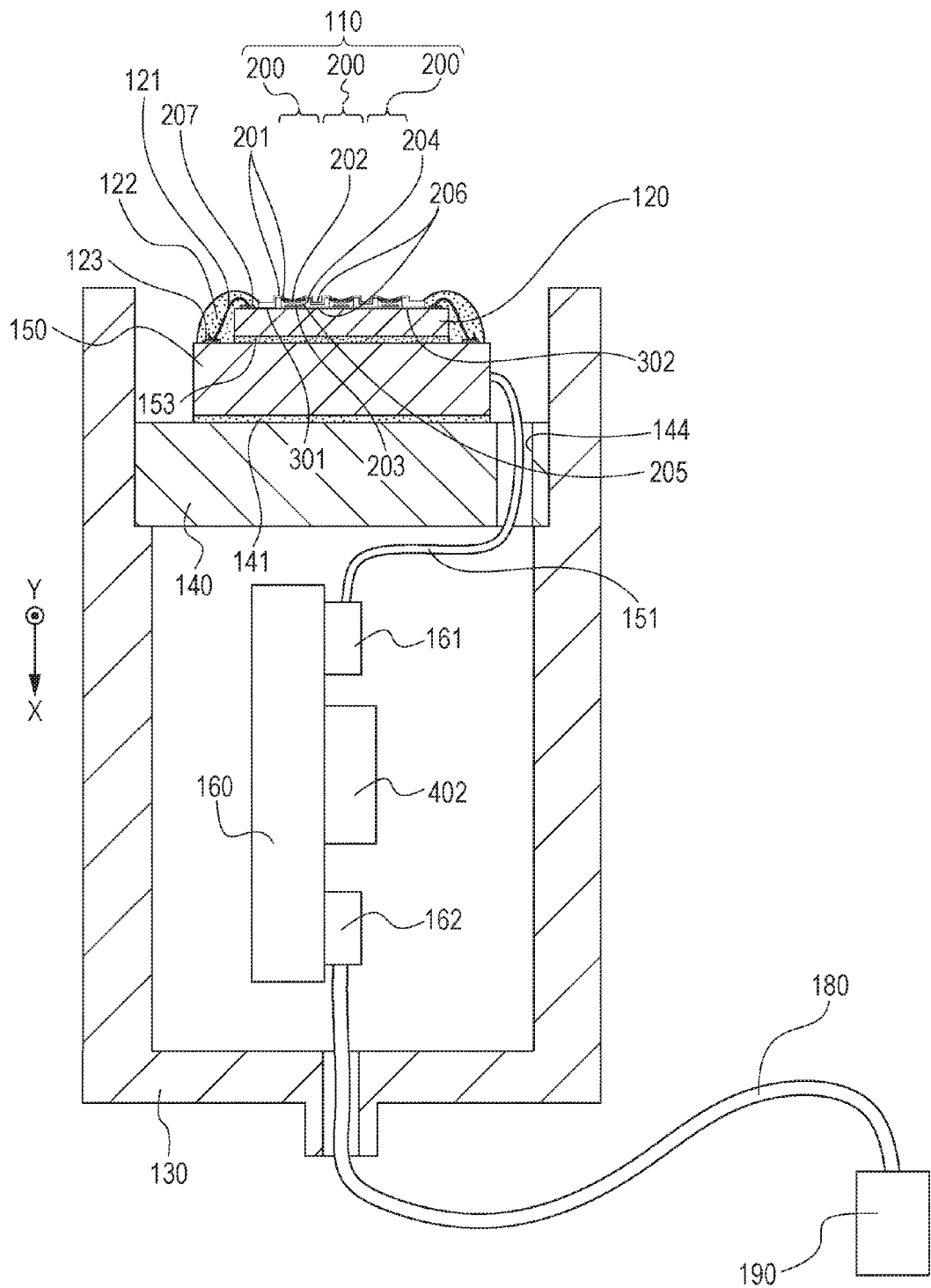

FIG. 2C is a schematic diagram for describing a positional relationship between the chip 120 and the circuit substrate 160 in the transducer unit 103.

The chip 120 where an element of the CMUT 110 is arranged is held by a rigid substrate 150. The rigid substrate 150 is fixed on the supporting member 140 by adhesive 141. An electrode 207 connected to the first and second wirings 301 and 302 on the chip 120 and a wiring on the rigid substrate 150 are electrically connected with each other by a wire 121. The wire 121 is provided by a sealant material 122. A thin film electrode layer 123 having patterning is provided to a front surface of the rigid substrate 150 holding the chip 120 and is connected to an internal conductive layer (not illustrated) by a via (not illustrated) provided in the substrate. The rigid substrate 150 is integrally formed with a flexible printed wiring 151, and the wiring inside the rigid substrate 150 can be drawn out to the circuit substrate 160 connected by a flexible printed wiring connector 161 via the flexible printed wiring 151. An easily integrated configuration of the rigid substrate 150 and the flexible printed wiring 151 can be realized by using a fabrication technology of the rigid flexible printed circuit board. It should be noted that a configuration can be adopted in which the surface opposite to the surface where the CMUT 110 is arranged among the surfaces of the chip 120 is arranged at the position facing the electrode arranged on the rigid substrate 150 provided to the rigid flexible printed circuit board, and the above-described electrode and the CMUT 110 are electrically connected to each other. In addition, a configuration can be adopted in which the surface opposite to the surface where the CMUT 110 is arranged among the surfaces of the chip is arranged at the position facing the flexible printed wiring 151, and the CMUT 110 and the flexible printed wiring 151 are electrically connected to each other. While these configurations are adopted, it becomes unnecessary to provide the area for the connection by the wire 121, and the necessary area by the electric connection part can be minimized. In addition, it becomes unnecessary to provide the wire 121 or the sealant material 122, and the part protruding with respect to the CMUT does not exist on the surface of the substrate 120, so that the influence to an acoustic characteristic is not received at the time of the reception of the photoacoustic wave (ultrasonic wave).

According to the present exemplary embodiment, since the flexible printed wiring 151 is used as the wiring from the chip 120 to the detection circuit 402, it is possible to draw out the wiring in the perpendicular direction with respect to the plane direction of the chip 120. For this reason, while the connection part of the chip 120 and the detection circuit 402 is minimized, it is possible to provide the small-sized transducer unit.

To drive the CMUT 110, it is necessary to perform an application of a DC voltage corresponding to a high voltage from a several tens of bolts to a several hundreds of bolts. In addition, the CMUT 110 needs the circuit substrate 160 including the current/voltage conversion circuit in order to read out a voltage change amount by the photoacoustic wave (ultrasonic wave) as a current change amount. In view of the above, the flexible printed wiring 151 is used to electrically connect the CMUT 110 to the circuit substrate 160.

At this time, in order that the voltage does not exceed a dielectric strength voltage of the flexible printed wiring 151, an interval for the wirings for applying the voltage to the CMUT 110 needs to be wide in the flexible printed wiring 151. Furthermore, since the electrode interval for connecting the flexible printed wiring 151 to the circuit substrate 160 also needs to be wide, the area of the circuit substrate 160 needs to be wide so that the electrode interval can be set to be wide. If the circuit substrate 160 is provided on a plane direction of the chip (substrate) 120 where the CMUT 110 is provided, the area occupied by the circuit substrate 160 is added in addition to the area occupied by the CMUT 110, and the diameter of the transducer unit 103 is increased. As a result, it becomes difficult to provide a large number of transducer units 103 to the supporting member 101.

In view of the above, according to the present exemplary embodiment, the circuit substrate 160 is provided on the side of the surface opposite to the surface where the CMUT 110 is provided among the surfaces of the substrate 120. For this reason, the miniaturization can be realized without increasing the diameter of the transducer unit 160. As a result, a large number of transducer units 103 can be provided to the supporting member 101, and it is possible to realize an increase in an image quality of the subject since the photoacoustic signals can be received by a large number of CMUTs.

The supporting member 140 includes a through hole 144 through which the flexible printed wiring 151 can pass. Accordingly, the supporting member 140 draws out the wiring to the area on the opposite surface side to the surface where the chip 120 is arranged, and the circuit substrate 160 can be arranged. Although not illustrated in the drawing, the inside of the through hole 144 is preferably sealed up by a sealant material. Accordingly, it is possible to avoid a situation where ultrasonic gel or the like on the transducer side flows to the circuit substrate 160 side, and an electric reliability can be increased.

The detection circuit 402 is provided on the circuit substrate 160 and arranged so as to be perpendicular to the chip 120. An outer shape of the circuit substrate 160 is a rectangular parallelepiped shape according to the present exemplary embodiment, but the present invention is not limited to this. In addition, the circuit substrate 160 has the connection part (the flexible printed wiring connector 161) with the flexible printed wiring 151 arranged at one end and is provided with a connection part (a connector 162) with the cable 180 at the other end.

FIG. 2B is a schematic diagram of wirings and circuits among the flexible printed wiring 151, the circuit substrate 160, and the cable 180 in the transducer unit 103.

The detection circuit 402 can be constituted by a transimpedance circuit using an operation amplifier. A transimpedance circuit using an operation amplifier 411 has a resistance 412 and a condenser 413 arranged in parallel to a negative feedback part of the operation amplifier, and a current input at a feedback part is converted into a voltage. Since a feedback characteristic of the operation amplifier exists, by using the operation amplifier having a broad band region, a current/voltage conversion efficiency can reduce an influence of a parasitic capacitance existing at the input wiring. For this reason, an excellent reception characteristic in which a decrease in a reception sensitivity is small is obtained as a reception characteristic having a wide frequency band with respect to the CMUT.

According to the present exemplary embodiment, since the transimpedance circuit configuration using the operation amplifier 411 is used for the detection circuit 402, an influence of a parasitic capacitance at an input terminal of the detection circuit 402 is hardly affected. For this reason, it is possible to provide the photoacoustic probe in which the degradation in the reception characteristic caused by the parasitic capacitance is small.

A power supply of the detection circuit 402 needs to be stably supplied with a current for driving the circuit. When a wiring resistance exists in the cable 180, the current supplied to the detection circuit 402 becomes unstable, which may affect a current-voltage conversion characteristic in the detection circuit 402 in some cases. According to the present exemplary embodiment, since a stabilization circuit 430 for the power supply of the detection circuit is provided, it is possible to stably supply the current used by the detection circuit 402, and the desired current-voltage conversion characteristic is obtained in the detection circuit 402. The stabilization circuit 430 according to the present exemplary embodiment can be easily constituted by a condenser 431 and a coil 432 as illustrated in FIG. 2B.

It is characterized in that an impedance matching resistance 441 with the wiring 310 is connected between an output terminal of the detection circuit 402 and a wiring 310. A coaxial cable 181 is preferably used as the wiring 310 that outputs an output signal from the detection circuit 402 to the apparatus side. When the coaxial cable 181 is used, it is possible to avoid a situation where the noise from the outside is superimposed on the signal. However, a reflection or the like is generated in the wiring when the wiring is lengthened, which may degrade the characteristic of the signal. In FIG. 2B, the impedance matching resistance 441 that realizes matching with a wiring impedance of the wiring 181 corresponding to the coaxial cable is provided. For this reason, because of an inconsistency of the impedance between the circuit substrate 160 and the coaxial cable 181, the generation of the degradation in the output signal can be suppressed. For this reason, it is possible to provide the transducer unit 103 where the degradation of the detection signal in the cable 180 that bundles a plurality of wirings is small.

A condenser 442 is connected between the output terminal of the detection circuit 402 and the wiring 310. To receive the photoacoustic wave, it is sufficient when the CMUT 110 can detect a signal at a certain frequency (from several hundreds of kilohertz to several megahertz) or above. In FIG. 2B, since the condenser 442 is provided at the output terminal of the detection circuit 402, the DC component of the output voltage can be cut. If the DC component exists in the output voltage, the power consumption is increased since a current regularly flows in the wiring. According to the circuit configuration of FIG. 2B, since the DC voltage is cut, the current that regularly flows can be eliminated, and the power consumption can be decreased. For this reason, it is possible to provide the transducer unit 103 with the low power consumption.

Furthermore, a configuration in which the stabilization circuit 420 for the DC voltage is provided on the circuit substrate 160 is preferably adopted. The coaxial cable 181, power supply lines for the current/voltage conversion circuit, and the wiring 310 are provided as one set in the cable 180 according to the present exemplary embodiment.

Since the transducer units 103 distributed and arranged in the hemispheric supporting member 101 and the connector 190 connected to the external apparatus (not illustrated) are distanced from each other, the cable 180 connecting therebetween has a certain length. For this reason, because of the wiring resistance of the wiring in the cable 180, a DC voltage Vb1 on the circuit substrate 160 is different from a DC voltage Vb0 in the connector on the apparatus side. The reception characteristic of the CMUT 110 is significantly affected because of a difference between a potential applied to the first electrode 202 and a potential applied to the second electrode 203. For this reason, if the DC voltage Vb1 applied to the CMUT 110 is different from the DC voltage Vb0 generated in the DC voltage generation unit 401, a desired reception characteristic is not obtained.

According to the present exemplary embodiment, since the stabilization circuit 420 for the DC voltage is provided, the DC voltage Vb1 applied to the CMUT 110 can be matched with the DC voltage Vb0 generated in the DC voltage generation unit 401. For this reason, it is possible to reduce the influence affected by the wiring resistance of the cable 180 on the reception characteristic of the CMUT 110.

With regard to the stabilization circuit 420 for the DC voltage according to the present exemplary embodiment, it is sufficient when the input impedance of the stabilization circuit 420 for the DC voltage is sufficiently lower than the wiring resistance of the cable 180. Specifically, as illustrated in FIG. 2B, the stabilization circuit 420 can be easily constituted by a high breakdown condenser 421 and a resistance 422. The present exemplary embodiment is not limited to the circuit configuration illustrated in FIG. 2B, and it is sufficient when a circuit that can set the value of the DC voltage Vb1 on the circuit substrate 160 side and the value of the DC voltage Vb0 in the connector on the apparatus side to be close to each other is used.

An outer shape of the circuit substrate 160 according to the present exemplary embodiment is a rectangular parallelepiped shape. In the circuit substrate 160, a connection part (the flexible printed wiring connector 161) with the flexible printed wiring 151 is arranged at one end, and a connection part (the connector 162) with the cable 180 is provided at the other end. With the above-described configuration, the connection between the CMUT 110 and the detection circuit 402 can be concentrated at the one end of the circuit substrate 160. The connection between the cable 180 and the detection circuit 402 for the connection with the external apparatus can also be concentrated at the other end of the circuit substrate 160. In addition, while the wirings and the circuits illustrated in FIG. 2C are arranged along an X direction of the circuit substrate 160, the wirings in the circuit substrate 160 can be most efficiently arranged, and it is possible to narrow the width of the circuit substrate 160.

As described above, in the photoacoustic probe according to the present exemplary embodiment, the elongated circuit substrate 160 is arranges so as to be perpendicular to the chip 120 by using the flexible printed wiring 151. For this reason, a projection area used for the arrangement of the detection circuit 402 as viewed from the chip 120 side can be reduced, and it is possible to provide the small-sized transducer unit 103.

The photoacoustic probe 100 according to the present exemplary embodiment is constituted while the ultrasonic transducers 103 are inserted and fixed to the through holes 102 provided to the hemispheric supporting member 101 in a radiating manner from the vicinity of the center of the hemisphere. For this reason, even if the length of the transducer unit 103 is lengthened, this situation does not affect the arrangement interval between the transducer units 103. For this reason, the arrangement interval between the transducer units 103 can be narrowed, and it is possible to provide the photoacoustic probe in which the ultrasonic transducers 110 are arranged at a high density.

Here, another mode of the present exemplary embodiment will be described with reference to FIG. 2D. The chip 120 includes a through wiring 124, and the wiring can be drawn out from the surface where the CMUT 110 is arranged to the opposite surface. The wiring drawn out to the back surface is electrically connected to an electrode 126 on the rigid substrate 150 via a solder bump 125. A space between the chip 120 and the rigid substrate 150 is filled with an underfill material 153.

According to the other mode of the present exemplary embodiment, since the size of the electric connection part between the chip 120 and the rigid substrate 150 can be reduced, it is possible to provide the small-sized transducer unit 103. For this reason, it is possible to provide the photoacoustic probe in which the interval between the transducers 110 is further narrowed.

Figure 2D:
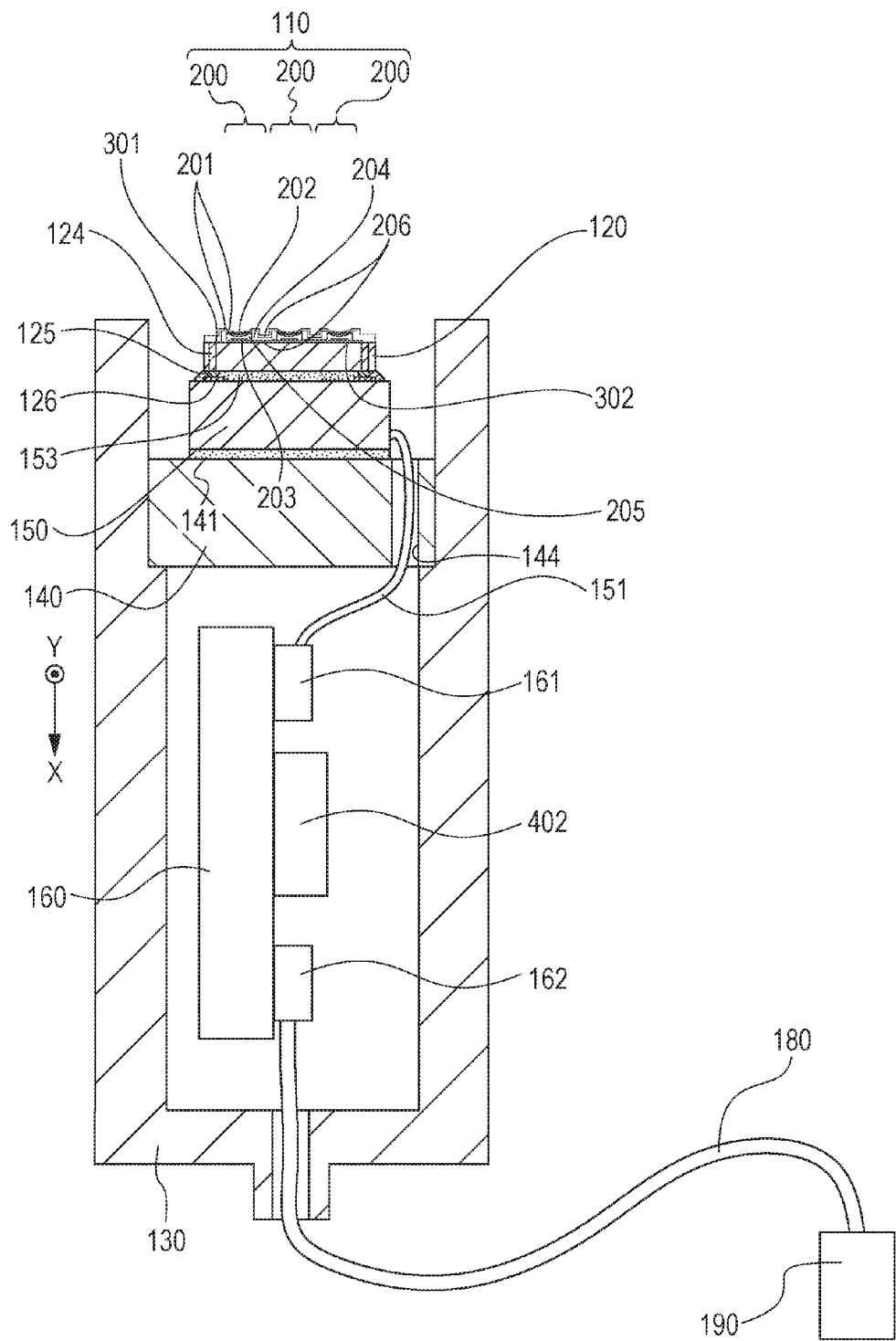

It should be noted that the descriptions have been given by using the solder bump in FIG. 2D, but other exemplary embodiments are not limited to this. A configuration in which the connection is realized by using a gold bump instead of a solder bump 125 can also be adopted. Accordingly, it is possible to provide the photoacoustic probe in which the arrangement can be realized while the arrangement interval of the plurality of ultrasonic transducers is narrowed without using the solder bump.

Second Exemplary Embodiment

A second exemplary embodiment relates to a connection mode of the chip 120 and the flexible printed wiring 151. Aspects other than the connection mode are the same as the first exemplary embodiment.

FIG. 3 is a schematic diagram of the photoacoustic probe according to the present exemplary embodiment.

According to the present exemplary embodiment, it is characterized in that the flexible printed wiring 151 is directly connected to the back surface of the chip 120.

The chip where the capacitive transducer 103 is formed includes the through wiring 124. The wiring connected to the first and second electrodes 202 and 203 on the front surface of the chip (formation surface of the capacitive transducer) is drawn out to the electrode 126 on the back surface of the chip (surface on which the capacitive transducer is not formed). According to the present exemplary embodiment, the capacitive transducer 103 arranged on the chip is covered with an insulating film, and the wiring from the inside electrode is also drawn out to the back surface of the chip by the through wiring 124. For this reason, the electrode provided to the capacitive transducer 103 is completely insulated from the outside on the front surface of the chip. For this reason, it is possible to avoid a situation where the high voltage is applied to the subject while the electrode to which the high voltage is applied is put into a continuity state with the subject, and the safe capacitive transducer 103 can be provided.

Next, an electric connection part of the back surface of the chip 120 and the flexible printed wiring 151 will be described. A conductive layer 232 of the flexible printed wiring is exposed while corresponding to the position of the electrode of the back surface of the chip, and the electrodes of the chip and the flexible printed wiring are electrically connected to each other by anisotropic conductive resin 153. The anisotropic conductive resin 153 is an insulating thermo-hardening resin containing fine conductive metallic particles having a size of approximately several micrometers, and an anisotropic conductive film (ACF), an anisotropic conductive paste, or the like can be used. The anisotropic conductive resin 153 is hardened under heat in a state in which a distance between the electrode 126 on the chip 120 and an electrode 126 on the flexible part 151 is narrower than the fine metallic particles, and the solder bump 125 and the electrode 126 are electrically connected to each other by the anisotropic conductive resin 153. On the other hand, when the distance between the electrode on the plane of the chip 120 and the electrode on the flexible part 151 is wider than the fine metallic particles, the solder bump 125 and the electrode 126 are electrically insulated from each other because of the insulation property of the anisotropic conductive resin 153. With the presence of the anisotropic conductive resin 153, it is possible to reduce the influence of the defective generation onto the electric connection part because of moisture or the like, and an electric connection reliability can be increased. The flexible printed wiring 151 electrically connected on the back surface of the chip 120 is fixed onto the supporting member 140 via the adhesive 141.

According to the present exemplary embodiment, in a state in which the soft flexible printed wiring 151 is pressurized, the hard chip 120 is heated to harden the anisotropic conductive resin. For this reason, since the soft flexible printed wiring 151 is deformed along a shape of the back surface of the chip 120, the interval between the electrodes can be reliably set to lower than or equal to the size of the fine metallic particle. In addition, the electrodes are connected to each other by using the anisotropic conductive resin, and at the same time, the electric insulation between the electrode or wiring and the outside can be secured. According to a configuration in which the electric connection and insulation are separately performed, the underfill material to secure the insulation is separately injected, and it is necessary to perform hardening. When the underfill material injected to the back surface of the chip creeps up to a chip side surface and flows onto the transducer unit 103 of the front surface of the chip, the reception characteristic of the transducer unit 103 is significantly degraded. To avoid this situation, a large restriction is imposed in terms of manufacturing, which leads to a complex manufacturing process or a decrease in the yield. By using the present exemplary embodiment, the generation of the above-described degradation in the reception characteristic of the transducer unit 103 can be easily avoided.

When the present exemplary embodiment is used as described above, the electric connection between the electrodes is reliably performed, and also the insulation from the outside can be reliably realized, so that it is possible to provide the transducer unit 103 without the degradation in the reception characteristic.

Third Exemplary Embodiment

A third exemplary embodiment relates to a connection mode of the chip and the flexible printed wiring. The other aspects are the same as the second exemplary embodiment.

Figure 4B:
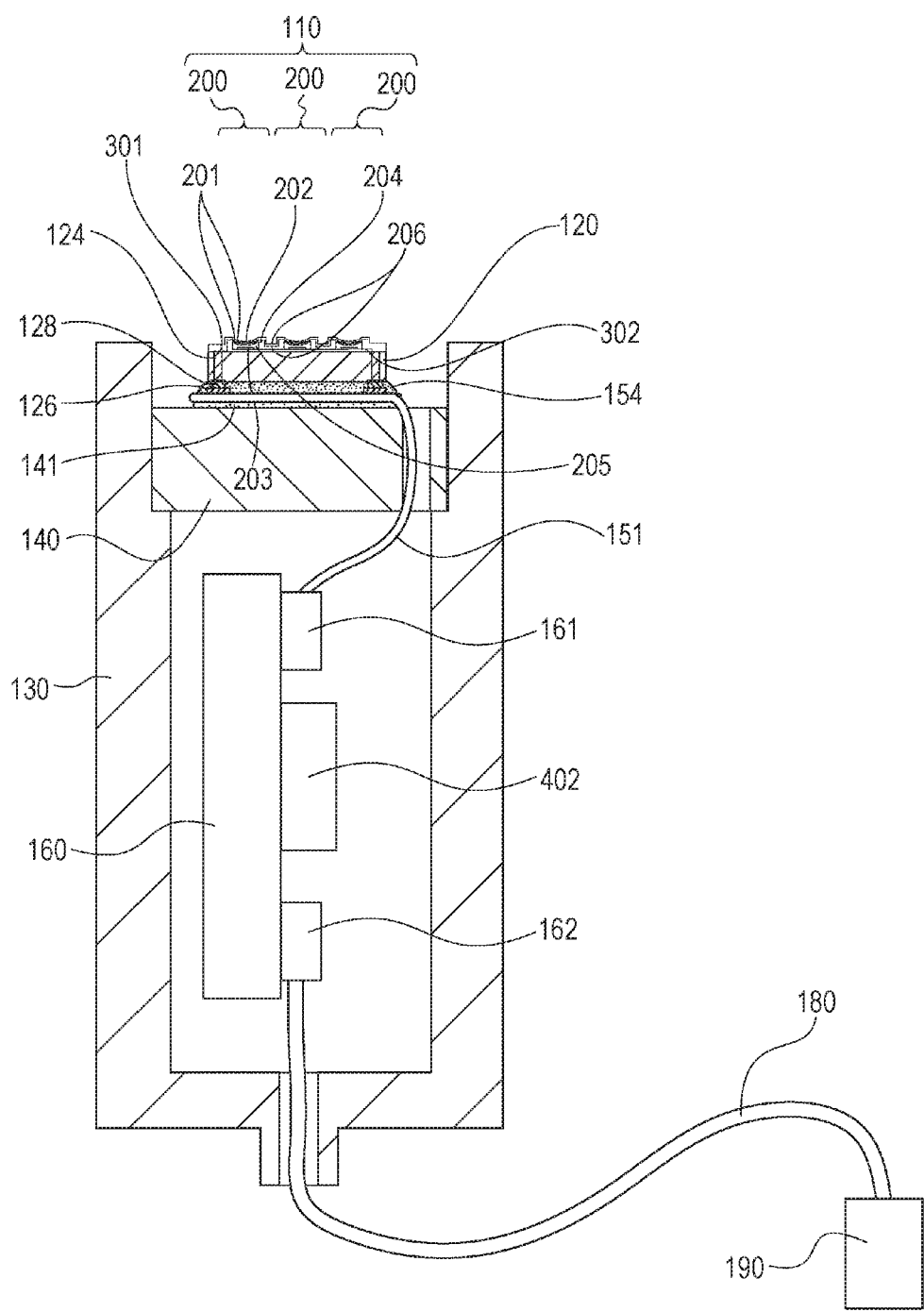

FIGS. 4A and 4B are schematic diagrams of the photoacoustic probe according to the present exemplary embodiment.

According to the present exemplary embodiment, as illustrated in FIG. 4A, it is characterized in that the flexible printed wirings are connected to each other by a solder bump 127 from the back surface of the chip 120 via the through wiring 124.

The chip 120 where the capacitive transducer is formed includes the through wiring 124. The wiring connected to the first and second electrodes 202 and 203 on the front surface of the chip (formation surface of the capacitive transducer) is drawn out to the electrode of the back surface of the chip (surface on which the capacitive transducer is not formed). The conductive layer of the flexible printed wiring is exposed while corresponding to the position of the electrode on the back surface of the chip (which is not illustrated in the drawing). The electrode on the chip and the electrode of the flexible printed wiring are electrically connected to each other by the solder bump 127. A space between the chip and the flexible printed wiring is filled with an underfill material 154. With the presence of the underfill material 154, it is possible to reduce the influence of the defective generation onto the electric connection part caused by moisture or the like, and the electric connection reliability can be increased.

According to the present exemplary embodiment, the chip and the flexible printed wiring 151 are electrically connected to each other by the solder bump 127, and it is possible to realize the electric connection with the high electric reliability by using the simple method.

As illustrated in FIG. 4B, a configuration can also be adopted in which a gold bump 128 is used to realize the connection instead of the solder bump 127 according to the present exemplary embodiment.

The flexible printed wiring 151 can be bent along the shape of the chip 120. Therefore, even in a case where a slight warp occurs in the chip 120, a connection failure at the electric connection part with a gold bump 213 hardly occurs while the flexible printed wiring 151 is deformed. For this reason, the gold bump 128 used in a flip chip mounting technology or a gold bump-solder can be used other than the solder bump 127, and the number of restrictions on the used bump can be decreased, so that it is possible to select an optimal electric connection method.

According to the present exemplary embodiment, it is possible to provide the photoacoustic probe in which the arrangement can be realized while the arrangement interval of the plurality of ultrasonic transducers is set to be narrow without using the solder bump.

Fourth Exemplary Embodiment

A fourth exemplary embodiment relates to a connection mode of the chip and the flexible printed wiring. The other aspects are the same as the first exemplary embodiment.

Figure 5A:
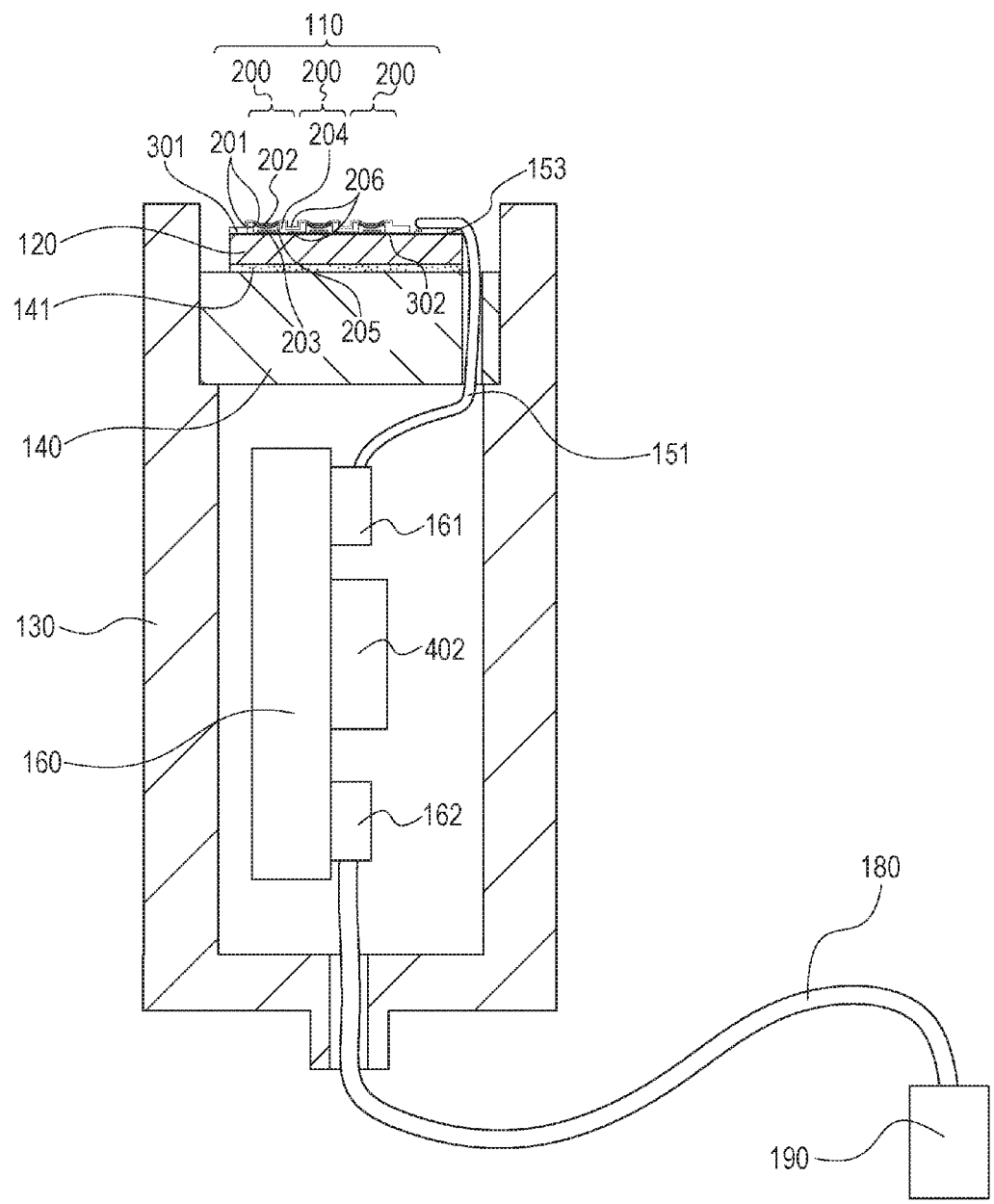
FIGS. 5A and 5B are schematic diagrams of the photoacoustic probe according to a fourth exemplary embodiment of the present invention.
Figure 5B:
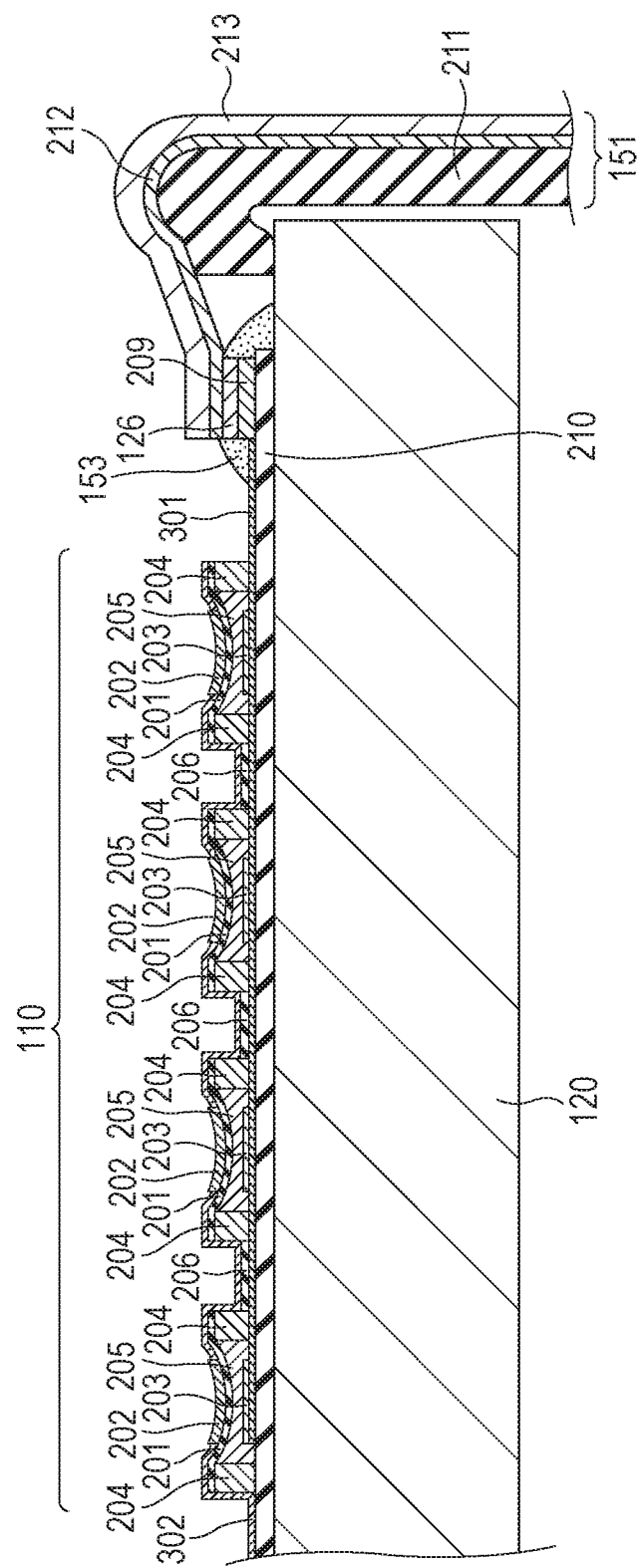

FIGS. 5A and 5B are schematic diagrams of the photoacoustic probe according to the present exemplary embodiment.

According to the present exemplary embodiment, it is characterized in that the electric connection with the detection circuit is performed by the flexible printed wiring arranged on the front surface of the chip.

The electrode 126 for the connection where a conductive layer 212 is exposed in which one surface is not covered with an insulating film 211 is provided at an end of the flexible printed wiring 151. An electrode 209 for the connection which is connected to the electrode of the transducer unit 103 is arranged on the chip 120. The electrode 126 for the connection of the flexible part 151 is arranged so as to face the electrode 209 for the connection on the chip 120. The electrode 209 for the connection and the electrode 126 for the connection are electrically connected to each other by the anisotropic conductive resin 153. The chip 120 and the flexible part 151 are mechanically fixed by the anisotropic conductive resin 153. According to the present exemplary embodiment, since the wiring is drawn out from the front surface of the chip by using the flexible printed wiring 151, it is possible to reduce the height of the wiring towards the subject side. For this reason, the influence affecting the reception characteristic of the transducer unit 103 from the wiring part can be reduced as much as possible.

According to the present exemplary embodiment, the flexible printed wiring 151 connected to the chip 120 is bent substantially in the perpendicular direction to the chip 120, and the first and second wirings 301 and 302 are drawn out to the perpendicular direction of the chip 120. For this reason, while the arrangement area with respect to the size of the chip 120 as viewed from the subject side is hardly expanded, the second wiring 302 from the transducer unit 103 can be connected to the detection circuit 402.

Fifth Exemplary Embodiment

A fifth exemplary embodiment relates to a member that supports the chip. The other aspects are the same as any one of the first to fourth exemplary embodiments.

Figure 6A:
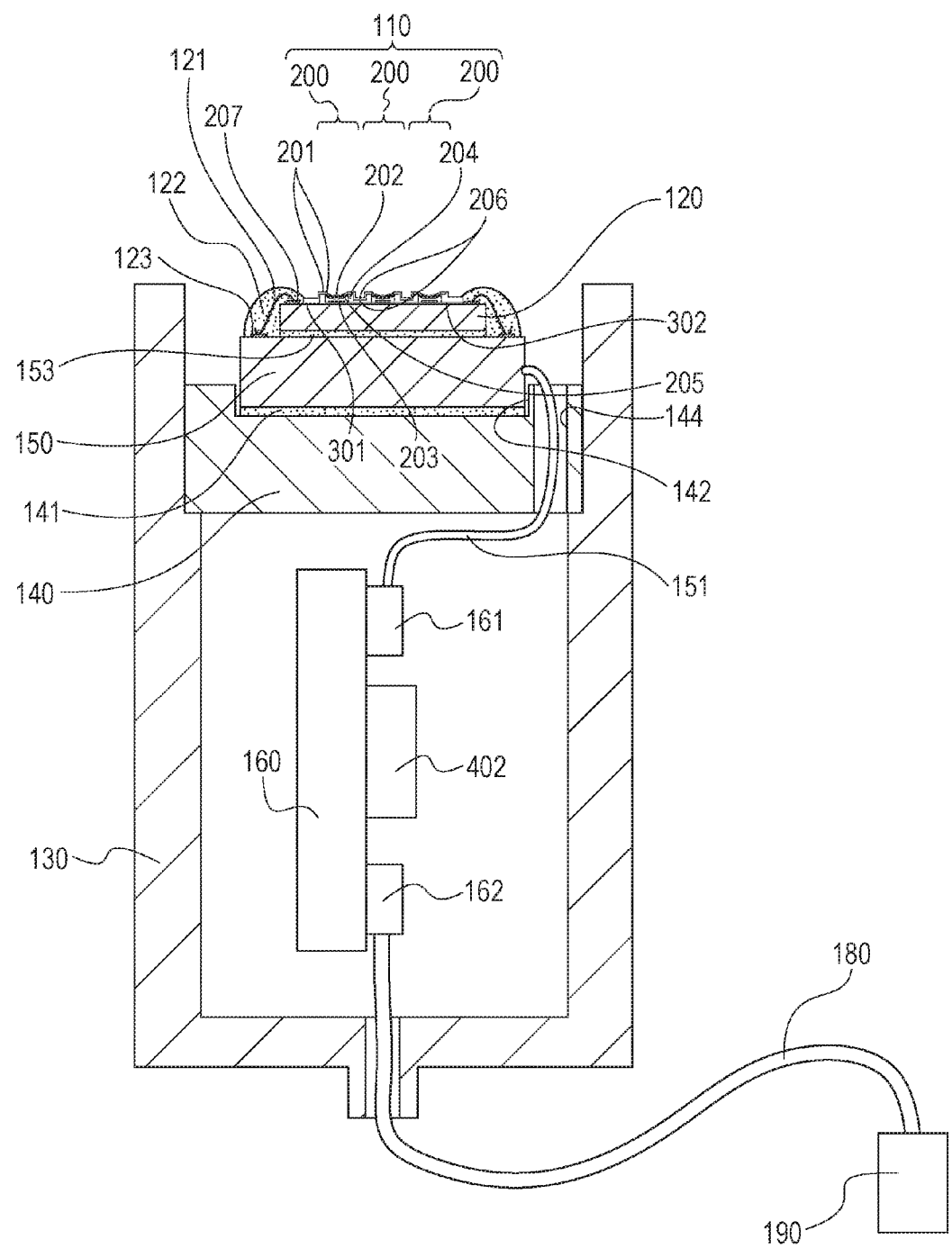

FIGS. 6A and 6B are schematic diagrams of the photoacoustic probe according to the present exemplary embodiment.

According to the present exemplary embodiment, as illustrated in FIG. 6A, it is characterized in that a base (supporting part) 140 that holds the chip 120 has a concave part 142. The concave part 142 of the base 140 has a shape corresponding to an outer circumference (outer shape) of the chip 120. The chip 120 provided with the CMUT 110 is arranged to the concave part 142 on the base 140 by bonding. The flexible printed wiring 151 connected to the chip 120 can pass through the through hole 144. Since the base 140 has the concave part 142, the position where the chip 120 is arranged can be arranged at a high accuracy.

According to the present exemplary embodiment, it is possible to provide the photoacoustic probe in which the position of the CMUT 110 is arranged at a high accuracy with respect to the transducer unit 103.

Another mode of the present exemplary embodiment will be described with reference to FIG. 6B. In FIG. 6B, it is characterized in a head member 131 corresponding to a member in which the base 140 and a leading edge of the casing 130 are integrated with each other. The head member 131 includes a concave part 143 and the through hole 144. The chip 120 is arranged to the concave part 143 which functions for positioning the chip 120. In addition, the flexible printed wiring 151 connected to the chip 120 can pass through the through hole 144. The flexible printed wiring 151 is drawn out to the rear side of the head member 131 (opposite surface side to the arrangement of the chip 120) to be connected to the circuit substrate 160.

According to another mode of the present exemplary embodiment, a leading edge of the transducer unit 103 is constituted by a single integrated member. For this reason, the leading edge of the transducer unit 103 can be set to have a minimum size with respect to the chip 120, and the CMUTs 110 can be arranged to be in closer proximity to one another.

In addition, since the casing of the leading edge of the transducer unit 103 and the base that holds the chip are integrated with each other, it is possible to arrange the chip 120 at a still higher accuracy with respect to an outer shape of the transducer unit 103.

Sixth Exemplary Embodiment

A sixth exemplary embodiment relates to a configuration of the flexible printed wiring that connects the chip to the circuit substrate. The other aspects are the same as any one of the first to fifth exemplary embodiments.

Figure 7:
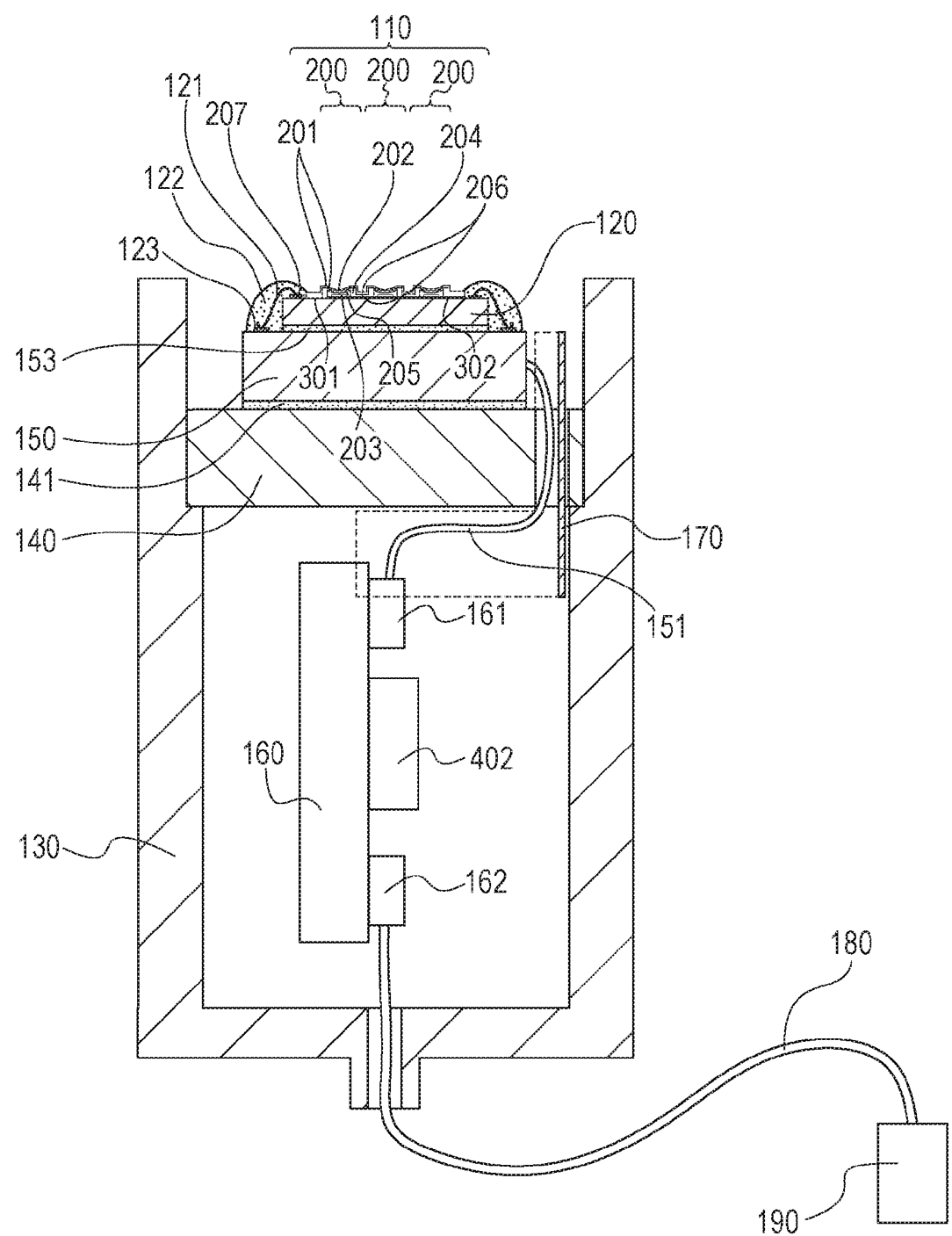
FIG. 7 is a schematic diagram of the photoacoustic probe according to a sixth exemplary embodiment of the present invention.

FIG. 7 is a schematic diagram of the photoacoustic probe according to the present exemplary embodiment. According to the present exemplary embodiment, the transducer unit has a configuration including an electrostatic shield. Specifically, it is characterized in that the flexible printed wiring 151 is covered with an electrostatic shield 170. Although omitted in FIG. 7, the electrostatic shield 170 is connected to a potential such as a ground of the detection circuit. In addition, the electrostatic shield 170 may have an integrated configuration while being affixed to the flexible printed wiring 151.

The supporting member 101 according to the present exemplary embodiment is preferably made of a metal for a purpose of securing a mechanical strength and a purpose of securing a process accuracy of the through hole 102. However, in the CMUT 110, if a member having a potential is in proximity to the second wiring 302 between the first electrode 202 and the detection circuit 402, the potential of the member is superimposed on the detection signal as the noise. When the ultrasonic transducers 110 are arranged to be in proximity to one another to have a small diameter, the flexible printed wiring 160 has a substantially narrow distance with a side surface of the through hole 102 of the supporting member 101. Since the supporting member 101 made of the metal has a large surface area, the supporting member 101 inevitably has a certain potential while being affected by an influence of a surrounding apparatus or the like. For this reason, when the ultrasonic transducer 110 are arranged in proximity to one another, the noise superimposed on the flexible printed wiring 151 significantly affects the reception characteristic of the transducer from the potential of the supporting member 101.

According to the present exemplary embodiment, since the flexible printed wiring 151 is shielded by the electrostatic shield 170 between the flexible printed wiring 151 and the supporting member 101, even when the ultrasonic transducers 110 are arranged in proximity to one another, it is possible to provide the photoacoustic probe in which the degradation in the reception characteristic is small.

Seventh Exemplary Embodiment

A seventh exemplary embodiment relates to a configuration of the flexible printed wiring that connects the chip with the circuit substrate. The other aspects are the same as any one of the first to sixth exemplary embodiments.

Figure 8A:
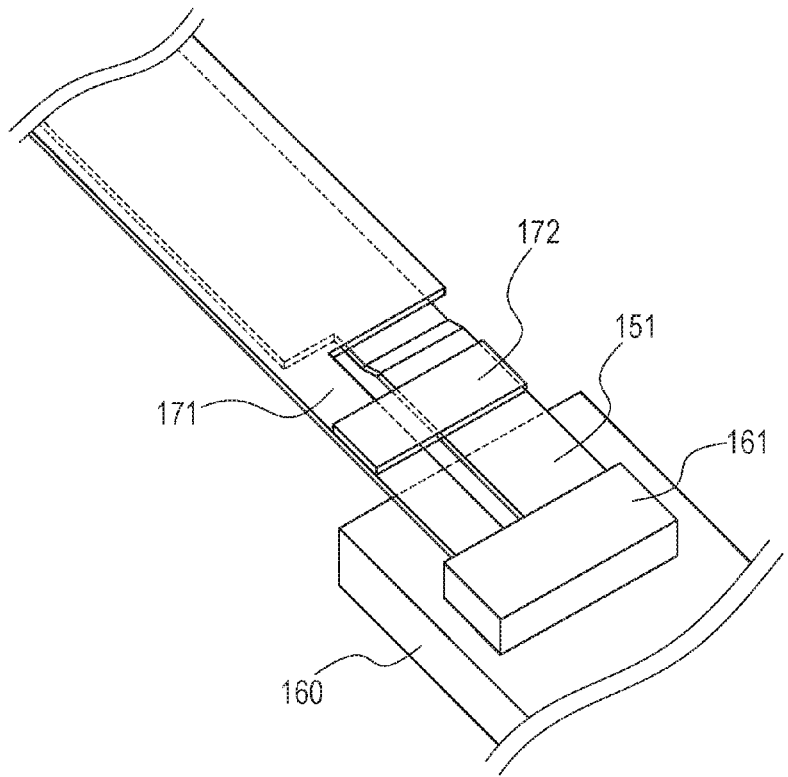
FIGS. 8A and 8B are schematic diagrams of the photoacoustic probe according to a seventh exemplary embodiment of the present invention.
Figure 8B:
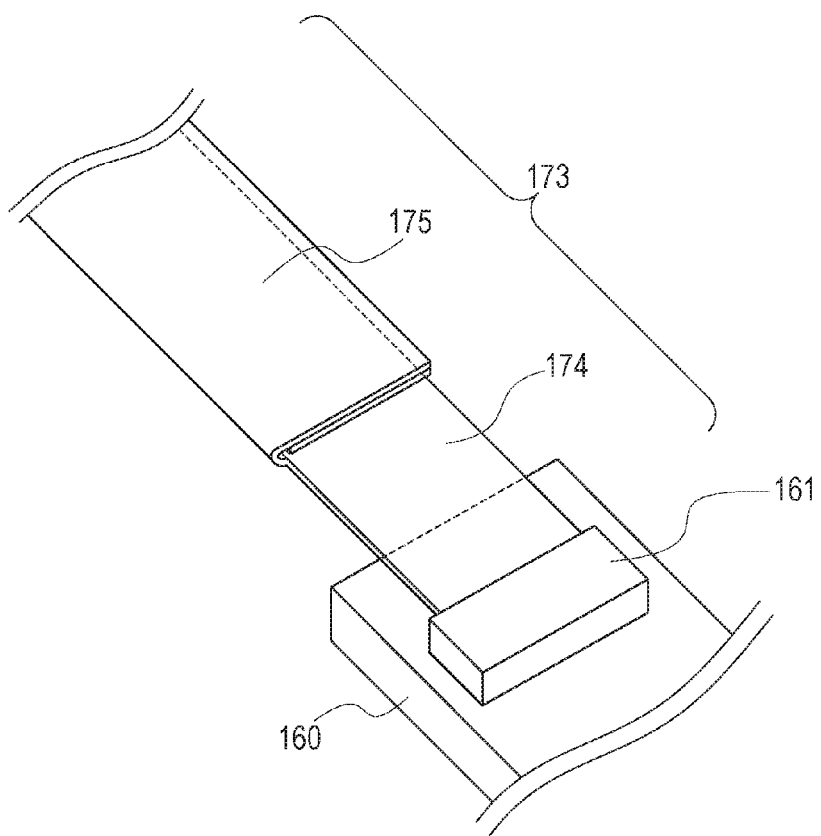

FIGS. 8A and 8B are schematic diagrams of the photoacoustic probe according to the present exemplary embodiment.

FIG. 8A is an expanded view of a connection part of the flexible printed wiring 151 and the circuit substrate 160 according to the present exemplary embodiment. According to the present exemplary embodiment, as illustrated in FIG. 8A, it is characterized in that an electrostatic shield 171 is integrated to the flexible printed wiring 151. In the flexible printed wiring 151 according to the present exemplary embodiment, the electrostatic shield 171 having the same shape is bonded and fixed to a fixing member 172 by adhesive. The electrostatic shield 171 is constituted by the same creating method to have the same cross section as the flexible printed wiring and has a shape to be overlapped with the flexible printed wiring 151. For this reason, the electrostatic shield 171 according to the present exemplary embodiment can be bent along the flexible printed wiring 151.

The electrostatic shield 171 has a mode in which an internal conductive layer does not have a pattern, and the flexible printed wiring 151 is covered with the conductive layer. Since the electrostatic shield 171 according to the present exemplary embodiment is bonded and integrated with the flexible printed wiring 151, it is not necessary to perform positioning of the flexible printed wiring 151 and the electrostatic shield 171.

In addition, the flexible printed wiring 151 and the end of the electrostatic shield 171 are electrically connected to the wiring in the circuit substrate 160 by the flexible printed wiring connector 161 of the circuit substrate 160 according to the present exemplary embodiment. A potential of the conductive layer of the electrostatic shield 171 is connected to a reference potential GND of the detection circuit in the circuit substrate 160.

According to the present exemplary embodiment, since it is not necessary to separately provide the electrostatic shield, the transducer unit 103 and the supporting member 101 can be shielded from each other by the electrostatic shield 171 without increasing the size of the leading edge of the transducer unit 103. For this reason, even when the ultrasonic transducers 110 are arranged in proximity to one another, it is possible to provide the small-sized photoacoustic probe in which the degradation in the reception characteristic is small.

Another mode of the present exemplary embodiment will be described with reference to FIG. 8B. According to this another mode, it is characterized in that the flexible printed wiring 151 and the electrostatic shield part 171 are constituted by the same flexible printed wiring 173. Specifically, a configuration is adopted in which an electrostatic shield part 175 is folded to be bonded with a flexible printed wiring part 174.

According to another mode of the present exemplary embodiment, since the flexible printed wiring part 174 and the electrostatic shield part 175 are formed from the same flexible printed wiring 173, the number of components can be decreased. In addition, the electric connection with the circuit substrate 160 can be reliably performed.

Eighth Exemplary Embodiment

An eighth exemplary embodiment relates to a connection part of the flexible printed wiring. The other aspects are the same as any one of the first to seventh exemplary embodiments.

Figure 9A:
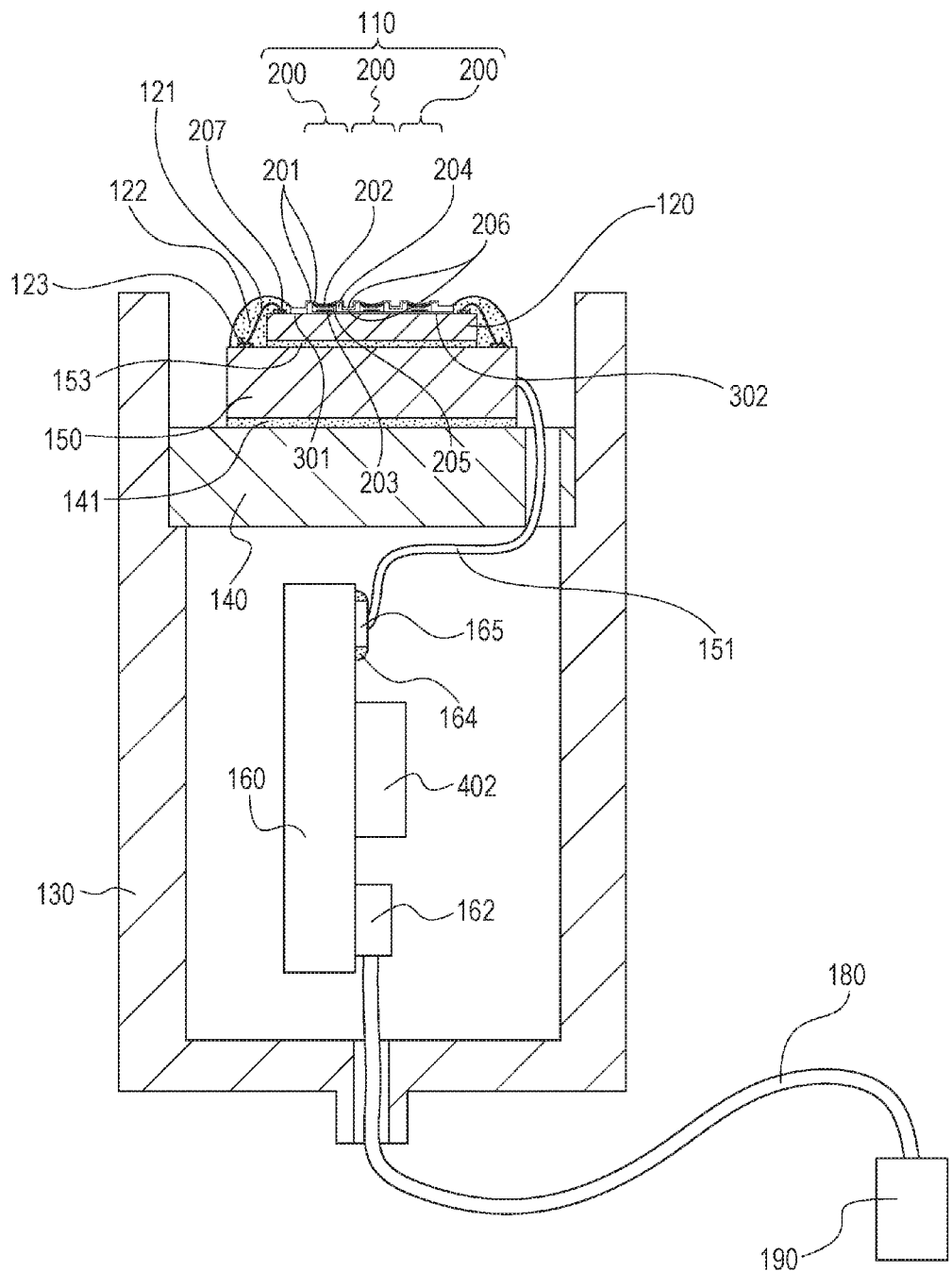
Figure 9C:
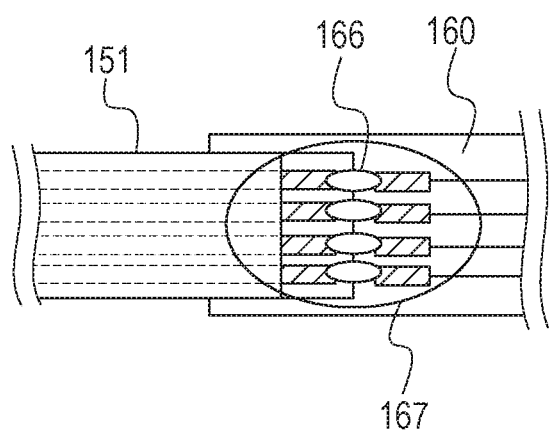

FIGS. 9A to 9C are schematic diagrams of the photoacoustic probe according to the present exemplary embodiment.

According to the present exemplary embodiment, as illustrated in FIG. 9A, it is characterized in that the flexible printed wiring 151 and the circuit substrate 160 are electrically connected to each other by the anisotropic conductive resin. Since it is necessary to apply a DC voltage corresponding to a high voltage from a several tens of bolts to a several hundreds of bolts to the capacitive transducer 110, a high voltage needs to be applied to the flexible printed wiring 151. For this reason, the flexible printed wiring connector 161 needs to have a wide electrode interval to secure a breakdown voltage, and it is difficult to realize the miniaturization. For this reason, it is difficult to narrow the width of the circuit substrate 160, which becomes a restriction when the ultrasonic transducers 110 are arranged to be proximity to one another.

According to the present exemplary embodiment, the flexible printed wiring 151 and the circuit substrate 160 are electrically connected to each other by the anisotropic conductive resin 164. At the same time, the electric insulation between the adjacent electrodes is secured by the anisotropic conductive resin 164. For this reason, with the presence of the anisotropic conductive resin of the insulating resin, the interval between the adjacent electrodes can be significantly narrowed by the flexible printed wiring connector 161 using the exposed terminal. For this reason, according to the present exemplary embodiment, the width of the circuit substrate 160 can be narrowed, and it is possible to provide the photoacoustic probe in which the ultrasonic transducers 110 can be arranged in proximity to one another. In addition, a height of the electric connection part of the flexible printed wiring 151 and the circuit substrate 160 can be decreased to almost a level of a thickness of the flexible printed wiring 151. For this reason, it becomes easier to decrease the diameter of the ultrasonic transducer 110.

According to the present exemplary embodiment, the circuit substrates 160 of the flexible printed wiring 151 are electrically connected to each other by the anisotropic conductive resin, but the present invention is not limited to this configuration. A configuration can be adopted in which solder particles are dispersed in the resin, and heat is applied, so that the solder concentrates between the electrodes to realize soldering connection. In addition, the flexible printed wiring and the circuit substrate can be connected to each other by soldering. Specifically, as illustrated in FIGS. 9B and 9C, a configuration in which the electrodes are arranged upward while being shifted to each other, and the electrodes are bridged by soldering 166 to be surrounded by a sealing material 168, or the like can be used similarly. By using these components, it is possible to obtain the electric connection part having a high reliability.

Ninth Exemplary Embodiment

A ninth exemplary embodiment relates to a configuration of the flexible printed wiring that connects the chip with the circuit substrate. The other aspects are the same as any one of the first to eighth exemplary embodiments.

Figure 10:
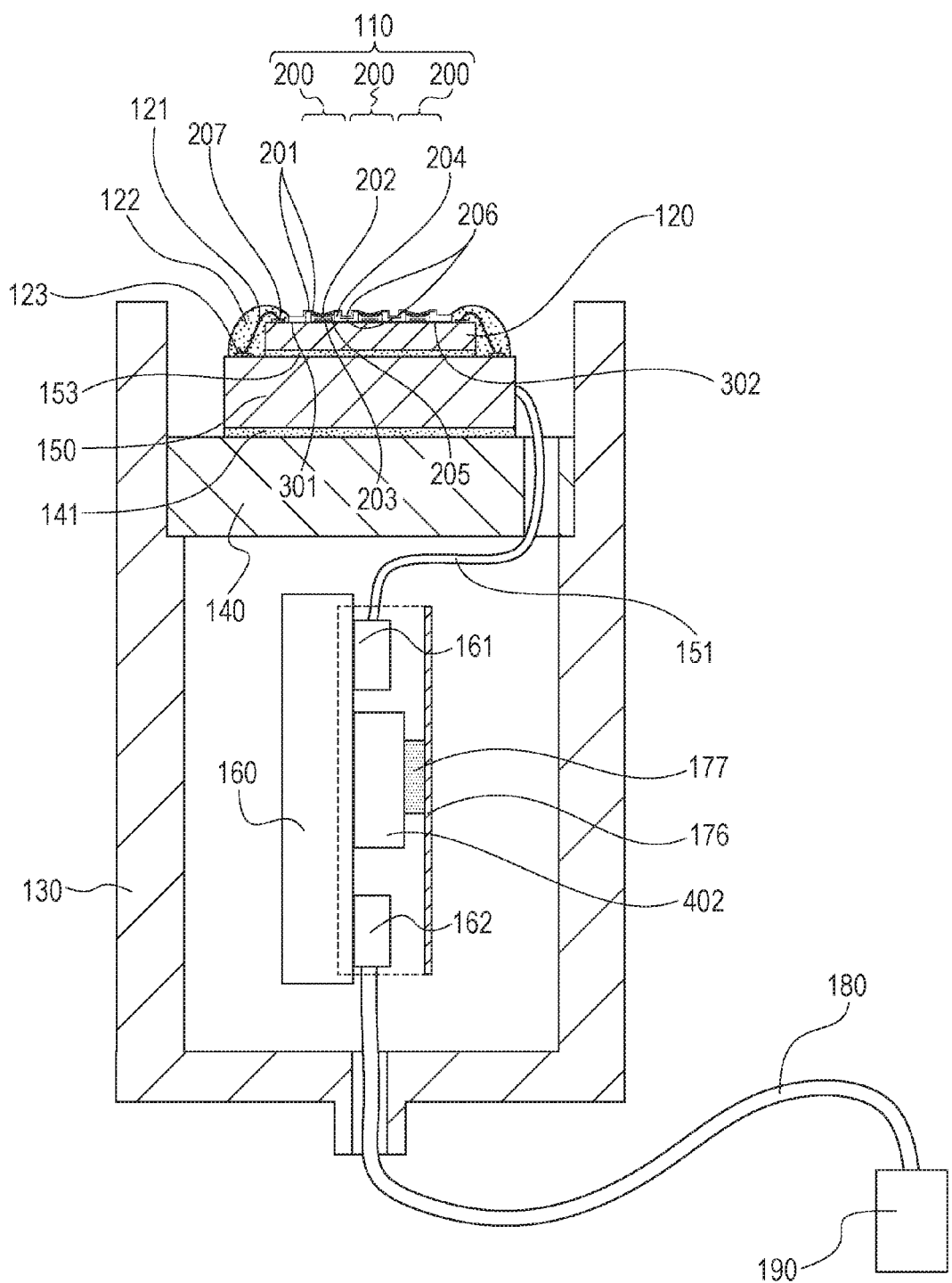
FIG. 10 is a schematic diagram of the photoacoustic probe according to a ninth exemplary embodiment of the present invention.

FIG. 10 is a schematic diagram of the photoacoustic probe according to the present exemplary embodiment.

According to the present exemplary embodiment, it is characterized in that the detection circuit 402 on the circuit substrate 160 is covered by a shield cover 176. The detection circuit 402 and the shield cover are electrically connected by soldering and also fixed. In addition, a radiating sheet 177 is arranged between the detection circuit 402 and the shield cover 176.

According to the present exemplary embodiment, since the detection circuit 402 is covered with radiating sheet 177, the influence from the potential of the supporting member at the time of the current/voltage conversion is hardly affected, and the excellent reception characteristic can be arranged. For this reason, even when the ultrasonic transducers 110 are arranged in proximity to one another, it is possible to provide the small-sized photoacoustic probe in which the degradation in the reception characteristic is small.

In addition, since the detection circuit 402 is thermally connected to the shield cover 176 via the radiating sheet 177, the heat generated in the detection circuit 402 can be transmitted to the shield cover 176. Since the surface area occupied by the shield cover 176 is large with respect to the surface area occupied by the detection circuit 402, it is possible to improve a radiation characteristic of the transducer unit 103. For this reason, even in a case where the miniaturization of the transducer unit 103 is performed, it is possible to suppress the temperature increase of the transducer unit 103. Thus, the influence to the reception characteristic of the detection circuit 402 caused by the heat generation at the time of the miniaturization can be reduced.

Tenth Exemplary Embodiment

A tenth exemplary embodiment relates to configurations of the circuit substrate and the shield. The other aspects are the same as any one of the first to ninth exemplary embodiments.

Figure 11A:
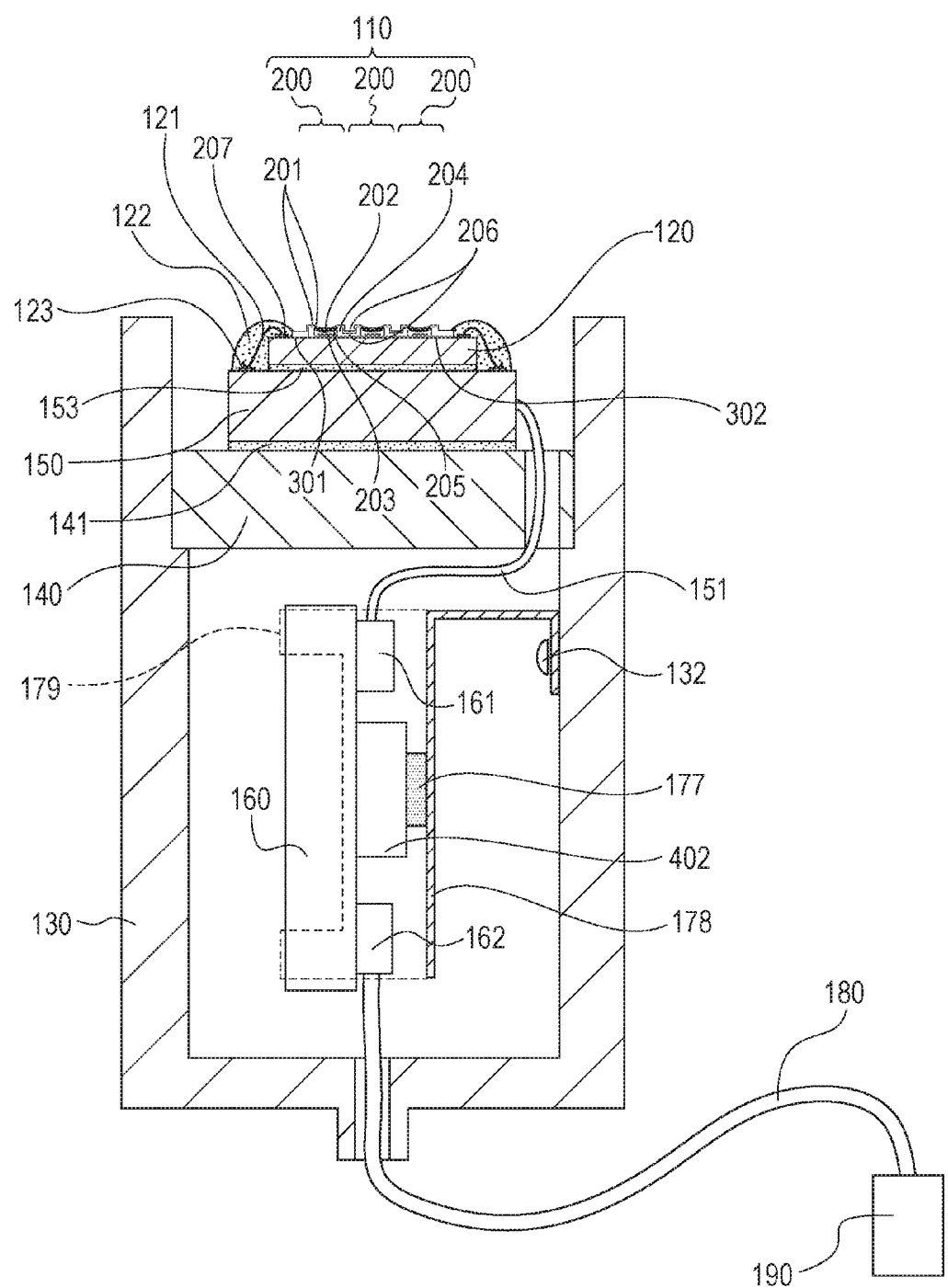
FIGS. 11A and 11B are schematic diagrams of the photoacoustic probe according to a tenth exemplary embodiment of the present invention.
Figure 11B:
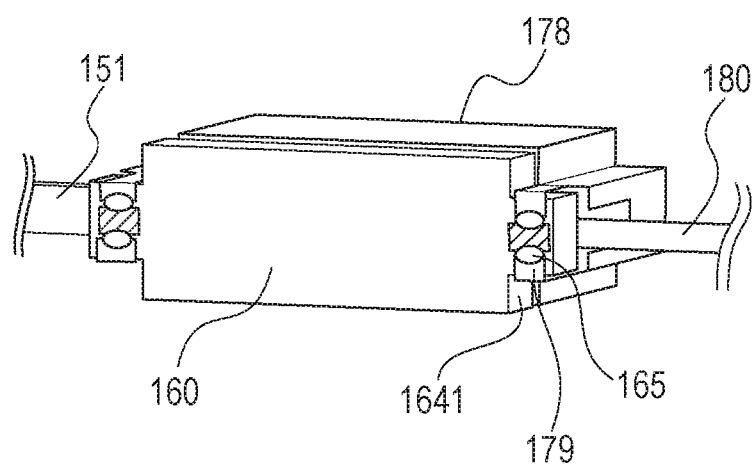

FIGS. 11A and 11B are schematic diagrams of the photoacoustic probe according to the present exemplary embodiment. FIG. 11A is a schematic diagram of a cross section of the transducer unit, and FIG. 11B is a schematic diagram of the circuit substrate 160 as viewed from the rear side.

According to the present exemplary embodiment, the circuit substrate 160 includes a concave part 1641 at each of four corners. In addition a shield 178 has a protrusion 179 corresponding to the concave part, and the protrusion 179 is bent. The circuit substrate 160 is fixed by the shield 178 by soldering. The shield 178 is fixed to the casing 130 by a screw 132, and the circuit substrate 160 is fixed to the casing 130 by the shield 178.

According to the present exemplary embodiment, since the circuit substrate 160 can determined the position at a high accuracy with respect to the casing 130 of the transducer unit, the size of the transducer unit 103 can be reduced.

The circuit substrate 160 is fixed to the casing 130 via the shield 178. For this reason, while the circuit substrate 160 moves by way of vibration or the like, load on the flexible printed wiring 151 or the cable 180 connected to the circuit substrate 160 can be avoided. For this reason, even when the interval between the circuit substrate 160 and the casing 130 is narrowed, it is possible to provide the small-sized transducer unit having the high electric connection reliability.

Eleventh Exemplary Embodiment

An eleventh exemplary embodiment relates to the electric connection part of the circuit substrate and the cable. The other aspects are the same as any one of the first to tenth exemplary embodiments.

Figure 12A:
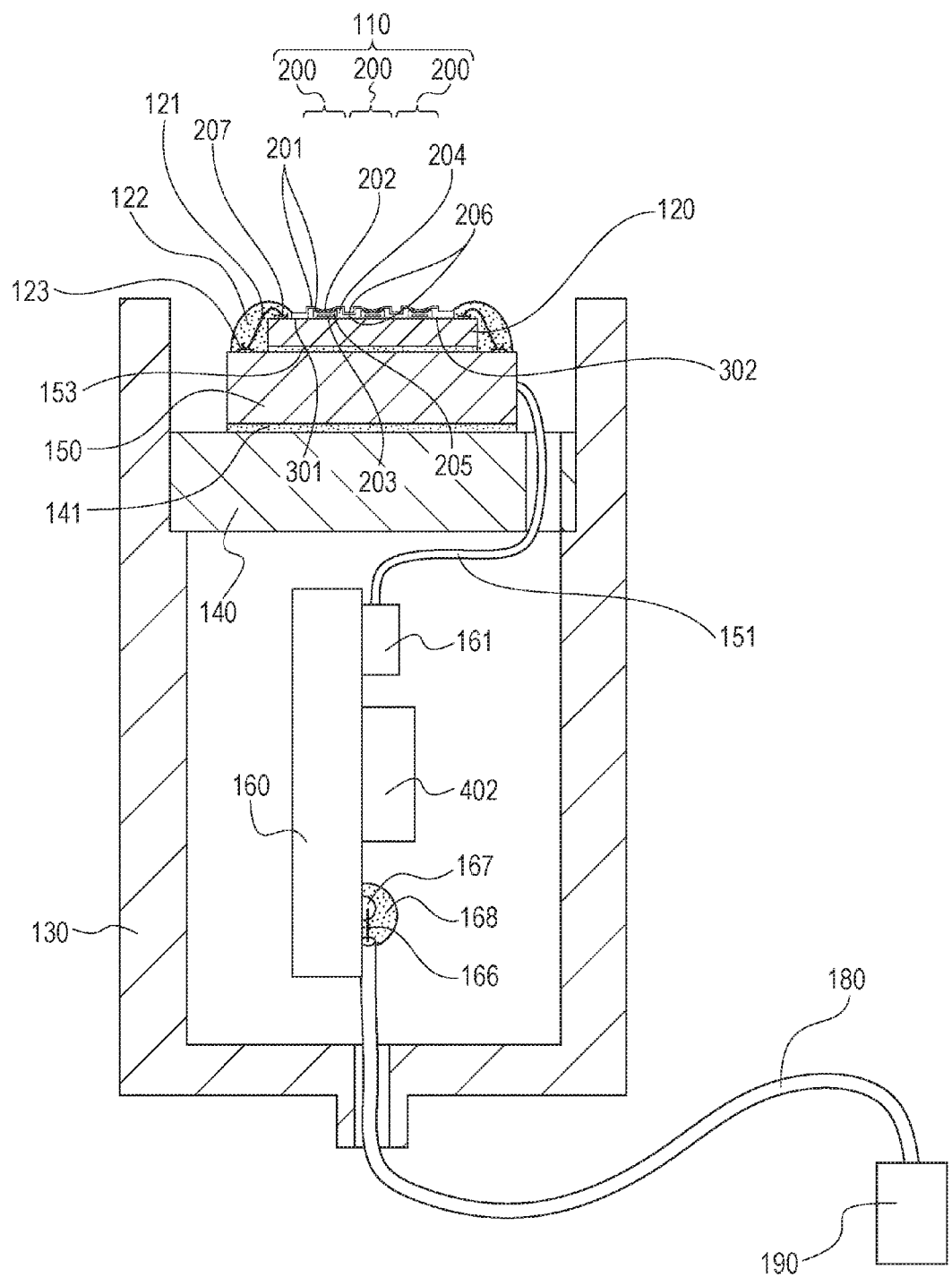
FIGS. 12A and 12B are schematic diagrams of the photoacoustic probe according to an eleventh exemplary embodiment of the present invention.
Figure 12B:
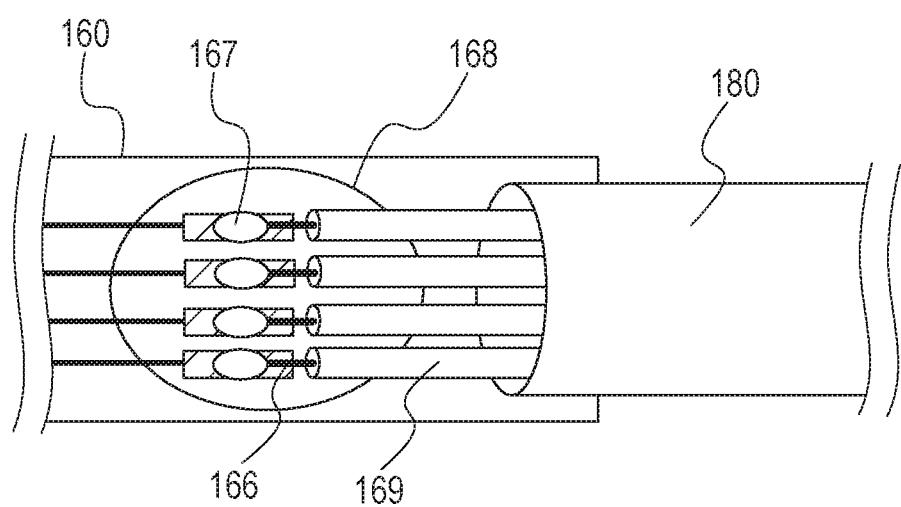

FIGS. 12A and 12B are schematic diagrams of the photoacoustic probe according to the present exemplary embodiment.

According to the present exemplary embodiment, the circuit substrate 160 and the cable 180 for the connection with the external apparatus (not illustrated) are connected to each other while is connected with the electrode on the circuit substrate 160 the cable 180 directly by soldering 167. A connection part of the solder is covered by the sealing material 168, and insulation from the outside is maintained.

Since it is necessary to apply a DC voltage corresponding to a high voltage from a several tens of bolts to a several hundreds of bolts to the CMUT 110, the high voltage needs to be applied to the circuit substrate 160 from the cable 180. For this reason, the connector 162 for the cable 180 needs to have a wide electrode interval to secure a breakdown voltage, and it is difficult to realize the miniaturization. For this reason, it is difficult to narrow the width of the circuit substrate 160, which becomes a restriction when the ultrasonic transducers 110 are arranged to be proximity to one another.

According to the present exemplary embodiment, it is not necessary to use the connector 162 for the connection between the circuit substrate 160 and the cable 180. For this reason, it is possible to significantly narrow the interval between the adjacent electrodes by the connector 162 using the exposed terminal. For this reason, according to the present exemplary embodiment, the width of the circuit substrate 160 can be narrowed, and it is possible to provide the photoacoustic probe in which the ultrasonic transducers 110 can be arranged in proximity to one another. Twelfth exemplary embodiment A twelfth exemplary embodiment relates to an electric connection part of the circuit substrate 160 and the cable 180. The other aspects are the same as any one of the first to tenth exemplary embodiments.

Figure 13A:
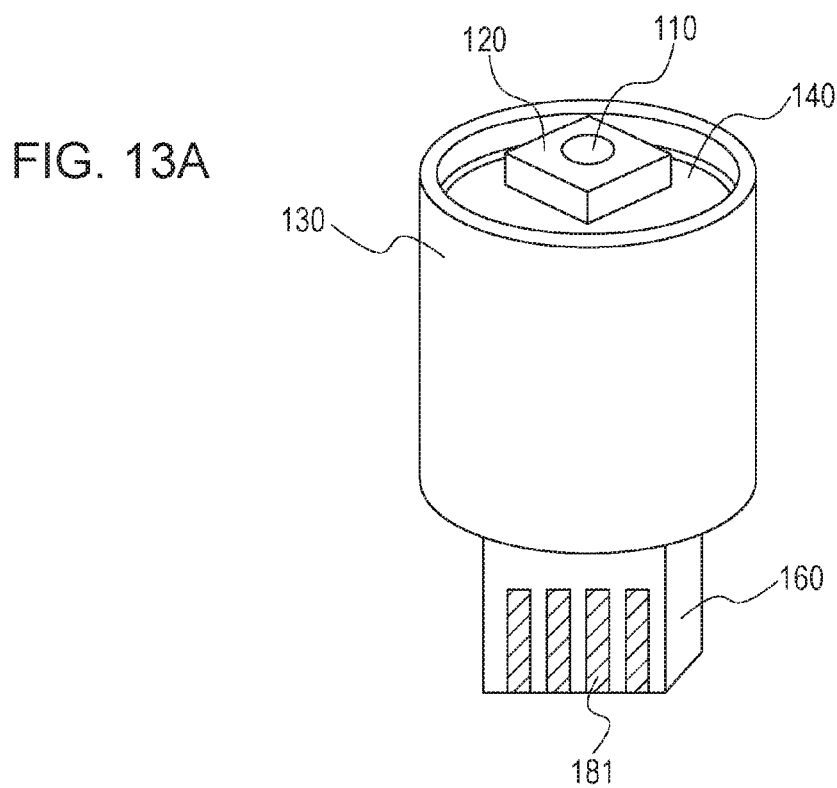
FIGS. 13A and 13B are schematic diagrams of the photoacoustic probe according to a twelfth exemplary embodiment of the present invention.
Figure 13B:
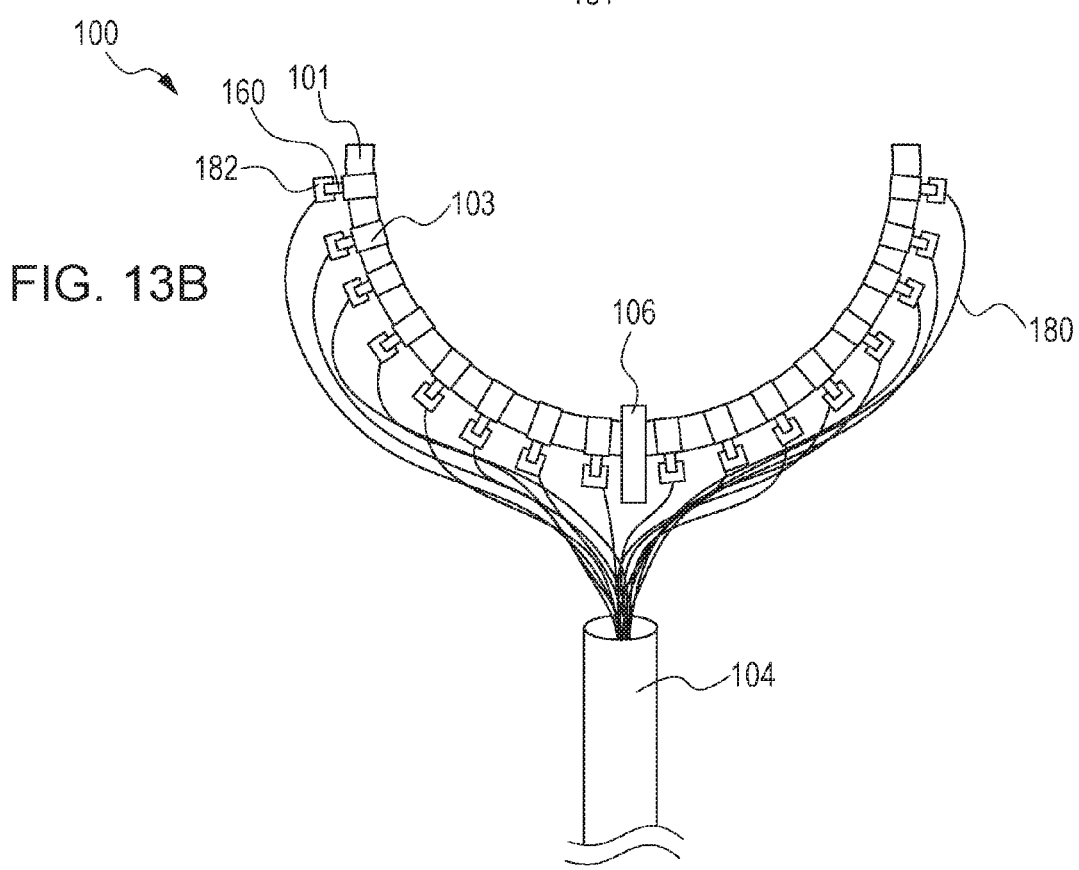

FIGS. 13A and 13B are schematic diagrams of the photoacoustic probe according to the present exemplary embodiment.

According to the present exemplary embodiment, it is characterized in that part of the circuit substrate 160 is exposed from the casing 130. Specifically, an electrode 192 is formed on the circuit substrate 160 that is exposed to the outside of the casing 130. A card-edge connector 193 is connected to the electrode 192 on the circuit substrate 160. Each of the ultrasonic probe transducer units 103 and the card-edge connector 193 are connected to each other by a wiring 191. According to the present exemplary embodiment, a configuration can be adopted in which the card-edge connector 193 is connected to the circuit substrate 160, and the circuit substrate 160 is connected to the external apparatus by the cable 180 connected to the card-edge connector 193.

According to the present exemplary embodiment, since the ultrasonic probe transducer unit 103 and the wiring to the unit can be easily detached and attached, it is possible to provide the photoacoustic probe having a high maintenance property.

Thirteenth Exemplary Embodiment

A thirteenth exemplary embodiment relates to a shape of a casing. The other aspects are the same as any one of the first to twelfth exemplary embodiments.

Figure 14:
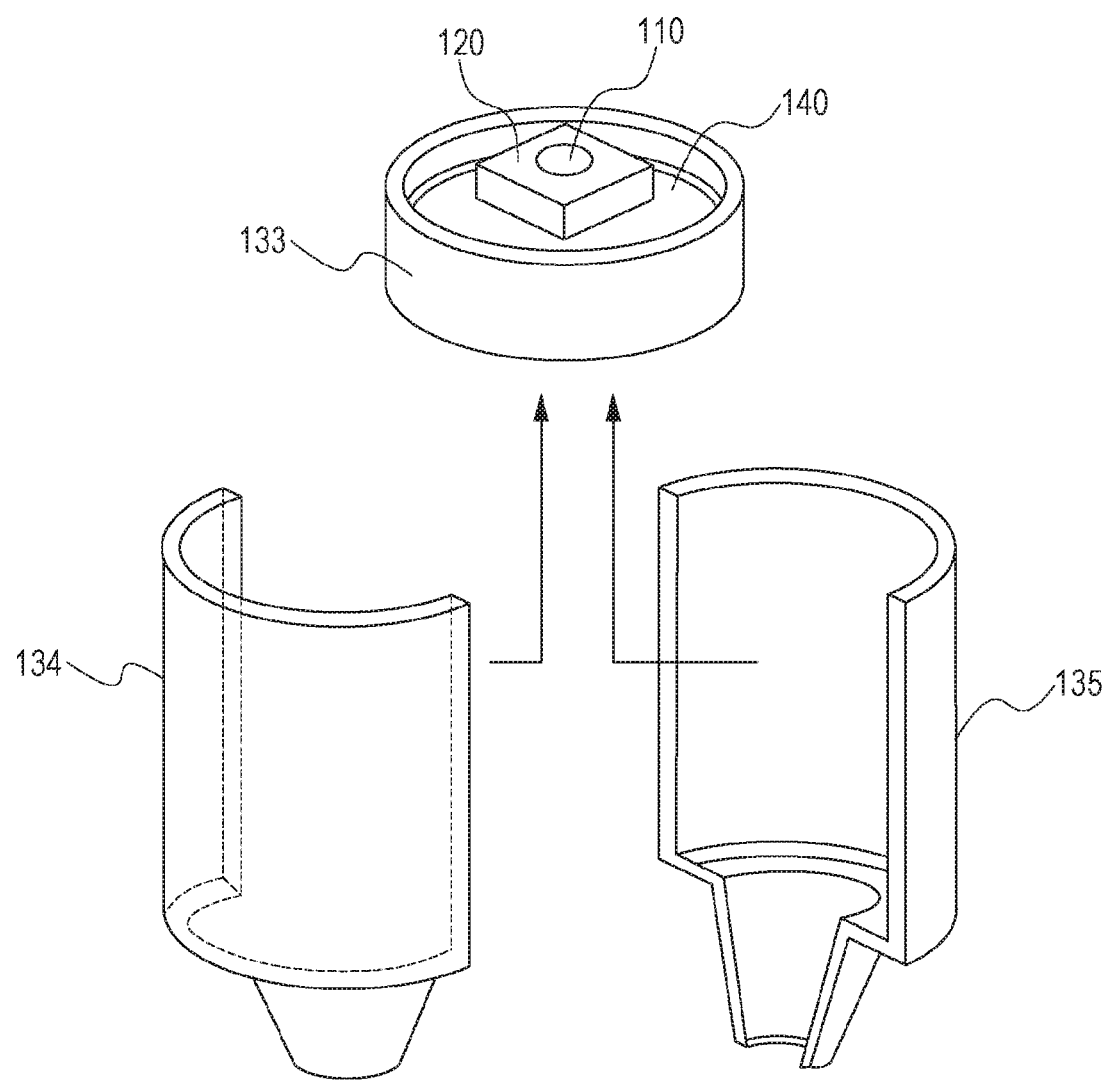
FIG. 14 is a schematic diagram of the photoacoustic probe according to a thirteenth exemplary embodiment of the present invention.

FIG. 14 is a schematic diagram of the photoacoustic probe according to the present exemplary embodiment.

According to the present exemplary embodiment, it is characterized in that the casing 130 is constituted by total three parts including two parts composed of a first casing cover 134 and a second casing cover 135 which are provided so as to sandwich the above-described circuit substrate and a unit leading edge part 133. It should be noted that the flexible printed wiring 151, the circuit substrate 160, and the cable 180 are omitted in FIG. 14.

According to the configuration of the present exemplary embodiment, the unit leading edge part 133 including the chip 120 and the casing cover part including the circuit substrate 160 and the cable 180 are constituted by separate members. For this reason, since only a non-defective product of the unit leading edge part 133 to which the chip 120 is mounted can be selected to be used for the assembly of the transducer unit, it is possible to decrease a rejection rate.

An operation of fixing the circuit substrate 160 and the cable 180 to the first casing cover by bonding or the like after the first casing cover 134 is attached to the unit leading edge part 133 is facilitated. In addition, when the bonding is performed, a bonding part can be widely secured, so that it is possible to perform he bonding having a high reliability. Thereafter, by fixing the second casing cover 135 to the unit leading edge part 133 and the first casing cover 134 by bonding or the like, it is possible to realize the highly reliable transducer unit by a simple process.

Furthermore, according to the transducer of the present exemplary embodiment, the casing cover is configured to be divided. Thus, a configuration can be realized in which an internal shape of the casing cover corresponds to the shape of the flexible printed wiring 151, the circuit substrate 160, or the cable 180. For this reason, the diameter of the casing cover can be decreased, and it is possible to provide the even smaller ultrasonic transducer. Fourteenth exemplary embodiment A fourteenth exemplary embodiment relates to a shape of the casing. The other aspects are the same as any one of the first to twelfth exemplary embodiments.

Figure 15:
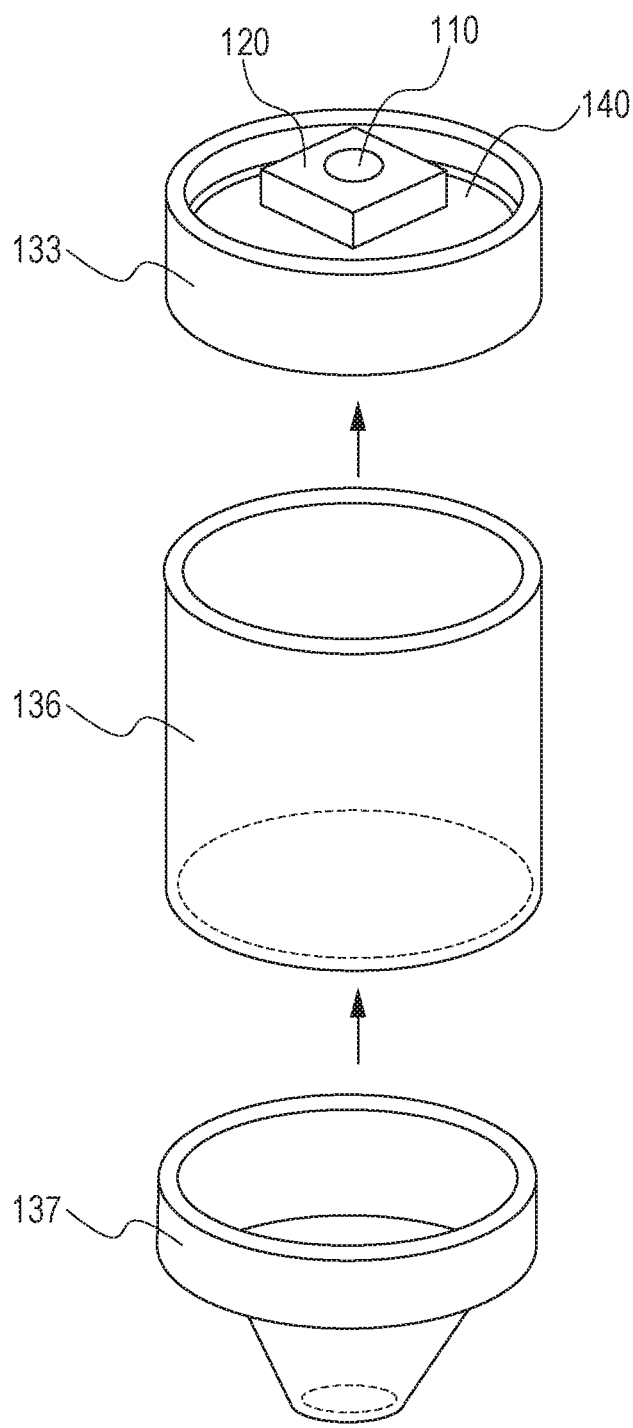
FIG. 15 is a schematic diagram of the photoacoustic probe according to a fourteenth exemplary embodiment of the present invention.

FIG. 15 is a schematic diagram of the photoacoustic probe according to the present exemplary embodiment.

According to the present exemplary embodiment, it is characterized in that the casing 130 is constituted by three parts including a unit leading edge part 133, a casing cover 136, and a cap 137. It should be noted that the flexible printed wiring 151, the circuit substrate 160, and the cable 180 are omitted in FIG. 15.

According to the configuration of the present exemplary embodiment, the unit leading edge part 133 and the casing cover part provided to the chip 120 are constituted separately. For this reason, only the non-defective product of the unit leading edge part 133 to which the chip 120 is mounted can be selected to be used for the assembly of the transducer unit, so that it is possible to decrease the rejection rate.

In the configuration according to the present exemplary embodiment, since the assembly is realized by only inserting the casing cover 136 in a state in which the circuit substrate 160 and the cable 180 are connected to the unit leading edge part 133 including the chip 120, it is possible to decrease the number of assembling processes. In addition, when potting is performed into the casing of the transducer unit, a potting material can be injected in a manner that the chip 120 surface is faced downward, and the potting material is injected into the inside of the tubular casing cover 136. Since the cap 137 is also provided, even when the load is applied to the cable 180 from the outside, the electric connection part with the circuit substrate 160 is not affected, and it is possible to provide the transducer unit with the high electric reliability.

Furthermore, according to the present exemplary embodiment, the configuration is adopted in which the tubular casing cover 136 is used, and a mechanical strength of the casing is high. Therefore, even when the diameter of the transducer unit is decreased, it is possible to provide the transducer unit having the high strength and the high reliability.

Fifteenth Exemplary Embodiment

The present exemplary embodiment relates to a member arranged on the front surface of the CMUT 110. The other aspects are the same as any one of the first to third exemplary embodiments.

Figure 16:
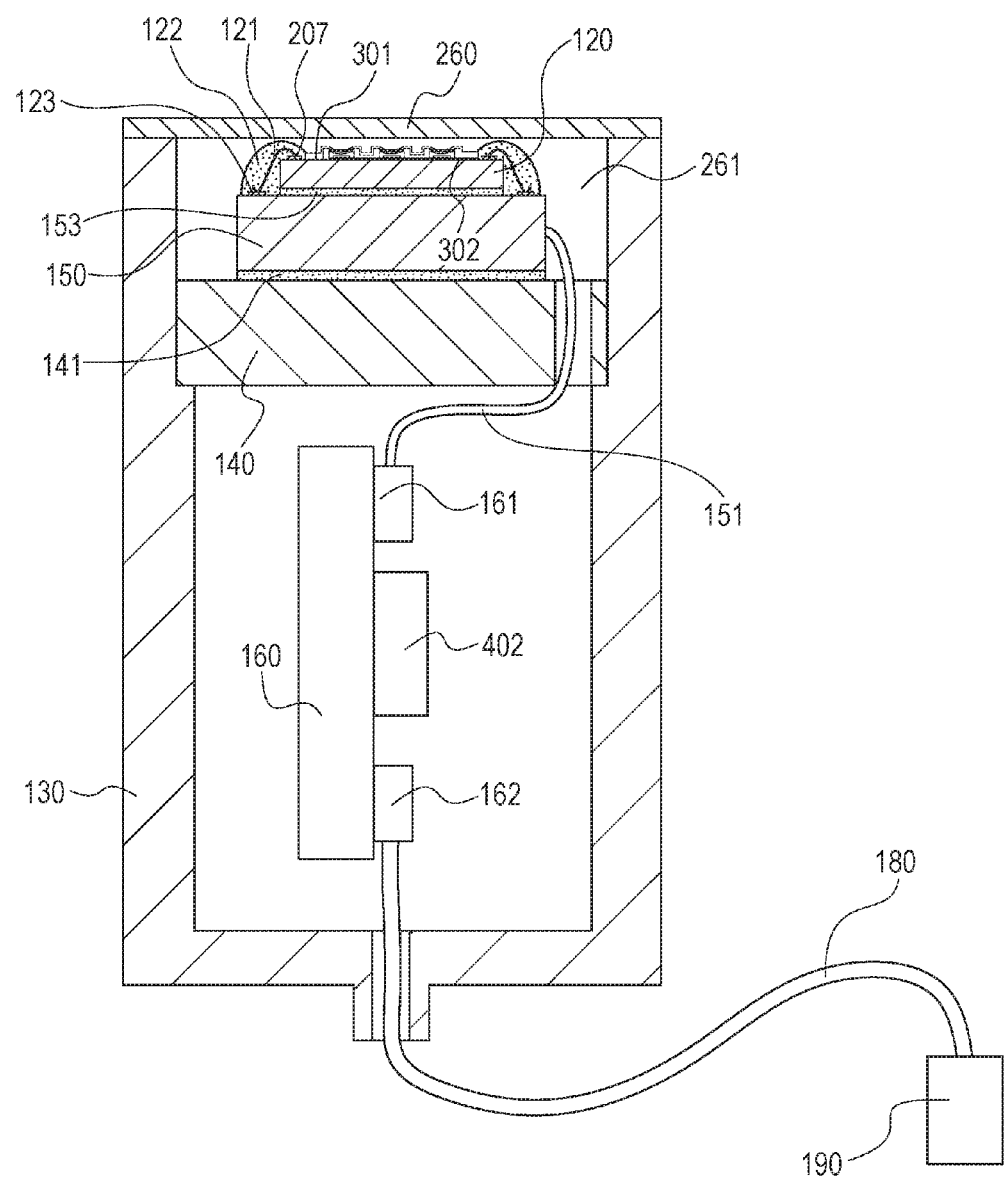
FIG. 16 is a schematic diagram of the photoacoustic probe according to a fifteenth exemplary embodiment of the present invention.

FIG. 16 is a schematic diagram of the photoacoustic probe according to the present exemplary embodiment. FIG. 16 illustrates an insulating film 260 and a silicone rubber layer 261.

According to the present exemplary embodiment, it is characterized in that the insulating film 260 is arranged on the CMUT via the silicone rubber layer 261.

The insulating film 260 can be made of a thin insulating film, and it is possible to use a material with which a thin film can be formed can be used, such as PET, PI, PE, or TPX. A sufficiently thin thickness with respect to a wavelength of the used ultrasonic wave can be used as a thickness of the insulating film 260, and the thickness is more preferably from a several micrometers to ten and a several micrometers.

The silicone rubber layer 261 has an excellent transmission characteristic of the acoustic wave and can strongly bond the insulating film 260 and the chip 120 to each other. Herein, the vibrating membrane 201 on the CMUT 110 side bonded to the insulating film 260 is thin and largely affected by the influence of the member arranged on the vibrating membrane 201. For this reason, when adhesive such as a general epoxy system having a high hardness after hardening is used, the characteristic of the vibrating membrane 201 is affected, and the reception sensitivity is significantly degraded. Since the silicone rubber has a low hardness after the hardening, it is possible to attain a characteristic that a vibrating characteristic of the vibrating membrane 201 of the CMUT 110 is hardly affected by arranging the silicone rubber on the front surface of the CMUT 110. A thickness of the silicone rubber layer 261 is more preferably lower than or equal to several tens of micrometers because a transmission characteristic of the ultrasonic wave is hardly affected. In addition, if an interval between the chip 120 and the insulating film 260 is too narrow, the reception characteristic of the photoacoustic wave (ultrasonic wave) of the vibrating membrane 201 is affected, and therefore, the thickness of the silicone rubber layer 261 is preferably higher than or equal to 20 micrometers. For these reasons, when the use in the photoacoustic probe is assumed, the thickness of the silicone rubber layer 261 according to the present exemplary embodiment is particularly preferably in a range between 20 micrometers and 40 micrometers.

According to the present exemplary embodiment, with the provision of the insulating film 260, the front surface of the CMUT 110 where the high voltage is applied to the electrode can be electrically insulated from the outside. For this reason, it is possible to provide the photoacoustic probe having a high safety with respect to the subject.

In addition, in the configuration according to the present exemplary embodiment, the silicone rubber layer 261 is arranged between the insulating film 260 and the chip 120. For this reason, it is possible to provide the photoacoustic probe in which the reception characteristic of the photoacoustic wave (ultrasonic wave) is hardly degraded while adhesion force of the insulating film 260 with respect to the chip 120 is secured.

According to the present exemplary embodiment, it is possible to provide the photoacoustic probe in which the wiring can be easily drawn out, and the high insulation property with respect to the outside is secured on the surface of the CMUT.

Sixteenth Exemplary Embodiment

A sixteenth exemplary embodiment relates to a DC voltage generation unit of a capacitive ultrasonic transducer. The other aspects are the same as any one of the first to fifteenth exemplary embodiments.

FIG. 17A illustrates an applied voltage adjustment unit 460. According to the present exemplary embodiment, it is characterized in that the applied voltage adjustment unit 460 is provided between the DC voltage generation unit 401 and the second electrode 203. The applied voltage adjustment unit 460 has a function of performing adjustment to Vo at a terminal where Vb output from the DC voltage generation unit 401 is applied to the second electrode 203.

Figure 17B:
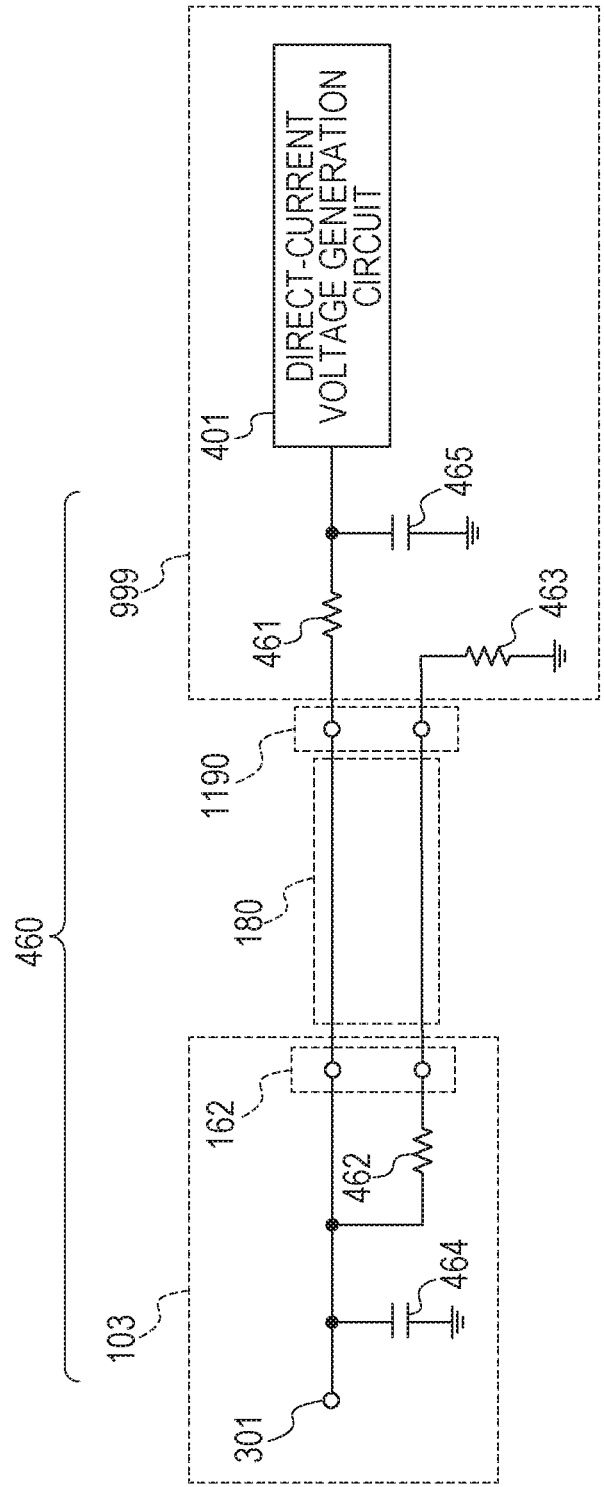

In the CMUT, an optimal value of the DC voltage applied to each of the elements is varied depending on a thickness variation of the vibrating membrane 201 or a variation of the gap 205. The ultrasonic probe according to the present exemplary embodiment has a function of applying the optimal DC voltage Vo to each of the elements of the CMUT. With reference to FIG. 17B, a circuit configuration of the applied voltage adjustment unit 460 will be described.

The applied voltage adjustment unit 460 is constituted by three resistances. A first voltage dividing resistance 461 is inserted between the DC voltage generation unit 401 and the second electrode 203. A second voltage dividing resistance 462 and a third voltage dividing resistance 463 are connected in series and arranged between the second wiring 302 on the second electrode 203 side and a GND terminal. Herein, a resistance value of the first voltage dividing resistance 461 is set as R1, a resistance value of the second voltage dividing resistance 462 is set as R2, and a resistance value of the third voltage dividing resistance 463 is set as R3. At this time, the voltage value Vo applied to the second wiring 302 on the second electrode 203 side can be represented as Vo=(R2+R3)/(R1+R2+R3)×Vb, and the optimal voltage that varies for each element can be applied to the CMUT.

According to the present exemplary embodiment, it is characterized in that the value of R2 is set to be lower than the value of R3. With this configuration, a drop voltage of the second voltage dividing resistance 462 is lower than a drop voltage of the third voltage dividing resistance 463. For this reason, the first voltage dividing resistance 461 and the third voltage dividing resistance 463 need to be a high breakdown voltage (several tens of volts to several hundreds of volts), but the second voltage dividing resistance 462 can use a breakdown voltage lower than the above-described breakdown voltage. The first voltage dividing resistance 461 and the third voltage dividing resistance 463 are constituted by large parts because of the resistances of the high breakdown voltage, but the second voltage dividing resistance 462 can use a small part.

With the presence of the second voltage dividing resistance, even when the resistance values of the first voltage dividing resistance 461 and the third voltage dividing resistance 463 are fixed, the applied voltage can be changed by only changing the resistance value of the second voltage dividing resistance 462. It is sufficient when the second voltage dividing resistance 462 is set as a resistance value to have an applied voltage corresponding to each element, and the replacement is facilitated since the second voltage dividing resistance 462 is the small part.

In addition, a first high voltage condenser 464 and a second high breakdown voltage condenser 465 are arranged for a purpose of suppressing fluctuations of the voltages at the respective terminals or noise contamination from the outside.

In the ultrasonic probe according to the present exemplary embodiment, since it is possible to apply the optimal DC voltage to each element, the characteristics of the CMUTs can be set to be uniform, and it is possible to obtain the high accuracy data. For this reason, when the ultrasonic probe according to the present exemplary embodiment is used, it is possible to obtain the high quality image.

According to the present exemplary embodiment, the first voltage dividing resistance 461 and the third voltage dividing resistance 463 are arranged inside an apparatus main body 999. The second voltage dividing resistance 462 is arranged on the circuit substrate 160 and set as a resistance value to an applied voltage corresponding to each element, and a different value is used for each element. For this reason, even when the ultrasonic transducer unit arranged on the supporting member is changed, it is possible to set the optimal applied voltage corresponding to each element without changing the value of the resistance of the apparatus main body 999. In addition, since the second voltage dividing resistance 462 has the low breakdown voltage and is the small part, it is possible to arrange the second voltage dividing resistance 462 in a small mounting area on the circuit substrate 160.

The wiring that connects the supporting member to the flexible part includes a third wiring 303 connected to the second voltage dividing resistance 462 in addition to the first wiring 301 connected to the first electrode 202 and the second wiring 302 connected to the second electrode 203. Accordingly, it is possible to adjust the voltage Vo applied to the CMUT by the second voltage dividing resistance 462 arranged on the circuit substrate 160.

According to the present exemplary embodiment, with regard to the probe having the plurality of ultrasonic transducers on the curved surface, the wirings that connect the respective elements with the outside can be realized by the simple configuration, and it is possible to provide the small-sized probe having the uniform and excellent reception frequency characteristics.

Seventeenth Exemplary Embodiment

A seventeenth exemplary embodiment relates to an arrangement of the detection circuit 402. The other aspects are the same as any one of the first to sixteenth exemplary embodiments.

Figure 18A:
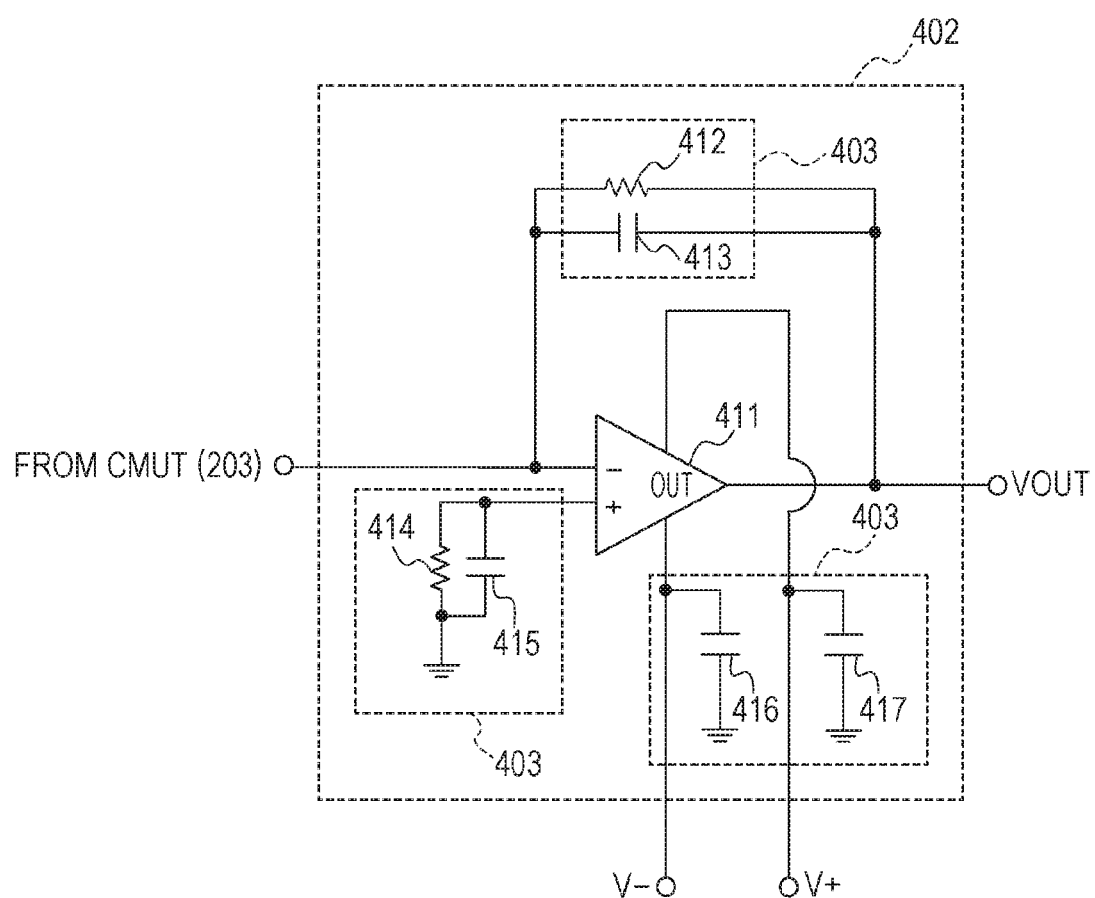
FIGS. 18A to 18C are schematic diagrams of the photoacoustic probe according to a seventeenth exemplary embodiment of the present invention.
Figure 18B:
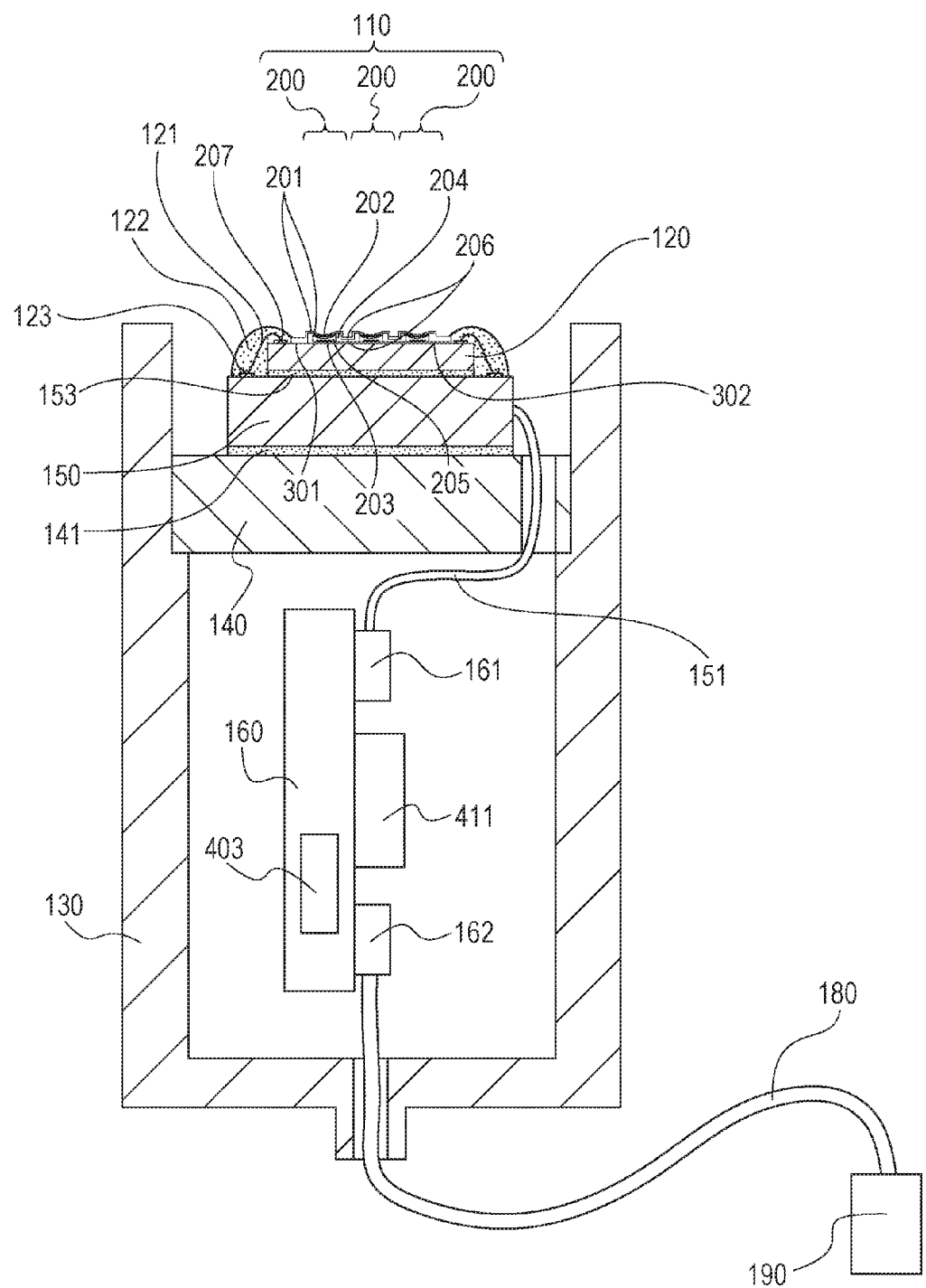
Figure 18C:
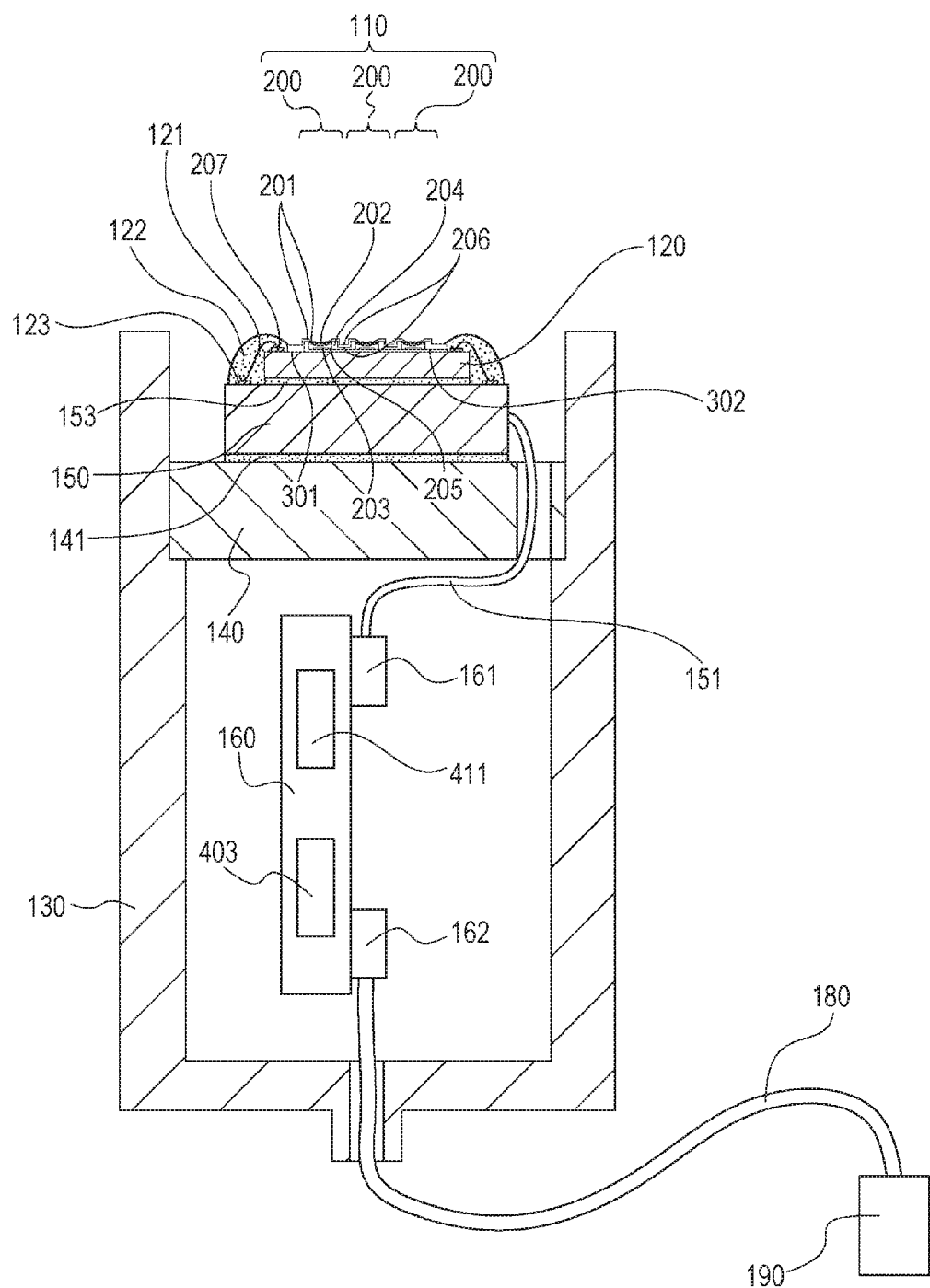

FIGS. 18A to 18C are schematic diagrams for describing the transducer unit of the photoacoustic probe according to the present exemplary embodiment. It is characterized in that the chip part of the detection circuit is arranged inside the circuit substrate 160 according to the present exemplary embodiment. As illustrated in FIG. 18A, the detection circuit 402 that detects the current when the CMUT receives the ultrasonic wave can be constituted by a transimpedance circuit using an operation amplifier. In a transimpedance circuit (transimpedance amplifier) using the operation amplifier, the resistance and the condenser are arranged in parallel to the negative feedback part of the operation amplifier, and the input current is converted into a voltage by the feedback part. Since the feedback characteristic of the operation amplifier exists, by using the operation amplifier having a broad band region, the current/voltage conversion efficiency can reduce the influence of the parasitic capacitance existing at the input wiring. For this reason, the excellent reception characteristic in which the decrease in the reception sensitivity is small is obtained as the reception characteristic having the wide frequency band with respect to the CMUT. According to the present exemplary embodiment, a configuration can be adopted in which parts included in the transimpedance circuit using the operation amplifier are partially built in the circuit substrate. In addition, a configuration can be adopted in which the operation amplifier included in the transimpedance circuit using the operation amplifier is also built in the circuit substrate. That is, as illustrated in FIG. 18B, it is characterized in that the resistance of the detection circuit and the chip parts such as the capacitance are provided inside the rigid part. The configuration in which the parts are arranged inside the circuit substrate can be easily realized by using a fabrication technology for a part-built-in substrate. In addition, the operation amplifier other than the chip parts of the detection circuit is arranged on the back surface of the circuit substrate. According to the configuration of FIG. 18B, the chip resistance is built in the circuit substrate, so that the mounting area of the detection circuit 402 can be reduced. For this reason, when the size of the CMUT or the chip is reduced too, the mounting area of the detection circuit is constrained, and it is possible to avoid a situation where the respective intervals are not narrowed.

According to the present exemplary embodiment, it is possible to provide the photoacoustic probe in which the wiring can be easily drawn out, and the detection circuits of the ultrasonic transducers having the excellent reception frequency characteristic are arranged at a high density.

Another mode of the present exemplary embodiment will be described with reference to FIG. 18C. According to this another mode, it is characterized in that the entire detection circuit 402 is arranged inside the circuit substrate. Accordingly, the entire circuit is covered with the circuit substrate made of the epoxy resin, and it is possible to reduce the generation of the defect of the electric connection part or the defect of the operation amplifier caused by moisture or the like.

According to another mode of the present exemplary embodiment, it is possible to provide the photoacoustic probe including the highly reliable detection circuit of the ultrasonic transducer in which the wiring can be easily drawn out, and the reception frequency characteristic is excellent.

Eighteenth Exemplary Embodiment

According to an eighteenth exemplary embodiment, a difference resides in that the CMUT 110 also has a function of transmitting and receiving the ultrasonic wave. That is, the transducer unit according to the present exemplary embodiment has a configuration in which a CMUT to which the driving detection circuit configured to perform reception of the photoacoustic wave and transmission and reception of the ultrasonic wave is arranged on the chip.

Figure 19B:
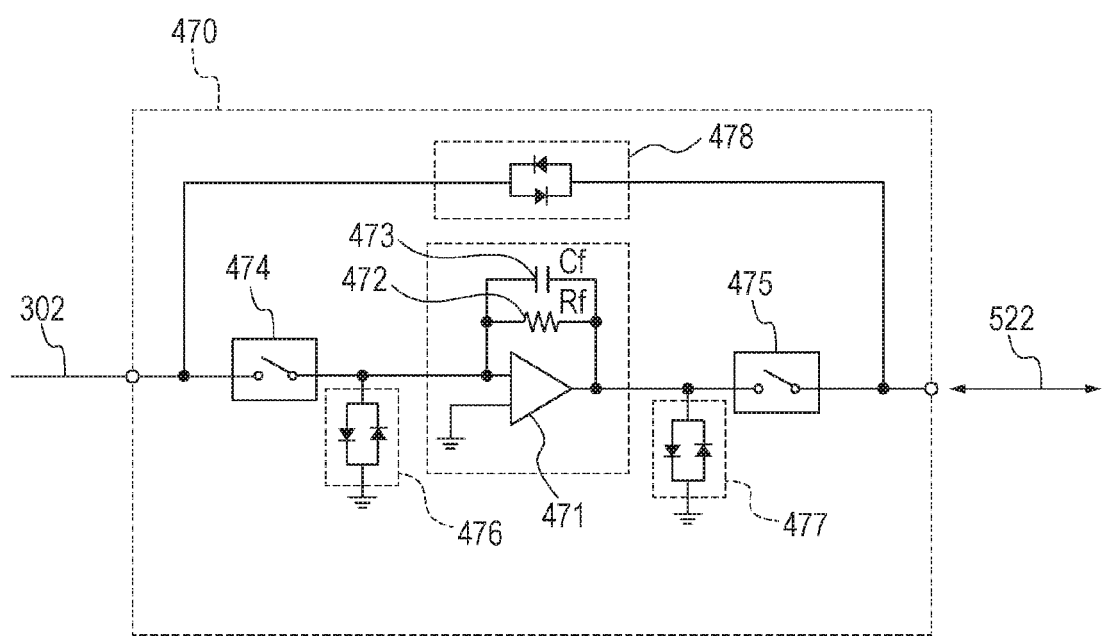

The other aspects are the same as any one of the first to seventeenth exemplary embodiments. Descriptions will be given with reference to FIGS. 19A and 19B. In FIGS. 19A and 19B, reference symbol 521 denotes a DC voltage value instruction signal, and reference symbol 522 denotes a detection signal of a minute current and a high voltage pulse for transmission.

FIGS. 19A and 19B illustrate a driving detection circuit 470, an operation amplifier 471, a feedback resistance 472, a feedback capacitance 473, high breakdown voltage switches 474 and 475, diodes 476 and 477, and a high breakdown voltage diode 478. FIG. 19A is a schematic diagram of an electrostatic transducer 198 arranged in the ultrasonic probe arranged on the single chip. One element of the electrostatic transducer 198 is arranged on the single chip, and the first electrode 202 of the electrostatic transducer 198 is connected to the driving detection circuit 470. The driving detection circuit 470 has a function of applying the high voltage pulse used in the transmission of the ultrasonic wave from the apparatus side to a CMUT 198 and outputting a minute current from the CMUT 198 as a detection signal to the apparatus side.

FIG. 19B is a circuit diagram for describing the driving detection circuit 470. The negative feedback part of the operation amplifier 471 has the feedback resistance and the feedback capacitance 473 arranged in parallel and has a function of performing the current/voltage conversion. The high breakdown voltage switches 474 and 475 and the diodes 477 and 478 are respectively connected to an input terminal and an output terminal of the operation amplifier. In a case where a high breakdown voltage 439 is a voltage lower than or equal to a predetermined voltage (below one volt) between the terminals, the wiring connection between the terminals is cut off. When a voltage higher than a predetermined voltage (approximately several volts) is applied to the high breakdown voltage switches 474 and 475, the wirings between the input and output terminals of the switches are cut off.

When the application of the high voltage pulse for the transmission is not performed, the high breakdown voltage 439 has almost no potential difference between the terminals, and therefore, a state is established in which the wiring at the input and output terminals is cut with the high breakdown voltage 439. On the other hand, since a high voltage is not applied to the high breakdown voltage switches 474 and 475 from the outside, the wiring between the switches is connected. For this reason, a minute current from the transducer is subjected to the current/voltage conversion by the operation amplifier, and a detection signal can be output to an apparatus (not illustrated) connected to the outside.

On the other hand, when the high voltage pulse for the transmission is applied from the apparatus (not illustrated) side, the wiring inside the high breakdown voltage 439 is connected, and a voltage higher than the predetermined voltage (approximately several volts) is applied to the high breakdown voltage switches 474 and 475. For this reason, the high breakdown voltage switches 474 and 475 cut the wirings inside the switches. For this reason, it is possible to avoid a damage to the operation amplifier when the high voltage is applied to the operation amplifier. The signal output from the operation amplifier is cut by the high breakdown voltage switch 475, which does not affect the high voltage pulse applied for the transmission. For this reason, it is possible to apply the high voltage pulse to the first electrode of the transducer for transmitting the ultrasonic wave.

With the ultrasonic probe according to the present exemplary embodiment, the reception of the photoacoustic wave and the transmission and reception of the ultrasonic wave can be performed by the single probe. For this reason, it is possible to form a photoacoustic imaging image and an ultrasonic imaging image on the basis of the detected data. In addition, since the CMUT 198 used for the transmission of the ultrasonic wave and the reception of the ultrasonic wave and the photoacoustic wave can perform the transmission and the reception alone, it is possible to decrease the size of the chip 120. For this reason, the elements 198 can be arranged in closer proximity to one another, and the number of elements can be increased. As an alternative to the above, in a case where the same number of elements is used, it is possible to realize the hemisphere having a smaller diameter. In addition, since the CMUT 198 is used for combined purposes, it is possible to obtain an image in which registration shift of the photoacoustic imaging image and the ultrasonic imaging image is further suppressed.

Nineteenth exemplary embodiment

A nineteenth exemplary embodiment relates to the driving detection circuit 402 connected to the CMUT 110 on the chip 120. That is, a following configuration is adopted. The transducer unit includes a plurality of CMUTs, and the plurality of CMUTs are divided into a plurality of areas including at least one CMUT. Each of the CMUTs in the divided area is provided with the driving detection circuit and functions as one CMUT at the time of the transmission and reception of the ultrasonic wave or the reception of the photoacoustic wave. The other aspects are the same as any one of the first to eighteenth exemplary embodiments.

Figure 20A:
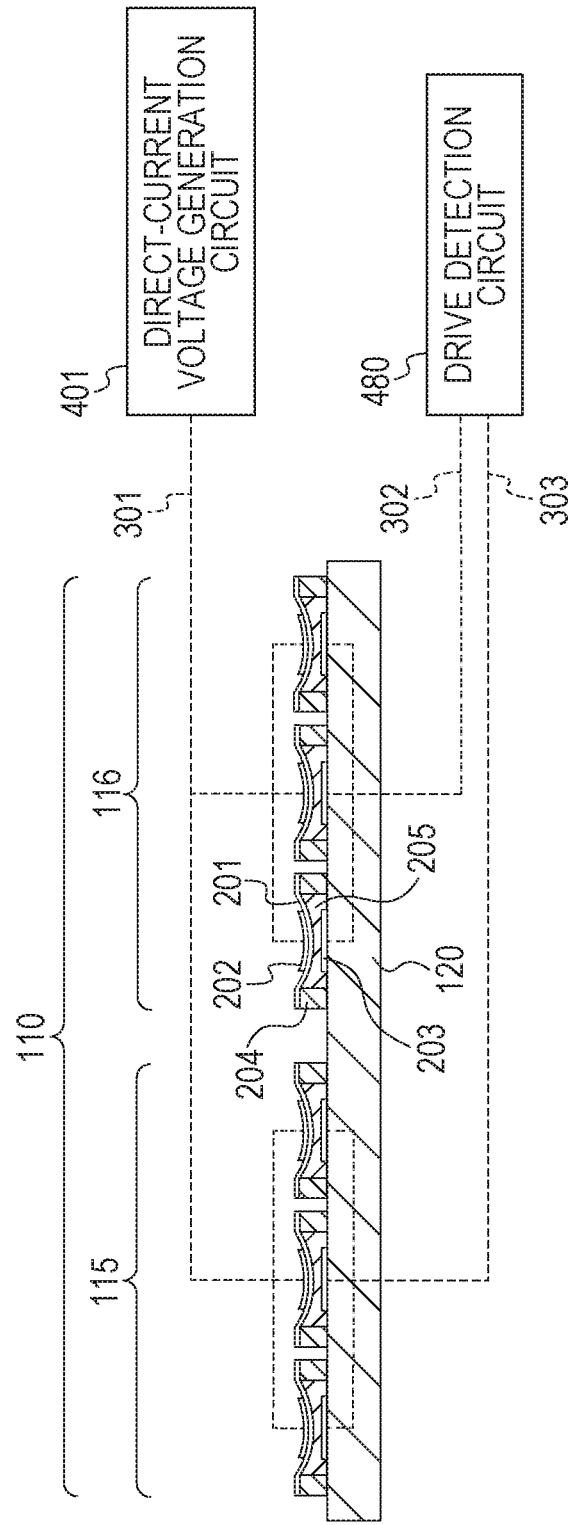
FIGS. 20A to 20C are schematic diagrams of the photoacoustic probe according to a nineteenth exemplary embodiment of the present invention.
Figure 20B:
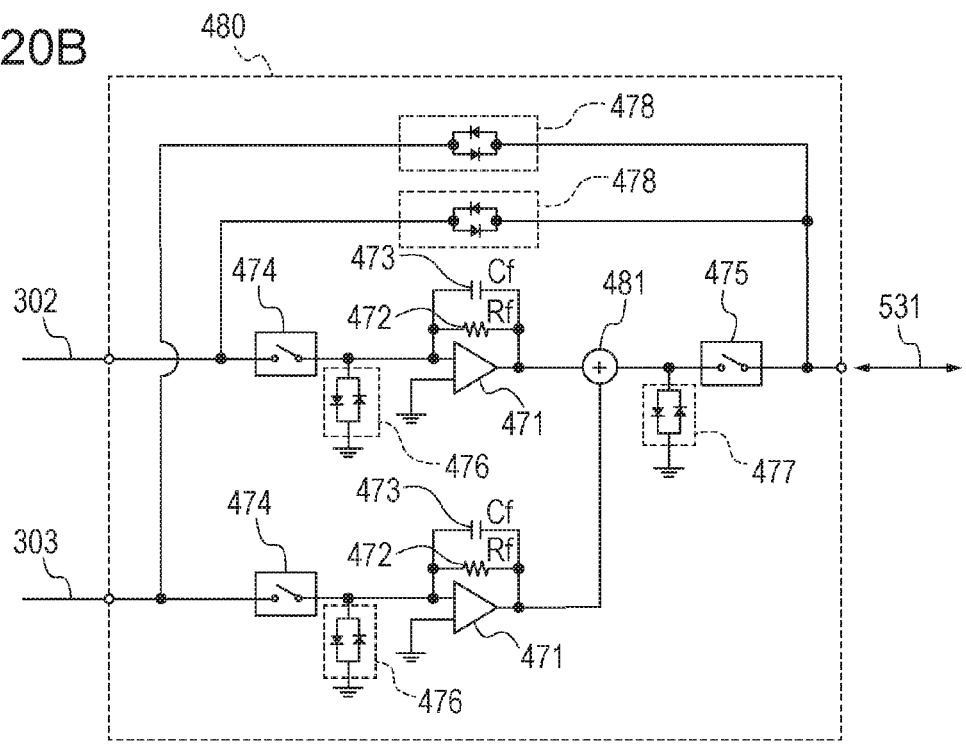
Figure 20C:
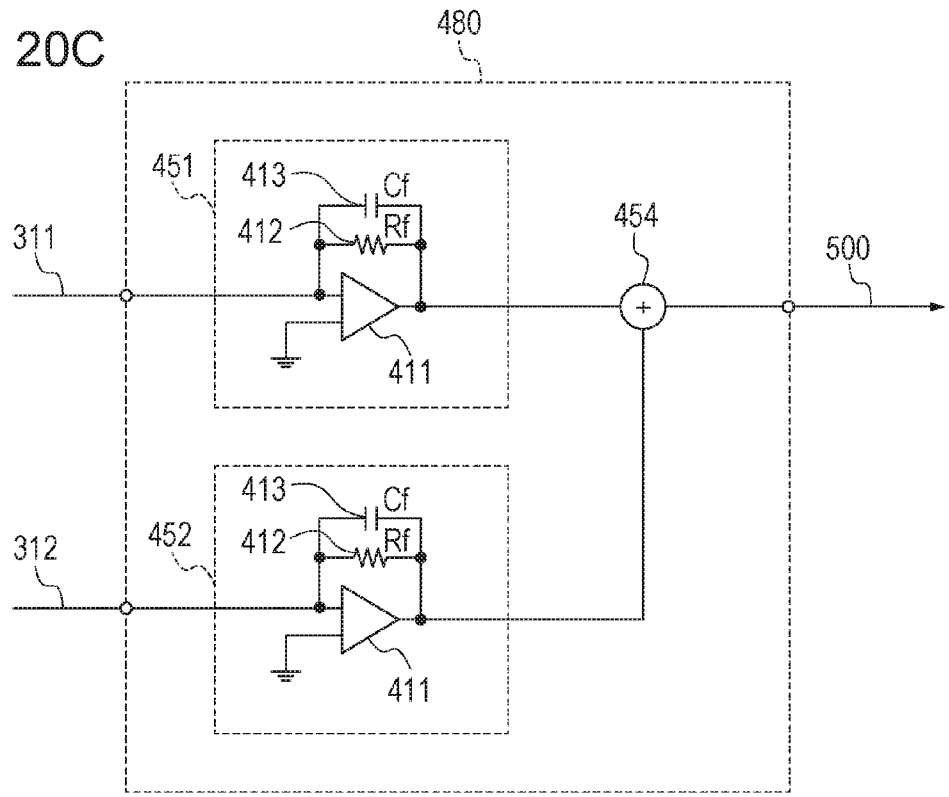

FIGS. 20A to 20C are schematic diagrams of the photoacoustic probe according to the present exemplary embodiment.

According to the present exemplary embodiment, it is characterized in that CMUTs 115 and 116 divided into a plurality of areas are provided on the chip 120. Specifically, a plurality of groups in which the second electrodes 203 of the CMUT 110 are electrically connected to each other are arranged on the chip 120. The wiring from the second electrode 203 of each of the groups is connected to a different input terminal of a driving detection circuit 480 arranged on the interposer (not shown). At the time of the transmission of the ultrasonic wave, a high voltage driving signal from the external apparatus is applied from each terminal to the first electrode 202 of the CMUT 110 via a plurality of transmission diodes in the driving detection circuit 403.

On the other hand, at the time of the reception, the signal from each of the second electrodes 203 is amplified by the operation amplifier 411 to be output as a voltage from each of the operation amplifiers. Each of the output voltages is output from the wiring 310 in the cable 160 while the voltage signals are combined with each other in an adder 483.

Herein, the maximum value of the capacitance that can be connected to the input terminal of each of the operation amplifiers is determined on the basis of a resistance of the feedback part, a size of the condenser, and a gain frequency characteristic of the operation amplifier. According to the present exemplary embodiment, the CMUT 110 is divided, and the operation amplifier is connected to each of the divided parts. Thus, it is possible to reduce the size of the capacitance of the CMUT connected to each of the operation amplifiers. Accordingly, a parameter of the feedback part of the operation amplifier can be more appropriately set, and the reception frequency band can be widened, so that it is possible to further utilize the characteristic of the CMUT 110 having the wide band.

In the transimpedance circuit using the operation amplifier, the output noise changes depending on the capacitance connected to the input terminal of the operation amplifier. According to the present exemplary embodiment, the CMUT 110 is divided, and the operation amplifier is connected to each of the divided parts, so that the output noise of the single current/voltage conversion circuit can be reduced. In a case where the output from each of the operation amplifiers is added to one another by an adder 481, when the number of division is set as X, the output noise can be reduced to approximately $1/\sqrt{X}$. Thus, the output noise is reduced as a whole, and it is possible to perform the highly accurate detection of the reception signal.

In this manner, by using the circuit configuration according to the present exemplary embodiment, the transmission and reception of the ultrasonic wave from the CMUT can be performed without the control signal from the outside. For this reason, it is possible to provide the ultrasonic probe that has the excellent frequency characteristic of the current/voltage conversion at the time of the reception and performs the excellent reception operation in which the noise of the output signal is hardly generated.

In addition, as another mode of the present exemplary embodiment, as illustrated in FIG. 20C, it is also possible to adopt a configuration in which a plurality of detection circuits 402 are provided, and outputs are combined to one another by an adder 454 to be output. Similarly as in FIG. 20B, it is possible to attain the effect that the output noise is reduced, and the high accuracy detection of the reception signal is performed.

Twentieth Exemplary Embodiment

The acoustic probe according to any one of the first to nineteenth exemplary embodiments can be used for the reception of the photoacoustic wave (ultrasonic wave) using a photoacoustic effect and applied to a photoacoustic apparatus including the same. Specifically, a configuration is adopted in which the plurality of transducer units according to the above-described respective exemplary embodiments of the present invention and the supporting member including the hemispheric surface having a plurality of through holes are provided, and the plurality of transducer units are fixed in the respective through holes such that the plurality of transducer units face the center of the hemisphere. According to the configuration, the photoacoustic wave generated by the photoacoustic effect is received by using this acoustic probe. It should be noted that the acoustic probe is a concept including both the photoacoustic probe used for the reception of the ultrasonic wave (photoacoustic wave) and the ultrasonic probe that can perform the transmission and reception of the ultrasonic wave.

Figure 21:
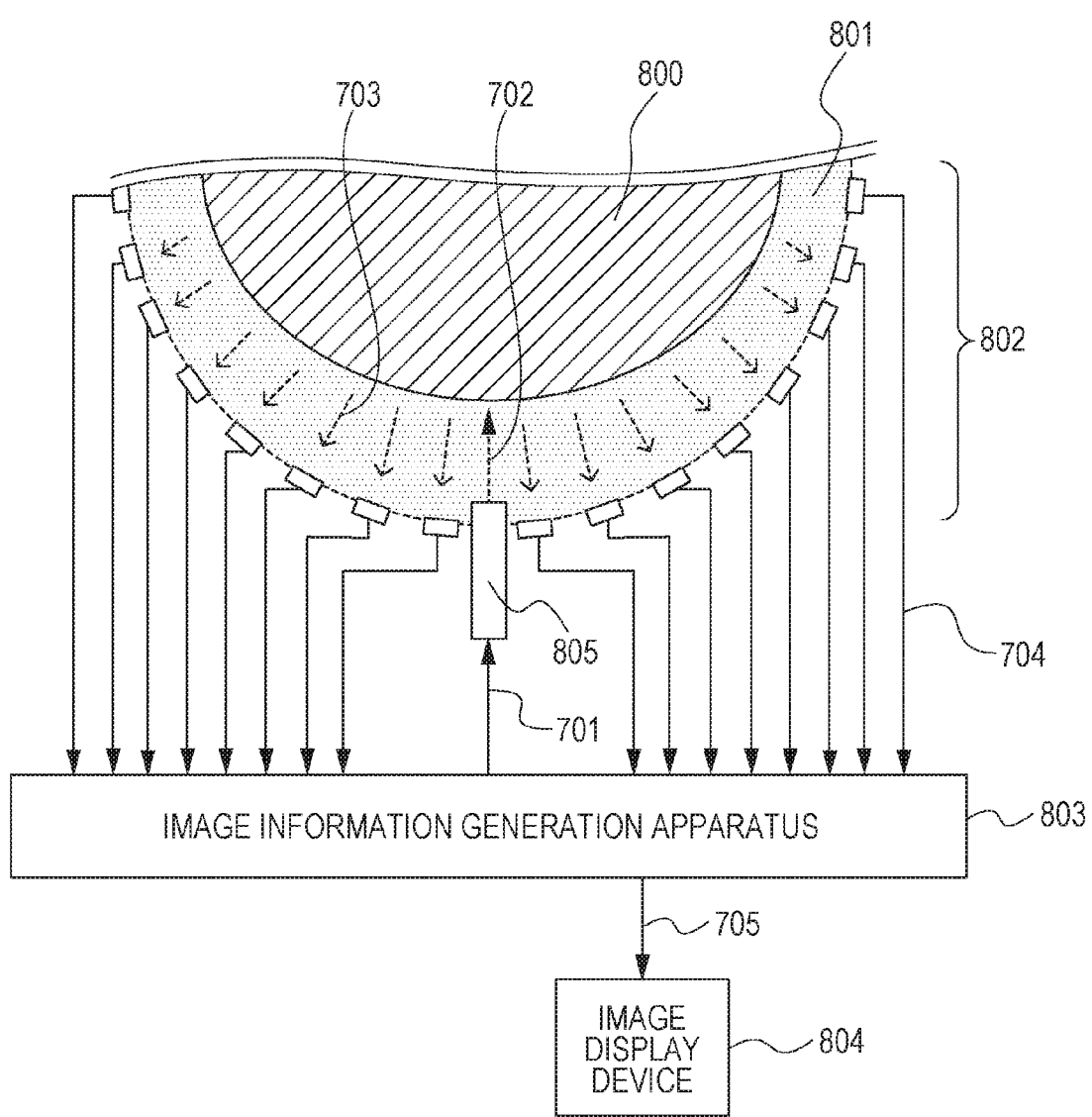
FIG. 21 is a schematic diagram of a photoacoustic apparatus according to a twentieth exemplary embodiment of the present invention.

An operation of an ultrasonic measurement apparatus according to the present exemplary embodiment will be specifically described with reference to FIG. 21. First, on the basis of a light emission instruction signal 701, light 702 (pulsed light) is generated from a light source 805, and a measurement object 800 is irradiated with the light 702. A photoacoustic wave (ultrasonic wave) 703 is generated due to the irradiation of the light 702 in the measurement object 800, and the ultrasonic wave 703 is received by a plurality of CMUTs 802 included in the ultrasonic probe. Information on the size, the shape, or the time of the reception signal is transmitted to an image information generation apparatus 803 as a photoacoustic wave reception signal 704. On the other hand, information (light emission information) on the size, the shape, or the time of the light 702 generated by the light source 805 is stored in the image information generation apparatus 803 of the photoacoustic signal. In the image information generation apparatus 803 of the photoacoustic signal, an image signal of the measurement object 800 is generated on the basis of the photoacoustic reception signal 703 and the light emission information and output as reproduction image information 705 based on the photoacoustic signal. An image display device 804 displays the measurement object 800 as an image on the basis of the reproduction image information 705 based on the photoacoustic signal.

The acoustic probe according to the present exemplary embodiment has such a characteristic that the photoacoustic wave in the wide frequency range can be received, and much information can be obtained from the photoacoustic wave, so that it is possible to generate the high quality image.

Twenty-First Exemplary Embodiment

According to the present exemplary embodiment, the ultrasonic probe that can perform the transmission of the ultrasonic wave according to the eighteenth or nineteenth exemplary embodiment is used in the photoacoustic apparatus according to the twentieth exemplary embodiment.

Figure 22:
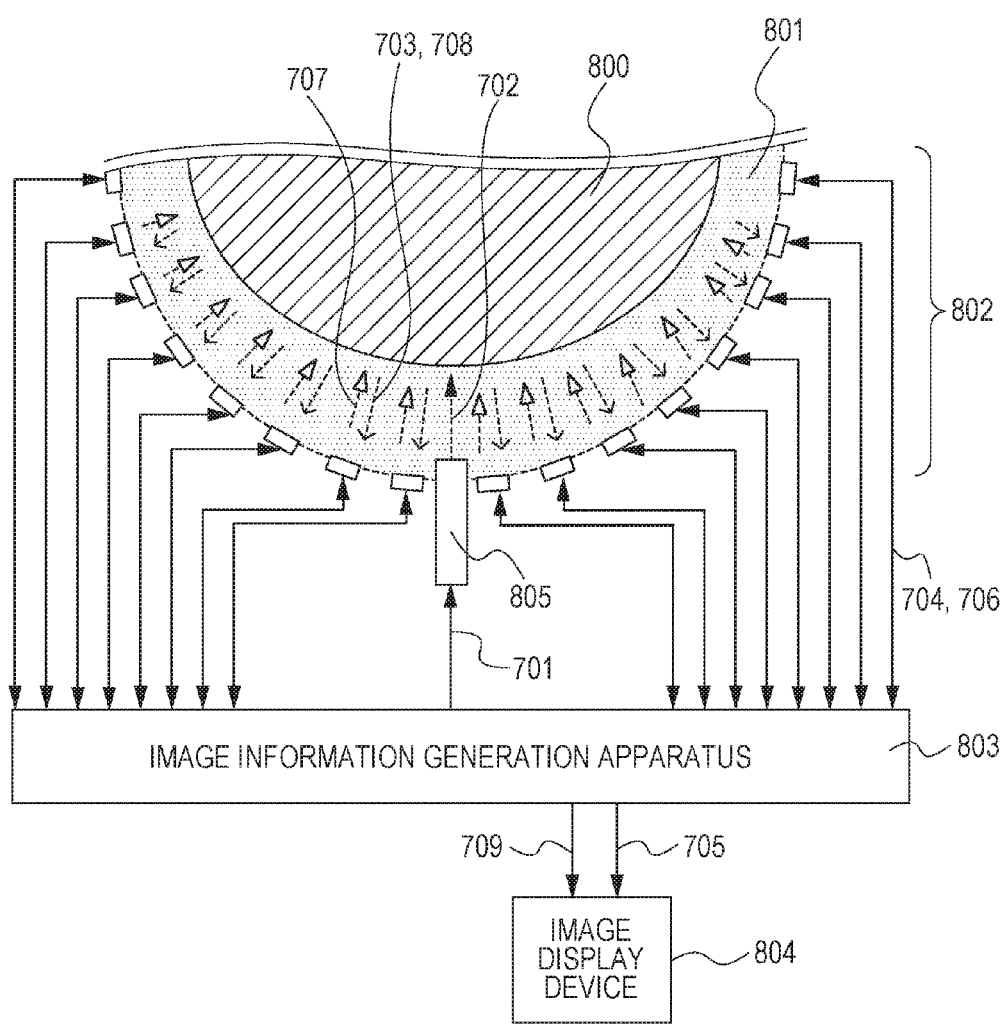
FIG. 22 is a schematic diagram of the photoacoustic apparatus according to a twenty-first exemplary embodiment of the present invention.
Figure 23:
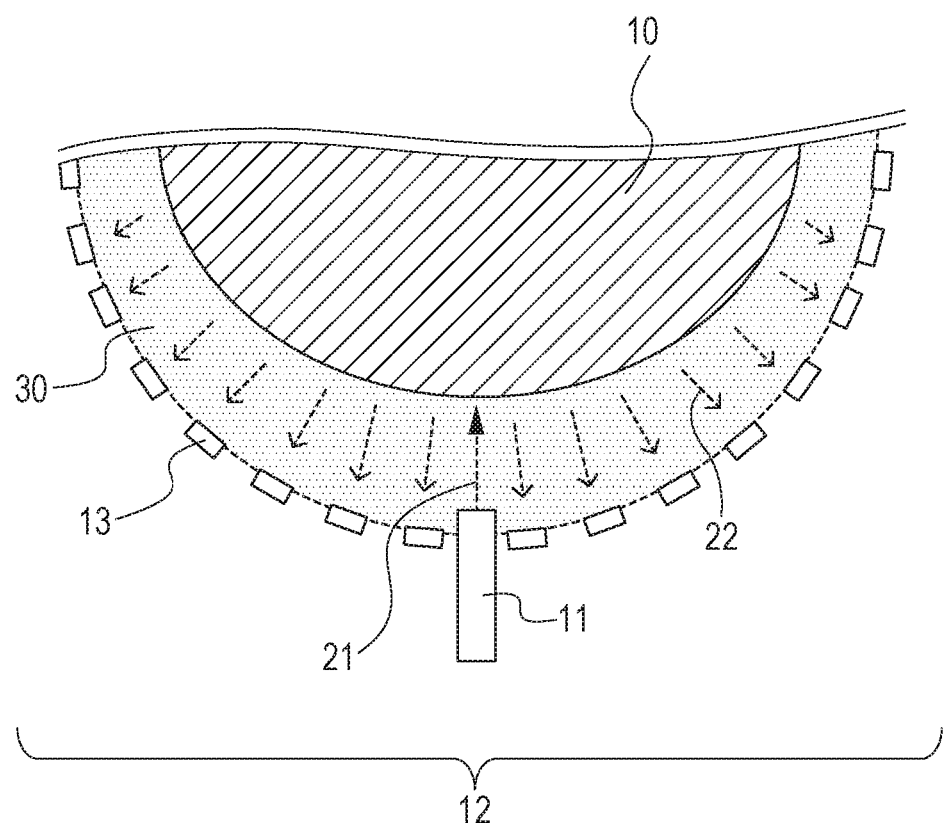
FIG. 23 is a schematic diagram for describing a photoacoustic apparatus in a related art.

FIG. 22 is a schematic diagram of a photoacoustic apparatus according to the present exemplary embodiment. FIG. 22 illustrates a transmission/reception signal 706 of the ultrasonic wave, a transmitted ultrasonic wave 707, a reflected ultrasonic wave 708, and reproduction image information 709 based on the transmission and reception of the ultrasonic wave.

According to the present exemplary embodiment, a configuration is adopted in which the reception of the photoacoustic wave generated by the photoacoustic effect and the transmission and reception of the ultrasonic wave are performed by using the acoustic probe. That is, the photoacoustic apparatus according to the present exemplary embodiment performs pulse echo (transmission and reception of the ultrasonic wave) in addition to the reception of the photoacoustic wave and forms an image. Since the reception of the photoacoustic wave is the same as the twelfth exemplary embodiment, the pulse echo (transmission and reception of the ultrasonic wave) will be described herein.

The ultrasonic wave 706 is output (transmitted) from the plurality of CMUTs 802 towards the measurement object 800 on the basis of the transmission signal 706 of the ultrasonic wave. The ultrasonic wave is reflected inside the measurement object 800 due to a difference of specific acoustic impedance of an intrinsic substance. The reflected ultrasonic wave 708 is received by the plurality of CMUTs 802, and information on the size, the shape, or the time of the reception signal is transmitted to the image information generation apparatus 803 as the ultrasonic wave reception signal 706. On the other hand, the information on the size, the shape, or the time of the transmission ultrasonic wave is stored in the image information generation apparatus 803 as ultrasonic wave transmission information. The image information generation apparatus 803 generates an image signal of a measurement object 700 on the basis of the ultrasonic wave reception signal 706 and the ultrasonic wave transmission information to be output as the reproduction image information 709 of the ultrasonic wave transmission and reception.

The image display device 804 displays the measurement object 800 on the image on the basis of two pieces of information including the reproduction image information 705 based on the photoacoustic signal and the reproduction image information 709 based on the ultrasonic wave transmission and reception.

According to the present exemplary embodiment, pieces of reception information of different measurement methods are obtained by using the ultrasonic probe having such a characteristic that the photoacoustic wave in the wide frequency range can be received, and the image is formed, so that it is possible to obtain and display the image having the still more information amount.

In the present specification, the first electrode 202 is arranged on the vibrating membrane 201, and the second electrode 203 is arranged on the substrate 120, but the present invention is not limited to this configuration. A configuration may also be adopted in which the second electrode 203 is arranged on the vibrating membrane 201, and the first electrode 202 is arranged on the substrate 120.

According to the exemplary embodiments of the present invention, the small-sized transducer unit can be provided, and the photoacoustic probe in which the plurality of transducer units are arranged in proximity to one another on the supporting member can be provided, so that it is possible to improve the image quality of the subject.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-175014, filed Sep. 4, 2015, which is hereby incorporated by reference herein in its entirety.

What is claimed is:

1. A transducer unit comprising:
   a chip;
   a capacitive transducer provided on the chip and configured to receive an acoustic wave generated when a subject is irradiated with light from a light source and output an electric signal;
   a circuit substrate including a current/voltage conversion circuit configured to convert a current output from the capacitive transducer into a voltage; and
   a flexible printed wiring that electrically connects the capacitive transducer to the current/voltage conversion circuit,
   wherein the circuit substrate is provided on a surface side opposite to a surface where the capacitive transducer is provided among surfaces of the chip.

2. The transducer unit according to claim 1, wherein the chip includes a through wiring, and the through wiring connected to an electrode of the capacitive transducer is drawn out to the surface opposite to the surface where the capacitive transducer is arranged among the surfaces of the chip.

3. The transducer unit according to claim 2, further comprising:
   a rigid flexible printed circuit board in which the flexible printed wiring and a rigid substrate are integrated to each other,
   wherein the surface opposite to the surface where the capacitive transducer is arranged among the surfaces of the chip is arranged at a position facing an electrode provided on the rigid substrate of the rigid flexible printed circuit board, and the electrode and the capacitive transducer are electrically connected to each other.

4. The transducer unit according to claim 2, wherein the surface opposite to the surface where the capacitive transducer is arranged among the surfaces of the chip is arranged at a position facing the flexible printed wiring, and the capacitive transducer and the flexible printed wiring are electrically connected to each other.

5. The transducer unit according to claim 1, wherein the surface of the chip and the flexible printed wiring are connected to each other via anisotropic conductive resin.

6. The transducer unit according to claim 1, further comprising:
   a supporting part that supports the chip,
   wherein the supporting part includes a concave part corresponding to an external shape of the chip for positioning the chip.

7. The transducer unit according to claim 1, further comprising:
   a supporting part that supports the chip,
   wherein the supporting part includes a through hole for drawing out the flexible printed wiring to a surface side opposite to a surface where the capacitive transducer is provided among surfaces of the supporting part.

8. The transducer unit according to claim 1, further comprising:
   an electrostatic shield.

9. The transducer unit according to claim 8, wherein the electrostatic shield is affixed and integrated to the flexible printed wiring.

10. The transducer unit according to claim 1, wherein the flexible printed wiring and the circuit substrate are connected to each other by anisotropic conductive resin.

11. The transducer unit according to claim 1, wherein the flexible printed wiring and the circuit substrate are connected to each other by soldering.

12. The transducer unit according to claim 1, wherein a detection circuit is provided on the circuit substrate, the detection circuit is covered with a shield cover, and the detection circuit and the shield cover are electrically connected to each other and also fixed by soldering.

13. The transducer unit according to claim 12, wherein a radiating sheet is provided between the detection circuit and the shield cover.

14. The transducer unit according to claim 12, further comprising:
   a casing,
   wherein the shield cover is fixed to the casing.

15. The transducer unit according to claim 1, wherein the circuit substrate and a cable for a connection with an external apparatus are connected to each other by using soldering, and the soldering is surrounded by a sealing material.

16. The transducer unit according to claim 1, wherein a card-edge connector is connected to the circuit substrate, and the circuit substrate is connected to an external apparatus by a cable connected to the card-edge connector.

17. The transducer unit according to claim 1, further comprising:
   a casing,
   wherein part of the casing is constituted by two parts so as to sandwich the circuit substrate.

18. The transducer unit according to claim 1, further comprising:
   a cylindrical casing.

19. The transducer unit according to claim 1, wherein an insulating film is provided on the capacitive transducer via a silicone rubber layer.

20. The transducer unit according to claim 1, further comprising:
   three resistances including a first voltage dividing resistance, a second voltage dividing resistance, and a third voltage dividing resistance,
   wherein a DC voltage applied to the electrode of the capacitive transducer is adjusted by using the three resistances.

21. The transducer unit according to claim 20, wherein the second voltage dividing resistance is provided on the circuit substrate.

22. The transducer unit according to claim 1, wherein a circuit configured to detect a current when the capacitive transducer receives an ultrasonic wave is a transimpedance circuit using an operation amplifier and is arranged on the circuit substrate.

23. The transducer unit according to claim 22, wherein parts included in the transimpedance circuit using the operation amplifier are partially built in the circuit substrate.

24. The transducer unit according to claim 22, wherein the operation amplifier included in the transimpedance circuit using the operation amplifier is built in the circuit substrate.

25. The transducer unit according to claim 1, wherein a capacitive transducer connected to a driving detection circuit configured to perform reception of a photoacoustic wave and transmission and reception of an ultrasonic wave is arranged on the chip.

26. The transducer unit according to claim 25, further comprising:
a plurality of the capacitive transducers,
wherein the plurality of capacitive transducers are divided into a plurality of areas including at least one capacitive transducer, and each of the capacitive transducers in the divided areas includes a driving detection circuit and functions as a single capacitive transducer upon transmission and reception of an ultrasonic wave or reception of a photoacoustic wave.

27. The transducer unit according to claim 1, further comprising:
a casing,
wherein the chip, the capacitive transducer, the circuit substrate and the flexible printed wiring and included in the casing.

28. An acoustic probe comprising:
a plurality of the transducer units according to claim 27; and
a supporting member including a surface having a shape of a hemisphere and including a plurality of through holes,
wherein the plurality of transducer units are fixed to the plurality of through holes.

29. A photoacoustic apparatus configured to receive a photoacoustic wave generated by a photoacoustic effect by using the acoustic probe according to claim 28.

30. A photoacoustic apparatus configured to perform reception of a photoacoustic wave generated by a photoacoustic effect and transmission and reception of an ultrasonic wave by using the acoustic probe according to claim 28.

31. A transducer unit comprising:
a chip;
a capacitive transducer provided on the chip and configured to receive an acoustic wave generated when a subject is irradiated with light from a light source and output an electric signal;
a circuit substrate including a current/voltage conversion circuit configured to convert a current output from the capacitive transducer into a voltage; and
a wiring that electrically connects the capacitive transducer to the current/voltage conversion circuit,
wherein the circuit substrate is provided on a surface side opposite to a surface where the capacitive transducer is provided among surfaces of the chip.

32. The transducer unit according to claim 31, further comprising:
an electrostatic shield,
wherein the electrostatic shield is affixed and integrated to the wiring.

33. The transducer unit according to claim 31, further comprising:
a casing,
wherein the chip, the capacitive transducer, the circuit substrate and the wiring are included in the casing.

34. An acoustic probe comprising:
a plurality of the transducer units according to claim 33; and
a supporting member including a surface having a shape of a hemisphere and including a plurality of through holes,
wherein the plurality of transducer units are fixed to the plurality of through holes.

\* \* \* \* \*